(12) United States Patent
Zhang et al.

(10) Patent No.: US 12,195,723 B2
(45) Date of Patent: Jan. 14, 2025

(54) ENGINEERED ANTIGEN PRESENTING CELLS AND USES THEREOF

(71) Applicants: THE BROAD INSTITUTE, INC., Cambridge, MA (US); MASSACHUSETTS INSTITUTE OF TECHNOLOGY, Cambridge, MA (US)

(72) Inventors: Feng Zhang, Cambridge, MA (US); Blake Lash, Cambridge, MA (US); Daniel Strebinger, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 297 days.

(21) Appl. No.: 17/093,011

(22) Filed: Nov. 9, 2020

(65) Prior Publication Data
US 2021/0147799 A1 May 20, 2021

Related U.S. Application Data

(60) Provisional application No. 62/933,016, filed on Nov. 8, 2019.

(51) Int. Cl.
*A61K 39/00* (2006.01)
*C07K 14/74* (2006.01)
*C12N 5/0781* (2010.01)
*C12Q 1/6881* (2018.01)

(52) U.S. Cl.
CPC ........ *C12N 5/0635* (2013.01); *A61K 39/4611* (2023.05); *A61K 39/4612* (2023.05); *A61K 39/4621* (2023.05); *A61K 39/4622* (2023.05); *A61K 39/4632* (2023.05); *A61K 39/46433* (2023.05); *A61K 39/464488* (2023.05); *A61K 39/464491* (2023.05); *C07K 14/70539* (2013.01); *C12Q 1/6881* (2013.01); *A61K 2239/31* (2023.05); *C12N 2502/30* (2013.01); *C12N 2510/00* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,686,281 | A | 11/1997 | Roberts |
| 5,843,728 | A | 12/1998 | Seed et al. |
| 5,851,828 | A | 12/1998 | Seed et al. |
| 5,906,936 | A | 5/1999 | Eshhar et al. |
| 5,912,170 | A | 6/1999 | Seed et al. |
| 5,912,172 | A | 6/1999 | Eshhar et al. |
| 6,004,811 | A | 12/1999 | Seed et al. |
| 6,284,240 | B1 | 9/2001 | Seed et al. |
| 6,392,013 | B1 | 5/2002 | Seed et al. |
| 6,410,014 | B1 | 6/2002 | Seed et al. |
| 6,489,458 | B2 | 12/2002 | Hackett et al. |
| 6,753,162 | B1 | 6/2004 | Seed et al. |
| 7,148,203 | B2 | 12/2006 | Hackett et al. |
| 7,160,682 | B2 | 1/2007 | Hackett et al. |
| 7,741,465 | B1 | 6/2010 | Eshhar et al. |
| 7,985,739 | B2 | 7/2011 | Kay et al. |
| 8,088,379 | B2 | 1/2012 | Robbins et al. |
| 8,211,422 | B2 | 7/2012 | Eshhar et al. |
| 8,227,432 | B2 | 7/2012 | Hackett et al. |
| 8,399,645 | B2 | 3/2013 | Campana et al. |
| 8,697,854 | B2 | 4/2014 | Schendel et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,670,281 | B2 | 6/2017 | Lim et al. |
| 9,732,392 | B2 | 8/2017 | Leonard et al. |
| 9,834,608 | B2 | 12/2017 | Lim et al. |
| 2013/0071414 | A1 | 3/2013 | Dotti et al. |
| 2013/0164277 | A1* | 6/2013 | Hyde ............. A61K 39/464838 435/7.1 |
| 2014/0023485 | A1 | 1/2014 | Michal |
| 2016/0264665 | A1 | 9/2016 | Lim et al. |
| 2017/0173180 | A1* | 6/2017 | Li .......................... A61K 35/17 |

(Continued)

FOREIGN PATENT DOCUMENTS

| | | |
|---|---|---|
| WO | 92/15322 A1 | 9/1992 |
| WO | 03/020763 A2 | 3/2003 |

(Continued)

OTHER PUBLICATIONS

Sadras et al ( Blood, 2919,v.134 abs 295.*
Barrio et al ( J of Immunol, 2013,v.191, pp. 3867-3875.*
Leenay, R., et al., Identifying and Visualizing Functional PAM Diversity across CRISPR-Cas Systems, Molecular Cell 62, Apr. 7, 2016, all enclosed pages cited.

(Continued)

*Primary Examiner* — Michail A Belyavskyi
(74) *Attorney, Agent, or Firm* — F. Brent Nix, Esq.; Johnson, Marcou, Isaacs & Nix, LLC

(57) ABSTRACT

Described herein are engineered antigen presenting cells that can be capable of modulating a target T-cell in a T-cell antigen specific manner. In some embodiments, the engineered APCs can include a modified antigen presentation pathway. Also described herein are methods of making and using the engineered antigen presenting cells.

18 Claims, 10 Drawing Sheets

Specification includes a Sequence Listing.

(56) References Cited

U.S. PATENT DOCUMENTS

| | | | |
|---|---|---|---|
| 2017/0233474 A1 | 8/2017 | Lim et al. | |
| 2018/0079812 A1 | 3/2018 | Lim et al. | |
| 2018/0208636 A1 | 7/2018 | Lim et al. | |
| 2018/0346589 A1 | 12/2018 | Ngo | |
| 2018/0355011 A1 | 12/2018 | Lim et al. | |
| 2019/0010240 A1* | 1/2019 | Stone | C07K 14/005 |
| 2019/0010245 A1 | 1/2019 | Ngo | |
| 2019/0134093 A1 | 5/2019 | Lim et al. | |
| 2019/0202918 A1 | 7/2019 | Lim et al. | |
| 2019/0269728 A1 | 9/2019 | Foot et al. | |
| 2019/0270991 A1 | 9/2019 | Foot et al. | |
| 2021/0230548 A1* | 7/2021 | Daher | C07K 16/2803 |
| 2021/0269771 A1* | 9/2021 | Barzel | C12N 5/0635 |
| 2022/0154219 A1* | 5/2022 | Green | A61K 39/39 |
| 2023/0081163 A1* | 3/2023 | Scholz | A61K 39/4622 |
| | | | 435/2 |

FOREIGN PATENT DOCUMENTS

| | | | |
|---|---|---|---|
| WO | 2004/033685 A1 | 4/2004 | |
| WO | 2004/044004 A2 | 5/2004 | |
| WO | 2004/074322 A1 | 9/2004 | |
| WO | 2005/113595 A2 | 12/2005 | |
| WO | 2005/114215 A2 | 12/2005 | |
| WO | 2006/000830 A2 | 1/2006 | |
| WO | 2006/125962 A2 | 11/2006 | |
| WO | 2008/038002 A2 | 4/2008 | |
| WO | 2008/039818 A2 | 4/2008 | |
| WO | 2011/146862 A1 | 11/2011 | |
| WO | 2012/079000 A1 | 6/2012 | |
| WO | 2013/022739 A1 | 2/2013 | |
| WO | 2013/039889 A1 | 3/2013 | |
| WO | 2013/040371 A2 | 3/2013 | |
| WO | 2013/166321 A1 | 11/2013 | |
| WO | 2014/011987 A1 | 1/2014 | |
| WO | 2014/018863 A1 | 1/2014 | |
| WO | 2014/083173 A1 | 6/2014 | |
| WO | 2014/093622 A2 | 6/2014 | |
| WO | 2014/134165 A1 | 9/2014 | |
| WO | 2014/204725 A1 | 12/2014 | |
| WO | 2016/106236 A1 | 6/2016 | |
| WO | 2016/138034 A1 | 9/2016 | |
| WO | 2017/193059 A1 | 11/2017 | |
| WO | 2018/017585 A1 | 1/2018 | |
| WO | 2018/039247 A1 | 3/2018 | |
| WO | 2018/081039 A1 | 5/2018 | |
| WO | 2018/213708 A1 | 11/2018 | |
| WO | 2018/213726 A1 | 11/2018 | |
| WO | 2018/222880 A1 | 12/2018 | |
| WO | 2019/005884 A1 | 1/2019 | |
| WO | 2019/005886 A1 | 1/2019 | |
| WO | 2019/010901 A1 | 1/2019 | |
| WO | 2019/016526 A1 | 1/2019 | |
| WO | 2019/018423 A1 | 1/2019 | |
| WO | 2019/019557 A1 | 1/2019 | |
| WO | 2019/060746 A1 | 3/2019 | |
| WO | 2019/071048 A1 | 4/2019 | |
| WO | 2019/084063 A1 | 5/2019 | |
| WO | 2019/126709 A1 | 6/2019 | |
| WO | 2019/126716 A1 | 6/2019 | |
| WO | 2019/126762 A2 | 6/2019 | |
| WO | 2019/141270 A1 | 7/2019 | |
| WO | 2019/166877 A1 | 9/2019 | |
| WO | 2019/175428 A1 | 9/2019 | |
| WO | 2019/178259 A2 | 9/2019 | |
| WO | 2019/195586 A1 | 10/2019 | |
| WO | 2020/033601 A1 | 2/2020 | |
| WO | 2020/131862 A1 | 6/2020 | |

OTHER PUBLICATIONS

Levy, Jonathan M., et al., "Cystosine and Adenine Base Editing of the Brain, Liver, Retina, Heart and Skeletal Muscle of Mice Via Adeno-Associated Viruses," Nature Biomedical Engineering, vol. 4, Jan. 2020, all enclosed pages cited.

Accapezzato, et al., "Chloroquine Enhances Human Cd8+ T Cell Responses Against Soluble Antigens in Vivo", Journal of Experimental Medicine, vol. 202, No. 6, Sep. 19, 2005, 817-828.

Alloatti, et al., "Toll-like Receptor 4 Engagement on Dendritic Cells Restrains Phago-Lysosome Fusion and Promotes Cross-Presentation of Antigens", Immunity, vol. 43, No. 6, Dec. 15, 2015, 1087-1100.

Anderson, et al., "Lag-3, Tim-3, and TIGIT: Co-inhibitory Receptors with Specialized Functions in Immune Regulation", Immunity, vol. 44, No. 5, May 17, 2016, 989-1004.

Anzalone, et al., "Search-and-replace Genome Editing Without Double-Strand Breaks or Donor DNA", Nature, vol. 576, No. 7785, Dec. 5, 2019, 30 pages.

Atschul, et al., "Basic Local Alignment Search Tool", Journal of Molecular Biology, vol. 215, 1990, 403-410.

Barber, et al., "Restoring Function in Exhausted CD8 T Cells During Chronic Viral Infection", Nature, vol. 439, No. 7077, Feb. 9, 2006, 682-687.

Besser, et al., "Clinical Responses in a Phase II Study Using Adoptive Transfer of Short-term Cultured Tumor Infiltration Lymphocytes in Metastatic Melanoma Patients", Clinical Cancer Research, vol. 16, No. 9, May 2010, 2646-2655.

Biswas, et al., "CRISPRTarget: Bioinformatic Prediction and Analysis of crRNA Targets", RNA Biology, vol. 10, No. 5, May 2013, 817-827.

Blander, J.M., "Regulation of the Cell Biology of Antigen Cross-Presentation", Annual Review of Immunology, vol. 36, Feb. 28, 2018, 717-753.

Brutkiewicz, Randy R., "Cell Signaling Pathways That Regulate Antigen Presentation", Journal of Immunology, vol. 197, No. 8, Jul. 8, 2016, 2971-2979.

Cebrian, et al., "Sec22B Regulates Phagosomal Maturation and Antigen Cross presentation by Dendritic Cells", Cell, vol. 147, No. 6, Dec. 9, 2011, 1355-1368.

Cella, et al., "Inflammatory Stimuli Induce Accumulation of MHC Class LI Complexes on Dendritic Cells", Nature, vol. 388, No. 6644, Aug. 1997, 782-787.

Challa-Malladi, et al., "Combined Genetic Inactivation of B2-microglobulin and Cd58 Reveals Frequent Escape from Immune Recognition in Diffuse Large B Cell Lymphoma", Cancer Cell, vol. 20, No. 6, Dec. 13, 2011, 728-740.

Chatterjee, et al., "Internalization and Endosomal Degradation of Receptor-bound Antigens Regulate the Efficiency of Cross Presentation by Human Dendritic Cells", Blood, vol. 120, No. 10, Sep. 6, 2012, 2011-2020.

Cheung, et al., "Connexons and Pannexons: Newcomers in Neurophysiology", Frontiers in Cellular Neuroscience, vol. 8, Article 348, Nov. 2014, 19 pages.

Cox, et al., "RNA Editing with CRISPR-Cas13", Science, vol. 358, No. 6366, Oct. 25, 2017, 15 pages.

Dance, Amber, "Core Concept: Cells Nibble one Another via the Under-appreciated Process of Trogocytosis", Proceedings of the National Academy of Sciences of the United States of America, vol. 116, No. 36, Sep. 3, 2019, 17608-17610.

Daringer, et al., "Modular Extracellular Sensor Architecture for Engineering Mammalian Cell-based Devices", ACS Synthetic Biology, vol. 3, 2014, 892-902.

Di Stasi, et al., "Inducible Apoptosis as a Safety Switch for Adoptive Cell Therapy", The New England Journal of Medicine, vol. 365, No. 18, Nov. 3, 2011, 16 pages.

Doench, et al., "Optimized sgRNA Design to Maximize Activity and Minimize Off-Target Effects of CRISPR-Cas9", Nature Biotechnology, vol. 34, No. 2, Feb. 2016, 35 pages.

Donepudi, et al., "Insights into the Regulatory Mechanism for Caspase-8 Activation", Molecular Cell, vol. 11, Feb. 2003, 543-549.

Dudley, et al., "Adoptive Cell Transfer Therapy Following Non-Myeloablative but Lymphodepleting Chemotherapy for the Treatment of Patients With Refractory Metastatic Melanoma", Journal of Clinical Oncology, vol. 23, No. 10, Apr. 2005, 2346-2357.

(56) References Cited

OTHER PUBLICATIONS

Dudley, et al., "Cancer Regression and Autoimmunity in Patients After Clonal Repopulation with Antitumor Lymphocytes", Science, vol. 298, No. 55494, Nov. 2002, 10 pages.
Eberl, et al., "The Functional Half-life of H-2Kd-Restricted T Cell Epitopes on Living Cells", European Journal of Immunology, vol. 26, No. 9, Sep. 1996, 1993-1999.
Embgenbroich, et al., "Current Concepts of Antigen Cross-Presentation", Molecular Mechanisms of Cross- Presentation, vol. 9, No. 1643, Jul. 2018, 10 pages.
Engel, et al., "CD Nomenclature 2015: Human Leukocyte Differentiation Antigen Workshops as a Driving Force in Immunology", The Journal of Immunology, vol. 195, 2015, 4555-4563.
Entzminger, et al., "De Novo Design of Antibody Complementarity Determining Regions Binding a FLAD Tetra-peptide", Scientific Reports, vol. 7, No. 10295, Aug. 31, 2017, 11 pages.
Esvelt, et al., "Orthogonal Cas9 Proteins for RNA-guided Gene Regulation and Editing", Nature Methods, vol. 10, No. 11, Nov. 2013, 19 pages.
Fourcade, et al., "PD-1 and Tim-3 Regulate the Expansion of Tumor Antigen-Specific CD8+ T Cells Induced by Melanoma Vaccines", Cancer Research, vol. 74, Issue 4, Dec. 16, 2013, 1045-1055.
Gao, et al., "Engineered Cpf1 Enzymes with Altered PAM Specificities", Nature Biotechnology, vol. 35, No. 8, Dec. 4, 2016, 17 pages.
Garrod, et al., "Dissecting T Cell Contraction In Vivo Using a Genetically Encoded Reporter of Apoptosis", Cell Reports, vol. 2, Nov. 29, 2012, 16 pages.
Gaudelli, et al., "Programmable Base Editing of A·T to G·C in Genomic DNA without DNA Cleavage", Nature, vol. 551, No. 7681, Nov. 23, 2017, 37 pages.
Giodini, et al., "Receptor-mediated Phagocytosis Elicits Cross-presentation in Nonprofessional Antigen-presenting Cells", Proceedings of the National Academy of Sciences of the United States of America, vol. 106, No. 9, Mar. 3, 2009, 3324-3329.
Gleditzsch, et al., "PAM Identification by CRISPR-Cas Effector Complexes: Diversified Mechanisms and Structures", RNA Biology, vol. 16. No. 4, 2019, 504-517.
Greco, et al., "Improving the Safety of Cell Therapy with the TK-Suicide Gene", Frontiers in Pharmacology, vol. 6, No. 95, May 5, 2015, 13 pages.
Grissa, et al., "CRISPRFinder: A Web Tool to Identify Clustered Regularly Interspaced Short Palindromic Repeats", Nucleic Acids Research, vol. 35, 2007, W52-W57.
Hamid, et al., "Safety and Tumor Responses with Lambrolizumab (Anti-PD-1) in Melanoma", The New England Journal of Medicine, vol. 369, No. 2, Jul. 11, 2013, 134-144.
Herve, et al., "Gap-junction-mediated Cell-to-cell Communication", Cell and Tissue Research, vol. 352, No. 1, Apr. 2013, 21-31.
Hodi, et al., "Improved Survival with Ipilimumab in Patients with Metastatic Melanoma", The New England Journal of Medicine, vol. 363, No. 8, Aug. 19, 2010, 711-723.
Hoffman, et al., "B Cells, Antibodies, and More", Clinical Journal of the American Society of Nephrology, vol. 11, No. 1, Jan. 2015, 18 pages.
Hudrisier, et al., "Capture of Target Cell Membrane Components via Trogocytosis is Triggered by a Selected Set of Surface Molecules on T or B Cells", The Journal of Immunology, vol. 178, 2007, 3637-3647.
Ikeda, et al., "Dual Effects of TRAIL in Suppression of Autoimmunity: The Inhibition of Th1 Cells and the Promotion of Regulatory T Cells", Journal of Immunology, vol. 185, No. 9, Nov. 1, 2010, 5259-5267.
Irvine, et al., "A Receptor for all Occasions", Cell, vol. 164, Issue 4, Feb. 11, 2016, 599-600.
Jensen, et al., "Design and Implementation of Adoptive Therapy with Chimeric Antigen Receptor-modified T Cells", Immunological Reviews, vol. 257, No. 1, 2014, 127-144.
Jiang, et al., "RNA-Guided Editing of Bacterial Genomes Using CRISPR-Cas Systems", Nature Biotechnology, vol. 31, No. 3, Mar. 2013, 233-239.
Johnson, et al., "Engineering of Primary Human B cells with CRISPR/Cas9 Targeted Nuclease", Scientific Reports, vol. 8, No. 12144, Aug. 14, 2018, 9 pages.
Johnson, et al., "Gene Therapy with Human and Mouse T-Cell Receptors Mediates Cancer Regression and Targets Normal Tissues Expressing Cognate Antigen", Blood, vol. 114, No. 3, Jul. 16, 2009, 535-546.
Johnston, et al., "The Immunoreceptor TIGIT Regulates Antitumor and Antiviral CD8+ T Cell Effector Function", Cancer Cell, vol. 26, Dec. 8, 2014, 923-937.
Joly, et al., "What is Trogocytosis and What is its Purpose?", Nature Immunology, vol. 4, No. 9, Sep. 2003, 815 page.
Joung, et al., "Genome-Scale Crispr-Cas9 Knockout and Transcriptional Activation Screening", Nature Protocols, vol. 12, No. 4, Apr. 2017, 71 pages.
Kalos, et al., "T Cells with Chimeric Antigen Receptors Have Potent Antitumor Effects and can Establish Memory in Patients with Advanced Leukemia", Science Translational Medicine, vol. 3, No. 95, Aug. 2011, 21 pages.
Kleinstiver, et al., "Engineered Crispr-Cas9 Nucleases with Altered Pam Specificities", Nature, vol. 523, No. 7561, Jul. 23, 2015, 17 pages.
Klompe, et al., "Transposon-encoded CRISPR-Cas Systems Direct RNA-guided DNA Integration", Nature, vol. 571, Jul. 11, 2019, 24 pages.
Komor, et al., "Programmable Editing of a Target Base in Genomic DNA without Double-Stranded DNA Cleavage", Nature, vol. 533, No. 7603, May 19, 2016, 25 pages.
Koonin, et al., "Origins and Evolution of CRISPR-Cas Systems", Philosophical Transactions of the Royal Society of London, vol. 374, Issue 1772, Oct. 24, 2018, 16 pages.
Leach, et al., "Enhancement of Antitumor Immunity by CTLA-4 Blockade", Science, vol. 271, Issue 5256, Mar. 22, 1996, 1734-1736.
Li, et al., "Base Editing with a Cpf1-Cytidine Deaminase Fusion", Nature Biotechnology, vol. 36, No. 4, Apr. 2018, 8 pages.
Linsley, et al., "Human B7-1 (CD80) and B7-2 (CD86) Bind with Similar Avidities but Distinct Kinetics to CD28 and CTLA-4 Receptors", Immunity, vol. 1, No. 9, Dec. 1, 1994, 793-801.
Linterman, et al., "T Follicular Helper Cells During Immunity and Tolerance", Progress in Molecular Biology and Translational Science, vol. 92, 2010, 207-248.
Liu, et al., "Engineering Cell Signaling Using Tunable CRISPR-Cpf1-based Transcription Factors", Nature Communications, vol. 8, No. 2095, Dec. 13, 2017, 8 pages.
Mahoney, et al., "Combination Cancer Immunotherapy and New Immunomodulatory Targets", Nature Reviews Drug Discovery, vol. 14, Jul. 31, 2015, 561-584.
Makarova, et al., "Evolutionary Classification of CRISPR-Cas Systems: A Burst of Class 2 and Derived Variants", Nature Reviews Microbiology, vol. 18, Feb. 2020, 67-83.
Marraffini, et al., "Self Vs. Non-Self Discrimination During CRISPR RNA-Directed Immunity", Nature, vol. 463, No. 7280, Jan. 28, 2010, 13 pages.
Masuda, et al., "Possible Implication of Fcγ Receptor-Mediated Trogocytosis in Susceptibility to Systemic Autoimmune Disease", Hindawi Publishing Corporation Clinical and Developmental Immunology, vol. 2013, Article 345745, Aug. 2, 2013, 7 pages.
Maus, et al., "Adoptive Immunotherapy for Cancer or Viruses", Annual Review of Immunology, vol. 32, Jan. 9, 2014, 46 pages.
Mojica, et al., "Short Motif Sequences Determine the Targets of the Prokaryotic CRISPR Defence System", Microbiology, vol. 155, 2009, 733-740.
Morgan, et al., "Cancer Regression in Patients After Transfer of Genetically Engineered Lymphocytes", Science, vol. 314, No. 5796, Nov. 2006, 126-129.
Morsut, et al., "Engineering Customized Cell Sensing and Response Behaviors Using Synthetic Notch Receptors", Cell, vol. 164, No. 4, Feb. 11, 2016, 780-791.

(56) References Cited

OTHER PUBLICATIONS

Nair-Gupta, et al., "TLR Signals Induce Phagosomal Mhc-i Delivery from the Endosomal Recycling Compartment to Allow Cross-presentation", Cell, vol. 158, No. 3, Jul. 31, 2014, 506-521.

Nishida, et al., "Targeted Nucleotide Editing Using Hybrid Prokaryotic and Vertebrate Adaptive Immune Systems", Science, vol. 353, No. 6305, Sep. 16, 2016, 10 pages.

Nishimasu, et al., "Crystal Structure of Cas9 in Complex with Guide RNA and Target DNA", Cell, vol. 156, No. 5, Feb. 27, 2014, 25 pages.

Onabajo, et al., "Actin-Binding Protein 1 Regulates B Cell Receptor-Mediated Antigen Processing and Presentation in Response to B Cell Receptor Activation", The Journal of Immunology, vol. 180, 2008, 6685-6695.

Pardoll, Drewm., "The Blockade of Immune Checkpoints in Cancer Immunotherapy", Nature Reviews Cancer, vol. 12, Mar. 22, 2012, 252-264.

Parnas, et al., "A Genome-Wide CRISPR Screen in Primary Immune Cells to Dissect Regulatory Networks", Cell, vol. 162, No. 3, Jul. 30, 2015, 24 pages.

Pattanayak, et al., "High-Throughput Profiling of Off-Target DNA Cleavage Reveals RNA-Programmed Cas9 Nuclease Specificity", Nature biotechnology, vol. 31, No. 9, Sep. 2013, 16 pages.

Peters, et al., "Recruitment of CRISPR-Cas Systems by Tn7-Like Transposons", Proceedings of the National Academy of Sciences, vol. 114, No. 35, 2017, E7358-E7366.

Poirot, et al., "Multiplex Genome-Edited T-cell Manufacturing Platform for "Off-the-Shelf" Adoptive T-cell Immunotherapies", Cancer Research, vol. 75, Issue 18, Sep. 2015, 13 pages.

Qui, et al., "Mutation Detection Using Surveyor Nuclease", Biotechniques, vol. 36, No. 4, 2004, 702-707.

Ramos, et al., "An Inducible Caspase 9 Suicide Gene to Improve the Safety of Mesenchymal Stromal Cell Therapies". Stem Cells, vol. 28, No. 6, Jun. 8, 2010, 16 pages.

Ran, et al., "Double Nicking by RNA-Guided CRISPR Cas9 for Enhanced Genome Editing Specificity", Cell, vol. 154, No. 6, Sep. 12, 2013, 19 pages.

Rees, et al., "Base Editing: Precision Chemistry on The Genome and Transcriptome of Living Cells", Nature Reviews Genetics, vol. 19, No. 12, Dec. 2018, 41 pages.

Rescigno, et al., "Bacteria-induced Neo-biosynthesis, Stabilization, and Surface Expression of Functional Class I Molecules in Mouse Dendritic Cells", Proceedings of the National Academy of Sciences of the United States of America, vol. 95, Apr. 1998, 5229-5234.

Restifo, et al., "Adoptive Immunotherapy for Cancer: Harnessing the T Cell Response", Nature Reviews Immunology, vol. 12, No. 4, Apr. 1, 2012, 30 pages.

Robert, et al., "Ipilimumab Plus Dacarbazine for Previously Untreated Metastatic Melanoma", The New England Journal of Medicine, vol. 364, Jun. 30, 2011, 2517-2526.

Rosenberg, et al., "Adoptive Cell Transfer as Personalized Immunotherapy for Human Cancer", Science, vol. 348, No. 6230, Apr. 2015, 19 pages.

Roybal, et al., "Engineering T Cells with Customized Therapeutic Response Programs Using Synthetic Notch Receptors", Cell, vol. 167, No. 2, Oct. 6, 2016, 31 pages.

Roybal, et al., "Precision Tumor Recognition by T Cells With Combinatorial Antigen-Sensing Circuits", Cell, vol. 164, No. 4, Feb. 11, 2016, 11 pages.

Sadelain, Michael, "Eliminating Cells Gone Astray", The New England Journal of Medicine, vol. 365, Nov. 3, 2011, 1735-1737.

Sakuishi, et al., "Targeting Tim-3 and PD-1 Pathways to Reverse T cell Exhaustion and Restore Anti-Tumor Immunity", Journal of Experimental Medicine, vol. 207, No. 10, Sep. 2010, 2187-2194.

Samie, et al., "The Transcription Factor tfeb Acts as a Molecular Switch that Regulates Exogenous Antigen-presentation Pathways", Nature Immunology, vol. 16, No. 7, Jul. 2015, 21 pages.

Schwarz, et al., "Rewiring Human Cellular Input-output Using Modular Extracellular Sensors", Nature Chemical Biology, vol. 13, No. 2, Feb. 2017, 202-209.

Shalem, et al., "Genome-Scale CRISPR-Cas9 Knockout Screening in Human Cells", Science, vol. 343, No. 6166, Jan. 3, 2014, 10 pages.

Shifrut, et al., "Genome-wide CRISPR Screens in Primary Human T Cells Reveal Key Regulators of Immune Function", Cell, vol. 175, Dec. 13, 2018, 29 pages.

Shmakov, et al., "Discovery and Functional Characterization of Diverse Class 2 CRISPR-Cas Systems", Molecular Cell, vol. 60, No. 3, Nov. 5, 2015, 385-397.

Strecker, et al., "RNA-Guided DNA Insertion with CRISPR-Associated Transposes", Science, 10/1126/science.aax9181, 2019, 12 pages.

Su, et al., "Efficient Culture of Human Naive and Memory B Cells for Use as APCs", The Journal of Immunology, vol. 197, Oct. 10, 2016, 4163-4176.

Suda, et al., "Membrane Fas Ligand Kills Human Peripheral Blood T Lymphocytes, and Soluble Fas Ligand Blocks the Killing", Journal of Experimental Medicine, vol. 186, No. 12, Dec. 15, 1997, 2045-2050.

Suzuki, et al., "In Vivo Genome Editing via CRISPR/Cas9 Mediated Homology-Independent Targeted Integration", Nature, vol. 540, Dec. 2016, 24 pages.

Topalian, et al., "Safety, Activity, and Immune Correlates of Anti-PD-1 Antibody in Cancer", New England Journal of Medicine, vol. 366, No. 26, Jun. 5, 2012, 12 pages.

Vanhove, et al., "Antagonist Anti-CD28 Therapeutics for the Treatment of Autoimmune Disorders", Antibodies, vol. 6, No. 4, 2017, 14 pages.

Walsh, et al., "Humanized Mouse Models of Clinical Disease", Annual Review of Pathology: Mechanisms of Disease, vol. 12, Jan. 24, 2017, 35 pages.

Watson, et al., "SHP-1: The Next Checkpoint Target for Cancer Immunotherapy?", Biochemical Society Transactions, vol. 44, No. 2, Apr. 15, 2016, 356-362.

Wherry, et al., "Molecular and Cellular Insights into T Cell Exhaustion", Nature Reviews Immunology, vol. 15, No. 8, Aug. 2015, 29 pages.

Wherry, Johne., "T Cell Exhaustion", Nature Immunology, vol. 12, No. 6, Jun. 2011, 492-499.

Wolchok, et al., "Nivolumab plus Ipilimumab in Advanced Melanoma", The New England Journal of Medicine, vol. 369, No. 2, Jul. 11, 2013, 122-133.

Woo, et al., "Immune Inhibitory Molecules LAG-3 and PD-1 Synergistically Regulate T-cell Function to Promote Tumoral Immune Escape", Cancer Research, vol. 72, No. 4, Feb. 15, 2012, 917-927.

Wu, et al., "Genetic Engineering in Primary Human B Cells with Crispr-cas9 Ribonucleoproteins", Journal of Immunological Methods, vol. 457, Jun. 2018, 18 pages.

Zetche, et al., "A Split Cas9 Architecture for Inducible Genome Editing and Transcription Modulation", Nature Biotechnology, vol. 33, No. 2, Feb. 2015, 6 pages.

Zetsche, et al., "Cpf1 is a Single RNA-Guided Endonuclease of a Class 2 CRISPR-Cas System", Cell, vol. 163, No. 3, Oct. 22, 2015, 759-771.

Zhang, et al., "Transmembrane Tnf-α Promotes Activation-induced Cell Death by Forward and Reverse Signaling", Oncotarget, vol. 8, No. 38, 2017, 63799-63812.

Zhou, et al., "Cd14+ Blood Monocytes can Differentiate into Functionally Mature Cd83+ Dendritic Cells", Proceedings of the National Academy of Sciences of the United States of America, vol. 93, No. 6, Mar. 1996, 2588-2592.

Zhou, et al., "Long-Term Outcome after Haploidentical Stem Cell Transplant and Infusion of T Cells Expressing the Inducible Caspase 9 Safety Transgene", Blood, vol. 123, No. 25, Jun. 19, 2014, 3895-3905.

\* cited by examiner

| Cell Type | Number | Reported frequency in b.c. | Number expected | Purity |
|---|---|---|---|---|
| Monocytes | ~40 mio cells (1 b.c.) | 10.7±2.8% | ~100 mio cells | n.d. |
| Pan T Cells | ~140 mio cells (1/3 b.c.) | 53.8±6.1% | ~166 mio cells | n.d. |
| Pan B Cells | ~25 mio cells (2/3 b.c.) | 7.2±2.4% | ~47 mio cells | 83.5% |

SEQUENCE LISTING

```
<160> NUMBER OF SEQ ID NOS: 19

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 10
<212> TYPE: PRT
<213> ORGANISM: Simian virus 40

<400> SEQUENCE: 2

Pro Lys Lys Lys Arg Lys Val Glu Ala Ser
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic nucleoplasmin bipartite NLS

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 9
<212> TYPE: PRT
<213> ORGANISM: Homo sapiens
```

<400> SEQUENCE: 4

Pro Ala Ala Lys Arg Val Lys Leu Asp
1               5

<210> SEQ ID NO 5
<211> LENGTH: 11
<212> TYPE: PRT
<213> ORGANISM: Homo sapiens

<400> SEQUENCE: 5

Arg Gln Arg Arg Asn Glu Leu Lys Arg Ser Pro
1               5                   10

<210> SEQ ID NO 6
<211> LENGTH: 38
<212> TYPE: PRT
<213> ORGANISM: Homo sapiens

<400> SEQUENCE: 6

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 7
<211> LENGTH: 42
<212> TYPE: PRT
<213> ORGANISM: Homo sapiens

<400> SEQUENCE: 7

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 8
<211> LENGTH: 8
<212> TYPE: PRT
<213> ORGANISM: Homo sapiens

<400> SEQUENCE: 8

Val Ser Arg Lys Arg Pro Arg Pro
1               5

<210> SEQ ID NO 9
<211> LENGTH: 8
<212> TYPE: PRT
<213> ORGANISM: Homo sapiens

<400> SEQUENCE: 9

Pro Pro Lys Lys Ala Arg Glu Asp
1               5

<210> SEQ ID NO 10
<211> LENGTH: 8
<212> TYPE: PRT
<213> ORGANISM: Homo sapiens

```
<400> SEQUENCE: 10

Pro Gln Pro Lys Lys Pro Leu
1               5

<210> SEQ ID NO 11
<211> LENGTH: 12
<212> TYPE: PRT
<213> ORGANISM: Mus sp.

<400> SEQUENCE: 11

Ser Ala Leu Ile Lys Lys Lys Lys Lys Met Ala Pro
1               5                   10

<210> SEQ ID NO 12
<211> LENGTH: 5
<212> TYPE: PRT
<213> ORGANISM: Influenza virus

<400> SEQUENCE: 12

Asp Arg Leu Arg Arg
1               5

<210> SEQ ID NO 13
<211> LENGTH: 7
<212> TYPE: PRT
<213> ORGANISM: Influenza virus

<400> SEQUENCE: 13

Pro Lys Gln Lys Lys Arg Lys
1               5

<210> SEQ ID NO 14
<211> LENGTH: 10
<212> TYPE: PRT
<213> ORGANISM: Hepatitis D virus

<400> SEQUENCE: 14

Arg Lys Leu Lys Lys Lys Ile Lys Lys Leu
1               5                   10

<210> SEQ ID NO 15
<211> LENGTH: 10
<212> TYPE: PRT
<213> ORGANISM: Mus sp.

<400> SEQUENCE: 15

Arg Glu Lys Lys Lys Phe Leu Lys Arg Arg
1               5                   10

<210> SEQ ID NO 16
<211> LENGTH: 20
<212> TYPE: PRT
<213> ORGANISM: Homo sapiens

<400> SEQUENCE: 16

Lys Arg Lys Gly Asp Glu Val Asp Gly Val Asp Glu Val Ala Lys Lys
1               5                   10                  15

Lys Ser Lys Lys
            20

<210> SEQ ID NO 17
<211> LENGTH: 17
<212> TYPE: PRT
<213> ORGANISM: Homo sapiens
```

```
<400> SEQUENCE: 17

Arg Lys Cys Leu Gln Ala Gly Met Asn Leu Glu Ala Arg Lys Thr Lys
1               5                   10                  15

Lys

<210> SEQ ID NO 18
<211> LENGTH: 15
<212> TYPE: PRT
<213> ORGANISM: Artificial Sequence
<220> FEATURE:
<223> OTHER INFORMATION: Synthetic Linker

<400> SEQUENCE: 18

Gly Gly Gly Gly Gly Gly Gly Gly Gly Gly Gly Gly Gly Gly Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic GlySer Linker

<400> SEQUENCE: 19

Gly Gly Gly Gly Ser Gly Gly Gly Gly Ser Gly Gly Gly Gly Ser
1               5                   10                  15
```

ENGINEERED ANTIGEN PRESENTING CELLS AND USES THEREOF

CROSS-REFERENCE TO RELATED APPLICATIONS

This application claims the benefit of U.S. Provisional Application No. 62/933,016, filed Nov. 8, 2019. The entire contents of the above-identified applications are hereby fully incorporated herein by reference.

STATEMENT REGARDING FEDERALLY SPONSORED RESEARCH

This invention was made with government support under Grant No. HL141201 awarded by National Institutes of Health. The government has certain rights in the invention.

REFERENCE TO AN ELECTRONIC SEQUENCE LISTING

The contents of the electronic sequence listing ("BROD-4730US_ST25.txt", Size is 4,111 bytes and it was created on Nov. 9, 2020), is herein incorporated by reference in its entirety.

TECHNICAL FIELD

The subject matter disclosed herein is generally directed to engineered immune cells, and more particularly, engineered antigen presenting cells.

BACKGROUND

T lymphocytes, or simply T cells, are lymphocytes that develop in the thymus gland and play key roles in immune regulation and response. More recently, engineered T cells have been developed that have specific targeting and effector functions, such as CAR T cells. Given the vast roles T cells play in immune response and regulation, aberrant T cell function and/or regulation can lead to disease, and fine-tuned manipulation of T cell function and/or response can provide benefits.

Efforts to modulate T-cell function and response have been largely focused on traditional therapeutic modalities such as small molecule pharmaceuticals and biologics (e.g. antibodies). More recent efforts have been directed at directly modifying T-cells to equip them with specific effector functions. Traditional pharmaceutical agents suffer from side-effects due to non-specificity. Although biologics are generally more specific, they too suffer from off-target side effects. Both suffer from a limited ability to fine tune T cell effector response. Modified T-cells, such as CAR-T cells, offer more options to provide T cells with particular effector functions, but do not do much in the way of modulating native T-cell populations.

As such, there exists a need for compositions and techniques that are capable of modulating e.g. effector, regulator, and other functions of T-cells, particularly those that are part of a native population or engineered T-cell population in circulation in a subject.

Citation or identification of any document in this application is not an admission that such a document is available as prior art to the present invention.

SUMMARY

Described in certain example embodiments herein are engineered antigen presenting cells comprising a modified antigen presentation pathway capable of interacting with one or more target T-cells in an antigen-specific fashion; and inducible or constitutive expression of one or more T-cell modulating agents capable of modulating target T-cell activity upon interaction of the engineered antigen presenting cell and the target T-cell.

In certain example embodiments, the engineered antigen presenting cell is an engineered professional antigen presenting cell. In some example embodiments, the engineered antigen presenting cell is an engineered B cell, engineered macrophage, engineered monocyte, or engineered dendritic cell.

In certain example embodiments, the modified antigen presentation pathway is capable of processing and presenting an antigen such that the engineered antigen presenting cell is capable of antigen-specific binding and/or interaction with the one or more target T-cells. In some example embodiments, the modified antigen presentation pathway comprises one or more modified cross-presentation pathway genes. In some example embodiments, the engineered antigen presenting cell overexpresses one or more genes in the cross-presentation pathway, underexpresses one or more genes in the cross-presentation pathway, lacks one or more genes in the cross-presentation pathway, or a combination thereof. In some example embodiments, the engineered antigen presenting cell has increased MHC I extracellular antigen presentation relative to an unmodified antigen presenting cell.

In certain example embodiments, the engineered antigen presenting cell is capable of being loaded with an extracellular antigen.

In certain example embodiments, the engineered antigen presenting cell expresses an engineered B cell receptor capable of specifically interacting with an epitope tag that is coupled to a peptide or polypeptide extracellular antigen. In some example embodiments, the epitope tag is a FLAG tag, His-tag, or a Myc-tag.

In certain example embodiments, the engineered antigen presenting cell is capable of producing an intracellular antigen.

In certain example embodiments, the antigen is a target T-cell antigen. In some example embodiments, one or more target T-cells are CD8+ T-cells, CD4+ T-cells, CD25+ T-cells, an engineered T-cell particularly a CAR T-cell. In some example embodiments, the T-cell is a non-pathogenic T-cell, a pathogenic T-cell or an autoreactive T-cell.

In certain example embodiments, the T-cell modulating agent is capable of eliminating or inhibiting one or more functions of the target T-cell and/or a cell within effective proximity of the target T-cell or activating one or more functions of the target T-cell and/or a cell within effective proximity of the target T-cell. In some example embodiments, the one or more T-cell modulating agents are immune checkpoint molecules. In some example embodiments, the immune checkpoint molecules are inhibitory checkpoint molecules. In some example embodiments, the inhibitory checkpoint molecules are AA2AR, B7-H3, B7-H4, BTLA, CTLA-4, IDO, KIR, LAG3, NOX2, PD1, TIM-3, VISTA, SIGLEC7. In some example embodiments, the immune checkpoint molecules are stimulatory checkpoint molecules. In some example embodiments, the stimulatory checkpoint molecules are CD27, CD28, CD40, CD122, CD137, OX40, GITR, ICOS.

In certain example embodiments, one or more T-cell modulating agents are capable of inducing T-cell death. In some example embodiments, the one or more T-cell modulating agents are capable of binding a death receptor on the T-cell. In some example embodiments, the one or more T-cell modulating agents are selected from the group consisting of: TNF, CD95L (FasL or Fas ligand), TRAIL, TL1A, IL-2, a CD-28 inhibitor, and combinations thereof.

In certain example embodiments, the engineered antigen presenting cell further comprises a SynNotch receptor and/or MESA receptor and expression or activation of the one or more T-cell modulating agents is induced by activation of the SynNotch receptor and/or MESA receptor.

In certain example embodiments, the engineered antigen presenting cell further comprises a hemichannel, capable of forming a gap junction between the engineered antigen presenting cell and a hemichannel present on the target T-cell.

In certain example embodiments, the engineered antigen presenting cell further comprises a trogocytic inducer, wherein the trogocytic inducer is capable of being expressed the surface of the engineered cell.

In certain example embodiments, the engineered antigen presenting cell is derived from one or more antigen presenting cells isolated from a subject.

In certain example embodiments, the engineered cell is capable of self-inactivation or suicide.

In certain example embodiments, described herein are pharmaceutical formulations comprising: an engineered antigen presenting cell as described herein and a pharmaceutically acceptable carrier.

In certain example embodiments, described herein are methods of modulating an immune response comprising, administering an engineered antigen presenting cell as described herein or a pharmaceutical formulation thereof to a subject in need thereof. In some example embodiments, the subject in need thereof has a disease or a symptom thereof. In some example embodiments, the disease is an autoimmune disease. In some example embodiments, the disease is cancer.

In certain example embodiments, the subject in need thereof has received or will be receiving a vaccine.

In certain example embodiments, described herein are methods comprising co-administering an engineered antigen presenting cell as described herein or a pharmaceutical formulation thereof and a second therapeutic, preventative, or a pharmaceutical formulation thereof. In some example embodiments, the subject in need thereof has a disease or a symptom thereof. In some example embodiments, the disease is cancer or an autoimmune disease.

In certain example embodiments, the engineered antigen presenting cell is effective to modulate one or more therapeutic effect, preventative effect, side-effect, or a combination thereof of the second therapeutic, preventative, or a pharmaceutical formulation thereof.

In certain example embodiments, the engineered antigen presenting cell is effective to reduce the side-effect of the second therapeutic, preventative, or a pharmaceutical formulation thereof.

In certain example embodiments, the engineered antigen presenting cell is effective to increase a therapeutic and/or preventative effect of the second therapeutic, preventative, or a pharmaceutical formulation thereof.

Described in certain example embodiments herein are methods of making an engineered antigen presenting cell comprising: (a) modifying an antigen presentation pathway of an antigen presenting cell capable of interacting with one or more target T-cells in an antigen-specific fashion to produce the engineered antigen presenting cell; and (b) optionally exposing the engineered antigen presenting cell to an extracellular target T-cell antigen and/or (c) optionally modifying the engineered antigen presenting cell to render it capable of producing an intracellular target T-cell antigen.

In certain example embodiments, the engineered antigen presenting cell is capable of expressing an MHC I molecule, MHC II molecule, or both.

In certain example embodiments, exposing the engineered antigen presenting cell to an extracellular target T-cell antigen occurs ex vivo or in vitro.

In certain example embodiments, the target T-cell antigen is a peptide or a polypeptide.

In certain example embodiments, the antigen presenting cell is an immune cell.

In certain example embodiments, the antigen presenting cell is a B cell, macrophage, monocyte, or dendritic cell.

In certain example embodiments, the method further comprises culturing the engineered antigen presenting cell in the presence of one or more diseased cells isolated from a subject and wherein the one or more diseased cells is/are optionally expanded. In some example embodiments, the one or more diseased cells are cancer cells.

In certain example embodiments, modification of the antigen presenting pathway comprises increasing incorporation and/or presentation of an extracellular antigen by an MHC I molecule.

In certain example embodiments, modifying the antigen presentation pathway comprises modifying one or more genes in a cross-presentation pathway. In some example embodiments, modifying one or more genes in the cross-presentation pathway comprises overexpressing one or more genes in the cross-presentation pathway, under expressing one or more genes in the cross-presentation pathway, or silencing expression of one or more genes in the cross-presentation pathway, or a combination thereof. In some example embodiments, modifying the antigen presentation pathway comprises renders the cell capable of self-inactivation or suicide.

In certain example embodiments, optionally modifying the polynucleotide(s) is effective to render the engineered antigen presenting cell capable of internalizing an extracellular antigen.

In certain example embodiments, modifying the antigen presenting cell renders the antigen presenting cell capable of binding or otherwise interacting with the extracellular antigen to facilitate its uptake into the antigen presenting cell.

In certain example embodiments, the method further comprises modifying the engineered antigen presenting cell to provide inducible or constitutive expression of one or more T-cell modulating molecules capable of modulating target T-cell activity upon activation of the engineered antigen presenting cell and the target T-cell. In some example embodiments, the T-cell modulating agent is capable of eliminating or inhibiting one or more functions of the target T-cell or activating one or more functions of the target T-cell. In some example embodiments, the one or more T-cell modulating molecules are immune checkpoint molecules. In some example embodiments, the immune checkpoint molecules are inhibitory checkpoint molecules. In some example embodiments, the inhibitory checkpoint molecules are AA2AR, B7-H3, B7-H4, BTLA, CTLA-4, IDO, KIR, LAG3, NOX2, PD1, TIM-3, VISTA, SIGLEC7. In some example embodiments, the immune checkpoint molecules are stimulatory checkpoint molecules. In some example embodiments, the stimulatory checkpoint molecules are CD27, CD28, CD40, CD122, CD137, OX40, GITR, ICOS.

In certain example embodiments, the one or more T-cell modulating agents are capable of inducing T-cell death. In some example embodiments, the one or more T-cell modulating agents are selected from the group consisting of: TNF, CD95L (FasL or Fas ligand), TRAIL, TL1A, IL-2, a CD-28 inhibitor, and combinations thereof.

In certain example embodiments, the engineered antigen presenting cell is further modified to comprise SynNotch receptor and/or MESA receptor and expression or activation of the one or more T-cell modulating agents is induced by activation of the SynNotch receptor and/or MESA receptor.

In certain example embodiments, the method further comprises modifying the engineered antigen presenting cell to deliver one or more cargo molecules to the target T-cells upon interaction between the modified antigen presenting cell and the target T-cell.

In certain example embodiments, antigen is produced endogenously by the engineered antigen presenting cell.

In some example embodiments, the antigen is exogenously loaded into the engineered antigen presenting cell.

In certain example embodiments, the antigen presenting cell is further comprising an antigen receptor capable of binding or otherwise interacting with the antigen to facilitate uptake of the antigen into the engineered antigen presenting cell.

In certain example embodiments, the engineered antigen presenting cell further comprises a hemichannel capable of forming a gap junction between the engineered cell and a hemichannel present on the target T-cell.

In certain example embodiments, the engineered antigen presenting cell is further modified to comprise a trogocytic inducer capable of expression on the surface of the engineered antigen presenting cell.

In certain example embodiments, the method further comprises isolating one or more antigen presenting cells from a subject prior to performing step (a).

In certain example embodiments, the method further comprises delivering the engineered cell to a subject after performing steps (a) and optionally (b) and/or (c).

In certain example embodiments, the subject from which the antigen presenting cells are isolated is the same subject to which they are delivered after performing steps (a) and optionally (b) and/or (c).

In certain example embodiments, the intracellular and/or extracellular target T-cell antigen is a pathogenic T-cell antigen.

In certain example embodiments, the intracellular and/or extracellular target T-cell antigen is an autoreactive T-cell antigen.

In certain example embodiments, the intracellular and/or extracellular target T-cell antigen is an exogenous non-pathogenic target T-cell antigen.

Described in certain example embodiments herein are methods of screening an antigen presenting cell comprising: (a) expressing a Cas protein in an antigen presenting cell (APC) or APC cell population; (b) expressing one or more guide molecules capable of targeting one or more target genes in the APC and are effective to result in the loss of function of the one or more target genes; and (c) screening one or more phenotypes of the APC after (a) and (b).

In certain example embodiments, screening comprises performing a gene expression analysis on one or more genes of the APC.

In certain example embodiments, the one or more target genes are selected from: LAMP2, PSMB8, TAP1, TAP2, ERAP1, CANX, CALR, TAPBP, PDIA3, CD74, HLA-DMA, HLA-DMB, HLA-DOA, TAPBPL, B2M, ERAP2, HLA-A, HLA-B, HLA-C, HLA-E, HLA-F, HLA-G, TLR4, MYD88, TICAM1, LNPEP, TFEB, RAB27A, SEC61A1, RAB3A, RAB3B, BCAP31, EEA1, LAMP1, RAB4A, RAB5A, RAB11A, RAB7A, RHOB, PKN1, PIK3C3, TF, WASF1, DIAPH1, SYK, ICAM1, a lysosomal protease gene involved antigen degradation (e.g. Cathepsins L, S, D, and/or B), a gene that encodes a protein involved in pH maintenance of an APC, V-aTPase, NOX2, a gene encoding an endocytosis receptor, GILT, AAA, ATPase p97, Sec61, TAP, ERAP, IRAP, a SNARE gene (e.g. Sec22b and syntaxin 4, SNAP23, UNC93B1, MAPK, MAPKKK, MAPKK, p38, INK, ERK1/2, MMK3, MKK6, protein kinase C family members (e.g. PKC alpha, beta (both I and II), atypical PKC ζ, and λ/ι, and novel (δ, ε, and θ), toll-like receptors (e.g. TLR-1, TLR2, TLR-4, TLR-5, TLR7, and TLR9), INF-gamma, IL-4, TNF-alpha, JAK, STAT (e.g. STAT3), Rho GTPases, Rho kinase, and any combination thereof.

In certain example embodiments, the APC is a B cell, macrophage, monocyte, or dendritic cell.

Described in certain example embodiments herein are engineered antigen presenting cells comprising a modified antigen presentation pathway capable of interacting with one or more target T-cells in an antigen-specific fashion; and inducible or constitutive expression of one or more T-cell modulating agents capable of modulating target T-cell activity upon interaction of the engineered antigen presenting cell and a target T-cell of the one or more the target T-cells.

In certain example embodiments, the engineered antigen presenting cell is an engineered professional antigen presenting cell.

In certain example embodiments, the engineered antigen presenting cell is an engineered B cell, engineered macrophage, engineered monocyte, or engineered dendritic cell.

In certain example embodiments, the modified antigen presentation pathway is capable of processing and presenting a T-cell antigen such that the engineered antigen presenting cell is capable of antigen-specific binding, antigen-specific interaction, or both with the one or more target T-cells.

In certain example embodiments, the modified antigen presentation pathway comprises one or more modified cross-presentation pathway genes.

In certain example embodiments, the engineered cell overexpresses one or more genes in the cross-presentation pathway, underexpresses one or more genes in the cross-presentation pathway, lacks one or more genes in the cross-presentation pathway, or a combination thereof.

In certain example embodiments, the engineered antigen presenting cell has increased MHC I extracellular antigen presentation relative to an unmodified antigen presenting cell.

In certain example embodiments, the engineered antigen presenting cell is capable of being loaded with an extracellular T-cell antigen.

In certain example embodiments, the engineered antigen presenting cell expresses an engineered B cell receptor capable of specifically interacting with an epitope tag that is coupled to a peptide or polypeptide extracellular T-cell antigen.

In certain example embodiments, the engineered antigen presenting cell is capable of producing an intracellular T-cell antigen.

In certain example embodiments, the T-cell modulating agent is a. capable of eliminating or inhibiting one or more functions of the target T-cell, a cell within effective proximity of the target T-cell, or both; or b. capable of activating one or more functions of the target T-cell, a cell within effective proximity of the target T-cell, or both.

In certain example embodiments, the one or more T-cell modulating agents are a. immune checkpoint molecule(s); b. agent(s) capable of binding a death receptor on the target T-cell c. agent(s) capable of inducing target T-cell death; or d. any combination thereof.

In certain example embodiments, the antigen presenting cell further comprises a SynNotch receptor, a MESA receptor, or both, wherein expression or activation of the one or more T-cell modulating agents is induced by activation of the SynNotch receptor, the MESA receptor, or both.

In certain example embodiments, the antigen presenting cell further comprises a hemichannel capable of forming a gap junction between the engineered antigen presenting cell and a hemichannel present on the target T-cell.

In certain example embodiments, the antigen presenting cell further comprises a trogocytic inducer, wherein the trogocytic inducer is capable of being expressed the surface of the engineered cell.

Described in certain example embodiments herein are pharmaceutical formulations comprising an antigen presenting cell or population thereof, such as any of those of the present description herein, and a pharmaceutically acceptable carrier.

Described in certain example embodiments herein are methods of modulating an immune response in a subject in need thereof comprising administering an engineered antigen presenting cell or population thereof, such as any of those of the present description herein, or a pharmaceutical formulation thereof to the subject in need thereof.

In certain example embodiments, wherein the subject in need thereof a. has an autoimmune disease; b. has a cancer; c. has received or will be receiving a vaccine; or d. any combination thereof.

In certain example embodiments, the method further comprises administering a second therapeutic agent, second preventative agent, or a pharmaceutical formulation thereof to the subject in need thereof.

In certain example embodiments, the engineered antigen presenting cell is effective to modulate one or more therapeutic effects, preventative effects, side-effects, or a combination thereof of the second therapeutic agent, second preventative agent, or the pharmaceutical formulation thereof.

Described in certain example embodiments herein are methods of making an engineered antigen presenting cell comprising: a. modifying an antigen presentation pathway of an antigen presenting cell thereby rendering it capable of interacting with one or more target T-cells in an antigen-specific fashion to produce the engineered antigen presenting cell; and b. optionally exposing the engineered antigen presenting cell to an extracellular target T-cell antigen in vitro or ex vivo; c. optionally modifying the engineered antigen presenting cell to render it capable of producing an intracellular target T-cell antigen; or d. any combination thereof.

In certain example embodiments, the engineered antigen presenting cell is capable of expressing an MHC I molecule, MHC II molecule, or both.

In certain example embodiments, the extracellular target T-cell or intracellular target T-cell antigen is a peptide or a polypeptide.

In certain example embodiments, the antigen presenting cell is a B cell, a macrophage, a monocyte, or a dendritic cell.

In certain example embodiments, the method further comprises culturing the engineered antigen presenting cell in the presence of one or more diseased cells isolated from a subject and wherein the one or more diseased cells is/are optionally expanded.

In certain example embodiments, modifying the antigen presenting pathway comprises increasing incorporation of, presentation of, or both of an extracellular antigen by an MHC I molecule.

In certain example embodiments, modifying the antigen presentation pathway comprises modifying one or more genes in a cross-presentation pathway, wherein modifying one or more genes comprises in the cross-presentation pathway comprises a. overexpressing one or more genes in the cross-presentation pathway; b. underexpressing one or more genes in the cross-presentation pathway; c. deleting one or more genes in the cross-presentation pathway; d. silencing expression of one or more genes in the cross-presentation pathway; or e. any combination thereof.

In certain example embodiments, modifying the antigen presentation pathway is effective to render the engineered antigen presenting cell capable of internalizing an extracellular target T-cell antigen.

In certain example embodiments, the method further comprises modifying the engineered antigen presenting cell to comprise inducible or constitutive expression of one or more T-cell modulating agents, wherein the one or more T-cell modulating agents is/are capable of modulating target T-cell activity upon interaction of the engineered antigen presenting cell and the target T-cell.

In certain example embodiments, the one or more T-cell modulating agents is/are capable of eliminating or inhibiting one or more functions of the target T-cell, activating one or more functions of the target T-cell, inducing target T-cell death, or a combination thereof.

In certain example embodiments, the one or more of the one or more T-cell modulating agents are immune checkpoint molecules.

In certain example embodiments, the method further comprises modifying the engineered antigen presenting cell such that it comprises a SynNotch receptor, a MESA receptor, or both and wherein the SynNotch receptor, MESA receptor, or both are capable of inducing expression or activation of the one or more T-cell modulating agents.

In certain example embodiments, the method further comprises modifying the engineered antigen presenting cell such that the engineered antigen presenting cell is capable of delivering one or more cargo molecules to the target T-cell upon interaction between the modified engineered antigen presenting cell and the target T-cell.

In certain example embodiments, the cargo molecule is a. produced endogenously by the engineered antigen presenting cell; b. exogenously loaded into the engineered antigen presenting cell; or c. both.

In certain example embodiments, the cargo is a target T-cell antigen.

In certain example embodiments, the method further comprises modifying the antigen presenting cell such that the engineered antigen presenting cell comprises a receptor capable of binding or otherwise interacting with an extracellular cargo molecule and facilitating uptake of the extracellular cargo into the engineered antigen presenting cell.

In certain example embodiments, the receptor is an engineered B cell receptor capable of specifically interacting with an epitope tag that is coupled to a peptide or polypeptide extracellular cargo.

In certain example embodiments, the peptide or polypeptide extracellular cargo is a target T-cell antigen.

In certain example embodiments, the engineered antigen presenting cell further comprises a hemichannel capable of forming a gap junction between the engineered cell and a hemichannel present on the target T-cell.

In certain example embodiments, the method further comprises modifying the engineered antigen presenting cell such that it comprises a trogocytic inducer capable of expression on the surface of the engineered antigen presenting cell.

These and other embodiments, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

(FIG. 2A) to and graphs (FIGS. 2B-2C) demonstrating knock-out efficiency in the CCL156 cells by a CRISPR-Cas9 system.

FIG. 5 can more broadly demonstrate development of antibodies or fragments thereof capable of detecting specific MHC-antigen complexes on the surface of the engineered antigen presenting cells herein.

FIGS. 8A-8C—Isolation using MACS of primary cells from buffy coat of peripheral blood. Monocytes were selected using positive selection with CD14 beads. Pan T-cells and Pan B cells were negatively selected for.

Figure 1:
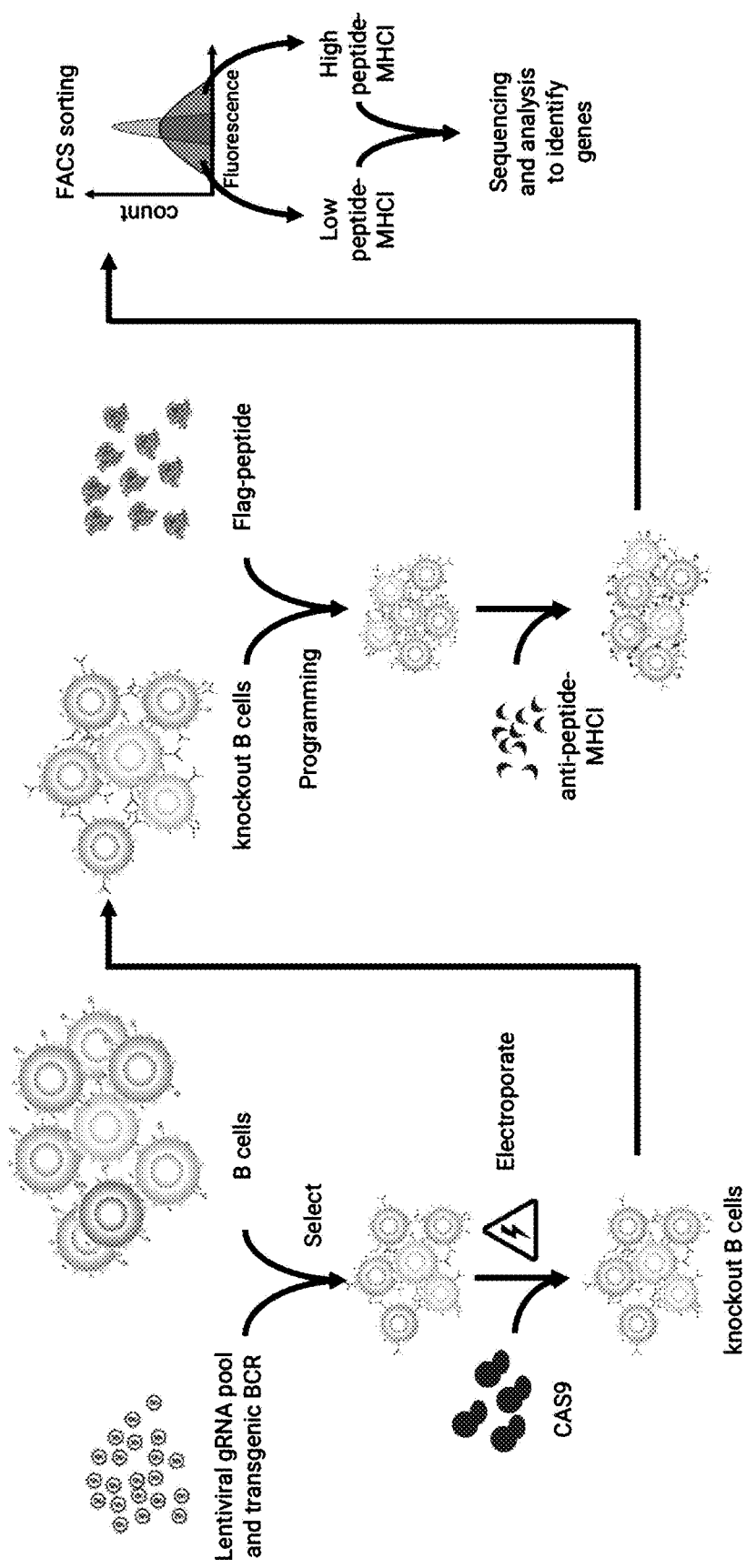
FIG. 1—A strategy for generating and screening engineered antigen presenting cells (e.g. engineered B-cells) having a desired presentation of an antigen and/or to determine cross-presentation of antigen by the B cell or screen for B cells expression a desired antigen presenting pathway (e.g. a cross-presentation pathway). In some embodiments, one or more genes in the antigen presenting pathway (e.g. cross-presentation pathway) are modulated using a suitable genetic engineering technique (e.g. a CRISPR-Cas system). In some embodiments, the B-cells can be engineered to express a recombinant B-cell receptor via a suitable technique (e.g. lentiviral vector mediated expression). In some embodiments, the recombinant B cell-receptor can be specific to a known antigen, e.g. a FLAG molecule to which a target T-cell antigen can be attached, which can facilitate loading of the target T-cell antigen into the B cell. B cells expressing the desired antigen presentation pathway can be screened by measuring the expression of MHC I-peptide (antigen) and/or MHC II-peptide (antigen) complexes by the engineered B cell.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al.

(eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader embodiments discussed herein. One embodiment described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

T-cells play vast roles in immune response and regulation. T-cell dysfunction can lead to various immune diseases and disorders and can facilitate and perpetuate the development and maintenance of cancers. Engineered T-cells have been developed that have specific targeting and effector functions, such as CAR T-cells. Although modified T-cells, such as CAR-T-cells, offer more options to provide T-cells with particular effector functions, they still fall short of providing a tool for modulating native T-cell populations.

With at least these failures of current T-cell technologies in mind, embodiments disclosed herein provide engineered antigen presenting cells that can have a modified antigen presentation pathway capable of interacting with one or more target T-cells in an antigen specific fashion; and inducible or constitutive expression of one or more T-cell modulating agents capable of modulating target T-cell activity upon interaction of the engineered antigen presenting cell and the target T-cell. In some exemplary embodiments, the modified engineered antigen presenting cell is an engineered B cell.

Embodiments disclosed herein, provided modified antigen presentation pathways. In some embodiments, the MHC I restricted presentation pathway is modified, the MHCI II restricted presentation pathway is modified, a cross-presentation pathway is modified, or any combination thereof is modified. In some embodiments, the engineered APCs can have one or more antigen processing pathway gene modified. In some embodiments, that one or more antigen processing pathway gene that is/are modified is/are modified such that the expression of that gene is increased and/or the expression and/or activity of the respective gene product(s) is/are increased. In some embodiments, one or more antigen processing pathway gene that is/are modified is/are modified such that the expression of that gene is decreased and/or the expression and/or activity of the respective gene product(s) is/are decreased.

Embodiments disclosed provided pharmaceutical formulations that can include the engineered APCs. The engineered APCs or component thereof can be included in a formulation that can be delivered to a subject or cell. In some embodiments, the formulation is a pharmaceutical formulation. One or more of the polypeptides, polynucleotides, vectors, cells, and combinations thereof described herein can be provided to a subject in need thereof or a cell alone or as an active ingredient, such as in a pharmaceutical formulation. As such, also described herein are pharmaceutical formulations containing an amount of one or more of the polypeptides, polynucleotides, vectors, cells, and combinations thereof described herein. In some embodiments, the pharmaceutical formulation can contain an effective amount of the one or more of the polypeptides, polynucleotides, vectors, cells, and combinations thereof described herein.

Embodiments disclosed herein provide kits that contain one or more of the one or more of the polypeptides, polynucleotides, vectors, cells (e.g. engineered APCs), or other components described herein and combinations thereof and pharmaceutical formulations described herein. In embodiments, one or more of the polypeptides, polynucleotides, vectors, cells, and combinations thereof described herein can be presented as a combination kit.

Embodiments disclosed herein provide methods of making the engineered APCs described herein. In some the engineered APCs can be made by: (a) modifying an antigen presentation pathway of an antigen presenting cell capable of interacting with one or more target T-cells in an antigen-specific fashion to produce the engineered antigen presenting cell; and (b) optionally exposing the engineered antigen presenting cell to an extracellular target T-cell antigen and/or (c) optionally modifying the engineered antigen presenting cell to render it capable of producing an intracellular target T-cell antigen.

Embodiments disclosed herein provide methods of using the engineered antigen presenting cells to modulate an immune response in a subject to which they are administered. Modulating of the immune response can occur in some embodiments via modulation of one or more T-cell populations therein. In some embodiments, the engineered antigen presenting cells described herein can be used as a co-therapy, such as to further modify activity of an engineered T-cell, such as a CAR T-cell or a vaccine.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Engineered Antigen Presenting Cells

Described herein are engineered antigen presenting cells that can have a modified antigen presentation pathway capable of interacting with one or more target T-cells in an antigen specific fashion; and inducible or constitutive expression of one or more T-cell modulating agents capable of modulating target T-cell activity upon interaction of the engineered antigen presenting cell and the target T-cell. As is described elsewhere herein the engineered antigen presenting cells may be capable of modulating an immune response in a subject to which the engineered antigen presenting cells are administered via modulation of one or more T-cell populations therein. In some embodiments, the engineered antigen presenting cells described herein can be used as a co-therapy, such as to further modify activity of an engineered T-cell, such as a CAR T-cell. Further uses, embodiments, advantages, and features are described elsewhere herein and will be appreciated in view of this description.

In some embodiments, the engineered antigen presenting cell can express one or more major histocompatibility complex (MHC) molecules. In some embodiments, the engineered APC can express MHC I, MHC II, or both types of MHC molecules. Where an APC expresses only one type of MHC (e.g. MHC I or MHCII), the APC can be engineered to express the other type. For example, if the APC only expresses MHC I molecules, it can be engineered to express a MHC II molecule. It will be appreciated that the term of art "professional antigen presenting cell" refers to antigen presenting cells that express both MHC I and MHC II molecules. The MHC class I molecule is a heterodimer composed of a 46-kDa heavy chain which is non-covalently associated with the 12-kDa light chain β-2 microglobulin. In humans, there are several MHC alleles, such as, for example, HLA-A2, HLA-A1, HLA-A3, HLA-A24, HLA-A28, HLA-A31, HLA-A33, HLA-A34, HLA-B7, HLA-B45 and HLA-Cw8. The sequences of MHC alleles are known and can be found, for example, at the IMGT/HLA database available at www.ebi.ac.uk/ipd/imgt/hla. In some embodiments, the MHC class I allele is an HLA-A2 allele, which in some populations is expressed by approximately 50% of the population. In some embodiments, the HLA-A2 allele can be an HLA-A*0201, *0202, *0203, *0206, or *0207 gene product. In some cases, there can be differences in the frequency of subtypes between different populations. For example, in some embodiments, more than 95% of the HLA-A2 positive Caucasian population is HLA-A*0201, whereas in the Chinese population the frequency has been reported to be approximately 23% HLA-A*0201, 45% HLA-A*0207, 8% HLA-A*0206 and 23% HLA-A*0203. MHC class II proteins are expressed in a subset of nucleated vertebrate cells, generally called antigen presenting cells (APCs). In humans, there are several MHC class II alleles, such as, for example, DR1, DR3, DR4, DR7, DR52, DQ1, DQ2, DQ4, DQ8 and DP1. In some embodiments, the MHC class II allele that is HLA-DRB1*0101, an HLA-DRB*0301, HLA-DRB*0701, HLA-DRB*0401 an HLA-DQB1*0201. The sequences of MHC alleles are known and can be found, for example, at the IMGT/HLA database available at www.ebi.ac.uk/ipd/imgt/hla.

In certain example embodiments, the engineered APCs may be engineered to have a modified antigen presentation and/or processing pathway such that the presentation and/or processing of an antigen (either intracellular or extracellular) is modified as compared to a non-modified control APC. For example, and as further described below, a MHC I restricted presentation pathway, a MHC II restricted presentation pathway, or a cross-presentation pathway may be modified such that the manner in which the engineered APC presents an antigen is modified relative to a wild type APC. In some embodiments, the antigen presentation and/or processing pathway that is modified is the cross-presentation pathway.

As is described in greater detail elsewhere herein the engineered APCs can be loaded with an extracellular antigen and/or engineered to express intracellularly a heterologous antigen. As used in this context, "heterologous" refers to antigens that are not native to the engineered APC and not necessarily heterologous to the subject from which the APC is derived or engineered from. Thus, an autoantigen recognized by a T-cell that is from the same subject as the APC from which the engineered APC is derived would be considered "heterologous" in this context. The heterologous antigen can be processed and presented in an MHC molecule by antigen processing and presentation pathways native to the APC and/or engineered as described elsewhere herein. The antigen-MHC complex that can be expressed by the engineered APC can be capable of being recognized and/or interact with a T-cell receptor (TCR) on a target T-cell.

In some embodiments, the engineered APC can be functionalized such that the APC is capable of modulating a function, activity, and/or characteristic of a target T-cell with which it interacts in an antigen specific manner. By modulating a function, activity, and/or characteristic of a target T-cell, the immune system can be modulated by the engineered APC. In some embodiments, the engineered APC can induce death of a target T-cell with which it interacts in an antigen specific manner.

In some embodiments, the engineered APC or population thereof can be programmed to interact with a target T-cell or a population thereof. This is described in greater detail elsewhere herein. In some of these embodiments, an APC or an engineered APC that has not been exposed to an antigen or antigen source can be exposed to an antigen or antigen source. In these embodiments, an antigen or antigen source can refer to a peptide, a polypeptide, a cell, a tissue, or other potential source of material. Generally, the antigen or antigen source is one that target T-cells are reactive to and may comprise multiple antigens that are T-cell reactive. In this way populations of engineered APCs can be generated that display, via MHC molecules, a heterogenous collection of antigens to which the target T-cell population is reactive. Optionally, one or more specific engineered APCs with a specific target T-cell antigen presented in one or more MHC complexes can be selected out of the population.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Th$\alpha\beta$, CD4+, CD8+, CD 25+, effector Th, memory Th, regulatory Th, CD4+/CD8+ thymocytes, CD4−/CD8− thymocytes, $\gamma\delta$ T-cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

Engineered Antigen Presenting Cells

Described herein are engineered antigen presenting cells that can have a modified antigen presentation pathway capable of interacting with one or more target T-cells in an antigen specific fashion; and inducible or constitutive expression of one or more T-cell modulating target T-cell activity upon interaction of the engineered antigen presenting cell and the target T-cell.

The antigen presenting cell (APC) can be at any stage of differentiation or any activation stage. The term "antigen-presenting cell" as used throughout this specification denotes any of a variety of cells capable of acquiring, processing, presenting, or displaying at least one antigen or antigenic fragment on (or at) its cell surface. In general, the term "antigen-presenting cell" can be any cell that aids the enhancement of an immune response or immune tolerance (e.g., from the T-cell or B-cell arms of the immune system) to an antigen or antigenic composition. Native antigen presenting cells are cells that are capable of displaying or presenting an antigen normally or preferentially with a class II major histocompatibility molecule or complex to an immune cell. APC may for example refer to professional APC, such as macrophages, B cells, or dendritic cells. The engineered antigen-presenting cells described herein can be engineered macrophages, engineered B cells, engineered dendritic cells, or engineered monocytes. The engineered antigen presenting cells described herein can express or be engineered to express an MHC I molecule, an MHC II molecule, or both.

As is described in greater detail elsewhere herein, in some embodiments, engineered APCs can have a modified antigen presentation pathway that can increase or decrease processing and/or presentation of an antigen into an MHC I molecule as compared to an MHC II molecule. The engineered APCs can have a modified antigen presentation pathway that can increase or decrease processing and/or presentation of an antigen into an MHC II molecule as compared to an MHC I molecule.

As is described in greater detail elsewhere herein the engineered APCs can be loaded with an extracellular and/or engineered to express intracellularly a heterologous antigen. As used in this context, "heterologous" refers to antigens that are not native to the engineered APC and not necessarily heterologous to the subject from which the APC is derived or engineered from. Thus, an autoantigen recognized by a T-cell that is from the same subject as the APC from which the engineered APC is derived would be considered "heterologous" in this context. The heterologous antigen can be processed and presented in an MHC molecule by antigen processing and presentation pathways native to the APC and/or engineered as described elsewhere herein. The antigen-MHC complex that can be expressed by the engineered APC can be capable of being recognized and/or interact with a T-cell receptor (TCR) on a target T-cell.

Thus, in some embodiments, the engineered APC can express an MHC-antigen complex. In some embodiments, the antigen is specific to a target T-cell. In some embodiments, the antigen is a heterologous antigen as the term is used in context with the engineered APC as previously described. In some embodiments, the APC expresses one or more MHC I-antigen complexes, one or more MHC II-antigen complexes, or both. In some embodiments, the antigen is an intracellular antigen that is expressed inside the engineered APC as is discussed elsewhere herein. In some embodiments, the antigen is an extracellular antigen that is "loaded" into the APC.

In some embodiments, the engineered APC can be functionalized such that the APC is capable of modulating a function, activity, and/or characteristic of a target T-cell with which it interacts in an antigen specific manner. By modulating a function, activity, and/or characteristic of a target T-cell, the immune system can be modulated by the engineered APC. In some embodiments, the engineered APC can induce death of a target T-cell with which it interacts in an antigen specific manner.

In some embodiments, the engineered APC or population thereof can be programmed to interact with a target T-cell or a population thereof. This is described in greater detail elsewhere herein. In some of these embodiments, an APC or an engineered APC that has not been exposed to an antigen or antigen source can be exposed to an antigen or antigen source. In these embodiments, an antigen or antigen source can refer to a peptide, a polypeptide, a cell, a tissue, or other potential source of material. Generally, the antigen or antigen source is one where target T-cells are reactive to. In this way a population of engineered APCs with a heterogenous collection of target T-cell antigens presented in MHC molecules across the population of APCs. Optionally one or more specific engineered APCs with a specific target T-cell antigen presented in one or more MHC complexes can be selected out of the population.

In some embodiments, the engineered APC can be engineered to express a modified B cell receptor (BCR). The modified BCR can be engineered to recognize a suitable marker peptide that can be incorporated into an antigen. Suitable marker peptides can include short peptides such as FLAG, His, etc. This can increase the efficiency of loading a peptide or polypeptide antigen into an engineered APC via the engineered BCR.

It will be appreciated that suitable genetic engineered methods and techniques will be known by one of ordinary skill in the art to make such modifications as described herein.

Characterization of APCs and Engineered APCs

Cells such as immune cells and/or engineered APCs as disclosed herein can, in the context of the present specification, be said to "comprise the expression," or conversely, to "not express" one or more markers, such as one or more genes or gene products; or be described as "positive" or conversely as "negative" for one or more markers, such as one or more genes or gene products; or be said to "comprise" a defined "gene or gene product signature".

By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

The term "marker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more embodiments of the tested object's phenotype and/or genotype. The terms "marker" and "biomarker" may be used interchangeably throughout this specification.

Preferably, markers as intended herein may be peptide-, polypeptide- and/or protein-based, or may be nucleic acid-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or copy DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

In some embodiments, the marker is composed of a signature (such as a gene signature) or profile. As used herein a signature may encompass any gene or genes, or protein or proteins, whose expression profile or whose occurrence is associated with a specific cell type, subtype, or cell state of a specific cell type or subtype within a population of cells. Increased or decreased expression or activity or prevalence may be compared between differenT-cells in order to characterize or identify for instance specific cell (sub)populations. A gene signature as used herein, may thus refer to any set of up- and down-regulated genes between differenT-cells or cell (sub)populations derived from a gene-expression profile. For example, a gene signature may comprise a list of genes differentially expressed in a distinction of interest. It is to be understood that also when referring to proteins (e.g. differentially expressed proteins), such may fall within the definition of "gene" signature.

The signatures as defined herein (being it a gene signature, protein signature or other genetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of immune cells that are linked to particular pathological condition (e.g. cancer), or linked to a particular outcome or progression of the disease, or linked to a particular response to treatment of the disease.

The signature according to certain embodiments of the present invention may comprise or consist of one or more genes and/or proteins, such as for instance 1, 2, 3, 4, 5, 6, 7, 8, 9, 10 or more. In certain embodiments, the signature may comprise or consist of two or more genes and/or proteins, such as for instance 2, 3, 4, 5, 6, 7, 8, 9, 10 or more. In certain embodiments, the signature may comprise or consist of three or more genes and/or proteins, such as for instance 3, 4, 5, 6, 7, 8, 9, 10 or more. In certain embodiments, the signature may comprise or consist of four or more genes and/or proteins, such as for instance 4, 5, 6, 7, 8, 9, 10 or more. In certain embodiments, the signature may comprise or consist of five or more genes and/or proteins, such as for instance 5, 6, 7, 8, 9, 10 or more. In certain embodiments, the signature may comprise or consist of six or more genes and/or proteins, such as for instance 6, 7, 8, 9, 10 or more. In certain embodiments, the signature may comprise or consist of seven or more genes and/or proteins, such as for instance 7, 8, 9, 10 or more. In certain embodiments, the signature may comprise or consist of eight or more genes and/or proteins, such as for instance 8, 9, 10 or more. In certain embodiments, the signature may comprise or consist of nine or more genes and/or proteins, such as for instance 9, 10 or more. In certain embodiments, the signature may comprise or consist of ten or more genes and/or proteins, such as for instance 10, 11, 12, 13, 14, 15, or more. It is to be understood that a signature according to the invention may for instance also include a combination of genes or proteins.

It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins may be differentially expressed on a single cell level or may be differentially expressed on a cell population level. Preferably, the differentially expressed genes/proteins as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein of the signature, such as for instance at least to, at least three, at least four, at least five, at least six, or all genes/proteins of the signature.

Signatures may be functionally validated as being uniquely associated with a particular immune phenotype. Induction or suppression of a particular signature may consequentially be associated with or causally drive a particular immune phenotype.

Various embodiments and embodiments of the invention may involve analyzing gene signatures, protein signature, and/or other genetic signature based on single cell analyses (e.g. single cell RNA sequencing) or alternatively based on cell population analyses, as is defined herein elsewhere.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "nucleic acid" as used throughout this specification typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and 0-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-O,4'-C-alkylene-linked, e.g., 2'-O,4'-C-methylene-linked or 2'-O,4'-C-ethylene-linked sugars such as ribose; 2'-fluoroarabinose, etc.). Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone internucleoside linkages. Preferably, internucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof. A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

A marker, for example a gene or gene product, for example a peptide, polypeptide, protein, or nucleic acid, or a group of two or more markers, is "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

Depending on factors that can be evaluated and decided on by a skilled person, such as inter alia the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

Markers can be measured quantitatively or qualitatively (e.g. a relative quantity). An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed for example as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of markers in a tested object (e.g., in or on a cell, cell population, tissue, organ, or organism, e.g., in a biological sample of a subject).

In certain embodiments, such methods may include biochemical assay methods, including inter alia assays of enzymatic activity, membrane channel activity, substance-binding activity, gene regulatory activity, or cell signalling activity of a marker, e.g., peptide, polypeptide, protein, or nucleic acid.

In other examples, such methods may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In further examples, such methods may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; and APPI-(MS)$^n$. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other examples, such methods may include chromatography methods. The term "chromatography" encompasses methods for separating substances, such as chemical or biological substances, e.g., markers, such as preferably peptides, polypeptides, or proteins, referred to as such and vastly available in the art. In a preferred approach, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

Further techniques for separating, detecting and/or quantifying markers, such as preferably peptides, polypeptides, or proteins, may be used, optionally in conjunction with any of the above described analysis methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

[In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridisation-based analysis, microarray expression analysis, digital gene expression profiling (DGE), RNA-in-situ hybridisation (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed. To do so, special microfluidic devices have been developed to encapsulate each cell in an individual drop, associate the RNA of each cell with a 'cell barcode' unique to thaT-cell/drop, measure the expression level of each RNA with sequencing, and then use the cell barcodes to determine which cell each RNA molecule came from. In particular, methods of Macosko et al. (Cell. 2015, vol. 161, 1202-1214) and Klein et al. (Cell. 2015, vol. 161, 1187-1201) are contemplated for the present invention.

Engineered B-Cells

In some embodiments, the engineered APC cell is an engineered B cell. The engineered B cell can be derived and/or engineered from a B cell that is isolated at any stage, see e.g. FIG. 10A. In some embodiments, the engineered B cell is derived and/or engineered form a B cell that is isolated from the blood. In some embodiments, the engineered B cell is derived and/or engineered form a B cell that is isolated from the peripheral blood. In some embodiments, the engineered B cell is derived and/or engineered form a B cell that is isolated from the buffy coat of peripheral blood. In some embodiments, the engineered B cell is derived and/or engineered form a B cell that is isolated from the bone marrow. As used herein, "B cell" refers to any number of a diverse population of similar types of white blood cell. B cells may be recognised, for example, by function, by phenotype and/or by gene expression pattern, particularly by cell surface phenotype. B cells can be professional antigen presenting cells, which can express both MHC I and MHC II molecules. B cells can also be identified by the expression of a Pre-B cell Receptor or a B cell receptor. In some embodiments, the B cell expresses a B cell receptor. In some embodiments, a B cell can be identified by its ability to secrete antibodies.

Figure 10A:
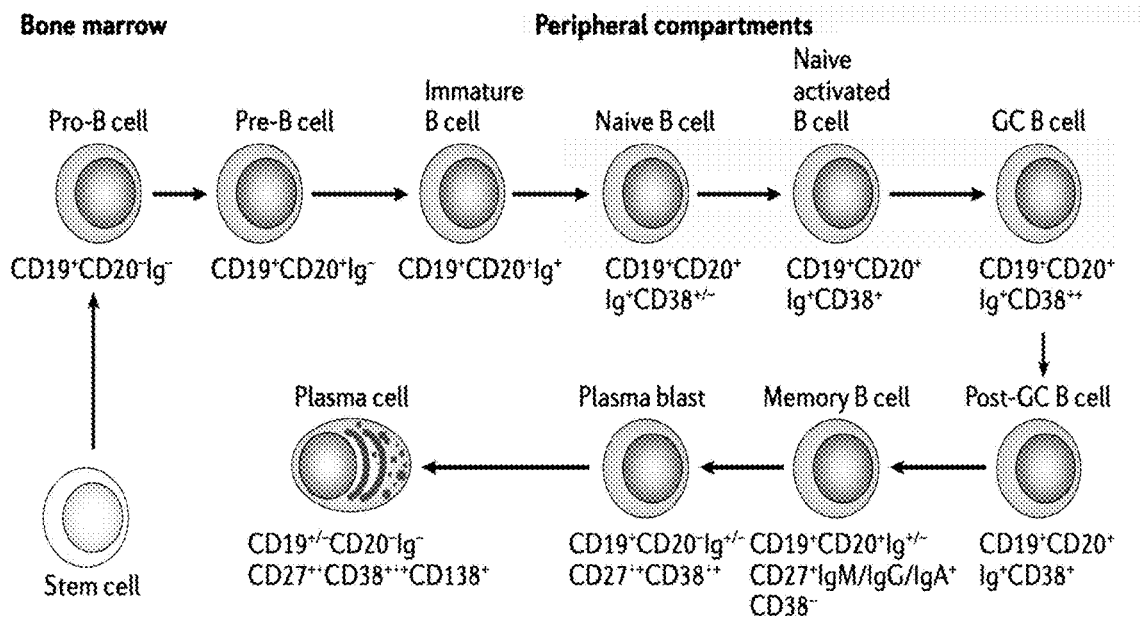
FIGS. 10A-10B—Maturation of B cells from stem cell to plasma cell (FIG. 10A) and amount of naïve B cells, classical memory B cells, plasma cells, and double negative memory B cells in the live B cell population as a percentage of live CD19 positive cells over time (FIG. 10B).

As shown in FIG. 10A, B cell development starts in the bone marrow. Immature B cells migrate to the spleen to mature. There are three main subsets of mature naïve B cells: Follicular B2 cells, marginal zone B2 cells, and B1 cells. See also Hoffman et al., 2016. Clin J. Am Soc. Nephrol. 11(1): 137-154. After exposure to an antigen, B cells can become activated and differentiate into antibody-producing plasma cells. Mature follicular B2 cells can migrate through blood and lymph, reside in specific B cell areas of lymph nodes, Peyer's patches, and the spleen. Mature B2 cells can terminally differentiate into plasma B cells (or more simply "plasma cells") and Memory B cells. Marginal zone B2 cells reside in the marginal sinus of the spleen and mediate the transport of antigen in immune complexes. B1 cells are involved in the development of IgM responses to bacterial T-cell independent antigens. These cells can migrate from the peritoneum and reside in the mesenteric lymph nodes.

Activation of B cells can occur via antigen recognition by B cell receptors and a co-stimulatory, secondary activation signal. Activation can stimulate B cell proliferation and the formation of germinal centers where B cell differentiation into plasma cells or memory B cells can occur. In vivo, plasma cells can be found in the spleen and lymph nodes and can produce and secrete different classes of antibodies, which can be clonally unique. Following a primary response, a small number of plasma cells can develop into memory B cells, which can survive for a long period of time and can enable a rapid secondary response.

In some embodiments, the engineered B cell can be generated from an activated or inactivated B cell. In some embodiments, the engineered B cell can be generated from a B2 lineage B cell. In some embodiments, the B2 lineage B cell is a follicular B2 lineage B cell. In some embodiments, the B2 lineage B cell is a marginal zone B2 lineage cell. In some embodiments, the engineered B cell can be a mature B2 lineage B cell. In some embodiments, the engineered B cell can be generated from a B1 lineage B cell. In some embodiments, the engineered B cell can be generated from a mature B1 lineage B cell. In some embodiments, the engineered B cell can be generated from an activated B cell. In some embodiments, the engineered B cell can be generated from an inactive B cell. In some embodiments, the engineered B cell can be generated from a memory B cell, plasma cell, or plasma blast. In some embodiments, the engineered B cell can be generated from a B cell progenitor. In some embodiments, the engineered B cells are capable of producing antibodies. In some embodiments, the engineered B cell can be generated from and/or be capable of producing IgM antibodies, IgA antibodies, IgG antibodies, IgD antibodies, IgE antibodies, and combinations thereof. In some embodiments, the engineered B cell can be capable of producing IgM antibodies, IgA antibodies, IgG antibodies, IgD antibodies, IgE antibodies, and combinations thereof. In some embodiments, the engineered B cell can be generated from a B cell capable of antibody isotype switching. In some embodiments, the engineered B cell is capable of antibody isotype switching.

B cells can express a variety of markers that can be used to identify function, maturity, activation state, subset, etc. Such characterization is also referred to as immunophenotyping. The markers can also be used to isolate one or more B cells from a mixed population or sample. B cells can be said to be positive or negative for a particular marker with positive indicating that the B cell expresses such maker and negative indicating that the B cell does not express such marker. Furthermore, the level of expression of a given marker within a subtype can be indicated. For example, the marker can be said to be "high" (e.g. $CD24^{high}$), "mid", (e.g. $CD24^{mid}$), or "low" (e.g. $CD24^{low}$). Other nomenclature specifics relating to CD markers is discussed in Engle et al. 2016 J. Immunol. 195(10) 4555-4563. B cell surface markers can include, but are not limited to, CD1d, CD5, CD10, CD!9, CD20, CD21, CD22, CD23, CD24, CD25, CD27, CD30, CD34, CD38, CD40, CD43, CD45R, CD69, CD80, CD86, C1qR1/CD93, CD138, CD269, TL7R alpha/CD127, IL3R, IL4R, TL4R, BCMA, MHCII, CXCR4, CXCR5, CXCR7, CD117/ckit, IgD, IgM, IgA, IgG, IgE, and combinations thereof. Transcription factor B cell markers can include, but are not limited to Pax5/BSAP, EBF1, E2A, PU.1, Oct2, BCL6, BLIMP1, IRF4, XBP1, OBF1, SP-B, Flt-3/Flk-2, Sca-1/Ly6.

In some embodiments, progenitor B cells markers can be CD34, CD 117/ckit, Flt-3/Flk-2, IL7R/CD127, CD10, Pax5/BSAP, Sca-1/Ly6. In some embodiments, Pre-Pro B cells can be CD45R, C1qR1/CD93, CD19, CD24, CD34, CD38, CD43, CD117/c-kit, CXCR4, Flt-3/Flk-2, IL-7R alpha/CD127, Neprilysin/CD10, and Pax5/BSAP. In some embodiments, markers of Pro-B cell markers can include B220/CD45R, C1qR1/CD93, CD24, CD34, CD38, CD43, CD117/c-kit, CD20, IL-3R alpha, IL-7R alpha/CD127, Neprilysin/CD10, and Pax/BSAP. In some embodiments, Pre-B cell markers can include B220/CD45R, C1qR1/CD93, CD19, CD24, CD34, CD38, CD43, CD 117/c-kit, CD20, IL-3R alpha, IL-4R alpha, IL-7R alpha/CD127, Neprilysin/CD10, and Pax5/BSAP. Immature B cell markers can include B220/CD45R, C1qR1/CD93, CD19, CD21, CD23/Fc epsilon RII, CD24, CD27/TNFRSF7, CD38, CD40/RNFRSF5, CD43, CD 117/c-kit, IL-4R alpha, IL-7R alpha/CD127, and Neprilysin/CD10. Human transitional B cell markers can include C1qR1/CD93, CD5, CD19, CD21, CD23/Fc epsilon RII, CD24, CD27/TNFRSF7, CD38, Neprilysin/CD10, and TACI/TNFRSF13B. In some embodiments, marginal zone B cell markers can include B220/CD45R, C1qR1/CD93 CD1c/BDCA-1, CD1d, CD19, CD21, CD23/Fc epsilon RII, CD27/TNFRSF7, CD43, CD20, FCRL3/FcRH3, and TACI/TNFRSF13B. Follicular B cell markers can include B220/CD45R, CD1d, CD19, CD21, CD23/Fc epsilon RII, CD24, CD27/TNFRSF7, CD38, CD43, CD20, CXCR5, MHC II, Neprilysin/CD10, Siglec-2/CD22, and TACI/TNFRSF13B. Activated Germinal Center B cell markers can include B220/CD45R, CD19, CD27/TNFRSF7, CD38, CD40/TNFRSF7, CD83, CD20, MHC II, and TACI/TNFRSF13B. Memory B cell markers can include B220/CD45R, C1qR1/CD93, CD19, CD21, CD27/TNFRSF7, CD40/TNFRSF7, CD20, MHC II, and TACI/TNFRSF13B. PlasmablasT-cell markers can include B220/CD45R, BCMA/TNFRSF7, CD19, C1qR1/CD93, CD27/TNFRSF7, CD38, and Syndecan-1/CD138. Plasma cell markers can include B220/CD45R, BCMA/TNFRSF17, BLIMP1/PRDM1, CD19, CD27/TNFRSF7, CD38, CD20, CXCR4, MHC II, and Syndecan-1/CD138.

B-cells can be isolated or generated from a biological sample by methods well known in the art. Suitable biological samples for isolation or generation of B cells include without limitation a peripheral blood sample, bone marrow sample, umbilical cord blood sample or the like. By means of an example but without limitation, B cells present in a biological sample may be isolated by immunofluorescent or immunomagnetic labelling of select surface markers known to be expressed or not expressed by B cells, coupled with a corresponding fluorescence activated cell sorting (FACS) gating strategy or immunomagnetic separation, respectively. Other methods are generally known in the art. Engineered B cells can be identified using one or more of the same markers and/or signatures.

Engineered Dendritic Cells

In certain embodiments, the engineered APC is an engineered dendritic cell, e.g., at any stage of differentiation (e.g., a stem cell, a progenitor cell, a mature cell) or any activation stage. As used throughout this specification, "dendritic cell" (DC) refers to any member of a diverse population of morphologically similar cell types found in lymphoid or non-lymphoid tissues. DC may include, for example, "professional" antigen presenting cells, and have a high capacity for sensitising MHC-restricted T-cells. DCs may be recognised, for example, by function, by phenotype and/or by gene expression pattern, particularly by cell surface phenotype. These cells can be characterised by their distinctive morphology, high levels of surface MHC-class II expression and ability to present antigen to CD4+ and/or CD8+ T-cells, particularly to naive T-cells. Functionally, DCs may be identified by any suitable assay, known to one of skilled in the art, for determination of antigen presentation. Such assays may include, for example, testing the ability to stimulate antigen-primed and/or naive T-cells by presentation of a test antigen, followed by determination of T-cell proliferation, release of cytokines such as IL-2, and the like. Dendritic cells can be isolated or generated from a biological sample by methods well known in the art. Suitable biological samples for isolation or generation of DC include without limitation a peripheral blood sample, bone marrow sample, umbilical cord blood sample or the like. By means of an example but without limitation, DC present in a biological sample may be isolated by immunofluorescent or immunomagnetic labelling of select surface markers known to be expressed or not expressed by DC, coupled with a corresponding fluorescence activated cell sorting (FACS) gating strategy or immunomagnetic separation, respectively. Alternatively, DC can be generated from CD14+ monocytes by incubating them with suitable cytokines (Zhou & Tedder, Proc Natl Acad Sci USA. 1996, vol. 93, 2588-92).

In certain embodiments, the engineered APC may be a progenitor or precursor of a dendritic cell. Progenitors or precursors of dendritic cells as intended herein may be capable of also differentiating to other immune cell type(s), or else may be committed to differentiate to dendritic cells and not capable of differentiating to other immune cell types. Engineered DCs can be identified using one or more of the same markers and/or signatures.

Engineered Macrophages

In some embodiments, the engineered APC can be an engineered macrophage. As used throughout this specification "macrophage" refers to a heterogenous population of leukocytes specialized and capable of detecting, phagocytosing, attacking, and/or destroying bacteria and other harmful organisms, pathogens, and other cells that can be differentiated from monocytes. Macrophages can be professional antigen presenting cells and can express MHC I and MHC II molecules. Macrophages can release cytokines and thus can stimulate inflammatory processes in other cells. Macrophages can express pathogen recognition molecules such as Toll-like receptors, which can bind specifically to different pathogenic and non-pathogenic components, such as sugars (e.g. lipopolysaccharide), RNA, DNA, and extracellular proteins and peptides. Macrophages exist in nearly all tissues and are differentiated from monocytes. The type of macrophage depends upon the type(s) of cytokines that the monocytes are exposed to during differentiation. Both macrophages and monocytes (specifically defined elsewhere herein) can both non-specific defense (innate immunity) as well as to help initiate specific defense mechanisms (adaptive immunity) of vertebrates. They also can stimulate lymphocytes and other immune cells to respond to pathogens.

Macrophages can be classified into two main groups designated M1 and M2. M1 macrophages, or classically activated macrophages, are immune effector cells that are aggressive against microbes and can engulf and digest affected cells much more readily, and they also produce many lymphokines. M1 macrophages are activated by LPS and IFN-gamma and secrete high levels of IL-12 and low levels of IL-10. M2 describes other types of macrophages, including those that function in wound healing and tissue repair, and those that turn off immune system activation by producing anti-inflammatory cytokines like IL-10. M2, or alternatively activated macrophages, are activated by IL-4 and produce high levels of IL-10 and low levels of IL-12. Tumor-associated macrophages are thought to be M2 macrophages. In one embodiment of the invention, macrophages are M2 macrophages. Macrophages can be identified and their level determined by detecting or determining the level of proteins specifically expressed in macrophages including but not limited to CD68, CD14, CD163, CD80, MAC2 (galectin-3), EMR1-F4/80, CD11b and CD205, or RNA encoding these proteins.

Macrophages can be isolated or generated from a biological sample by methods well known in the art. Suitable biological samples for isolation or generation of macrophages include without limitation a peripheral blood sample, bone marrow sample, umbilical cord blood sample, a tissue sample, or the like. By means of an example but without limitation, macrophages present in a biological sample may be isolated by immunofluorescent or immunomagnetic labelling of select surface markers known to be expressed or not expressed by macrophages, coupled with a corresponding fluorescence activated cell sorting (FACS) gating strategy or immunomagnetic separation, respectively. Other methods are generally known in the art. Engineered macrophages can be identified using one or more of the same markers and/or signatures.

Engineered Monocytes

In certain embodiments, the engineered APC is a monocyte, e.g., at any stage of differentiation (e.g., a stem cell, a progenitor cell, a mature cell) or any activation stage. As used throughout this specification, "monocyte" refers to a type of white blood cells capable of dividing and differentiating into and hence replenishing or producing macrophages and dendritic cells, e.g., under normal states or in response to inflammation signals. Monocytes are typically identified in stained smears by their large bilobate nucleus. Monocytes are further typified by expression of CD14 and can also show expression of one or more of following surface markers such as 125I-WVH-1, Adipophilin, CB12, CD11a, CD11b, CD15, CD54, CD163, cytidine deaminase, or FLT1. Monocytes encompass previously known subtypes, such as the 'classical' monocyte, the 'non-classical' monocyte and the 'intermediate' monocyte, which are present in human tissues such as blood. 'Classical' monocytes are typified by high level expression of CD14 (CD14$^{++}$ monocyte) and 'non-classical' monocytes display low level expression of CD14 and additional co-expression of CD16 (CD14$^+$CD16$^{++}$ monocyte). 'Intermediate' monocytes show a phenotype intermediate between the aforementioned types in terms of CD14 and CD16 expression (CD14$^{++}$CD16$^+$ monocyte).

Monocytes can be isolated or generated from a biological sample by methods well known in the art. Suitable biological samples for isolation or generation of macrophages include without limitation a peripheral blood sample, bone marrow sample, umbilical cord blood sample, a tissue sample, or the like. By means of an example but without limitation, monocytes present in a biological sample may be isolated by immunofluorescent or immunomagnetic labelling of select surface markers known to be expressed or not expressed by monocytes, coupled with a corresponding fluorescence activated cell sorting (FACS) gating strategy or immunomagnetic separation, respectively. Other methods are generally known in the art. Engineered monocytes can be identified using one or more of the same markers and/or signatures.

Modified Antigen Presenting/Processing Pathways

The engineered APC can have a modified antigen presentation and/or processing pathway such that the presentation and/or processing of an antigen (either intracellular or extracellular) is modified as compared to a non-modified control APC. In some embodiments, the antigen presentation and/or processing pathway that is modified is the cross-presentation pathway. As used herein "antigen presentation and/or processing pathway" refers to a pathway within an APC that processes and associates an antigen or fragment thereof with a presentation molecule (e.g. an MHC) and ultimately results in the expression of the antigen-presentation molecule complex on the surface of the APC. Generally, antigens can be processed and presented in complex with MHC molecules by APCs. The origin of the antigen (e.g. extracellular v. intracellular) and the involvement, if any, of the cross-presentation pathway can determine if the antigen is processed and presented in a complex with an MHC I or an MHC II molecule.

Extracellular originating antigens are generally processed differently and involves a different antigen presentation and/or processing pathway than those that originate intracellularly. Intracellular antigens are generally processed by a pathway that results, absent any cross-presentation, in complexing only with an MHC I molecule and expression of said complex on the surface of the APC for presentation to T-cells that are capable of recognizing and interacting with antigen-MHC I complexes. Extracellular antigens can be internalized by the APC by various mechanisms and are generally processed by a pathway that results, absent any cross-presentation, only with an MHC II molecule and expression of said complex on the surface of the APC for presentation with T-cells that are capable of recognizing and interacting with antigen-MHC II complexes.

Cross-presentation refers to the ability of professional APCs to process internalized extracellular antigens such that they are presented on MHC I cells as well as MHC II cells. See e.g. Embgenbroich and Burgdorf 2018. Front. Immunol. 9:1643. Doi 10.3389/fimmu.2018.01643. In MHC-II restricted presentation, internalized extracellular antigens are degraded in endo/lysosomal compartments by proteases such as cathepsins. Newly synthesized and stabilized MHC II molecules, are transported from the ER toward the endo/lysosomal compartments, where the stabilizing invariant chain is degraded, resulting in the binding of only the CLIP fragment to the MHC II. Subsequently CLIP is replaced by the antigen fragments by the chaperon HLA-DM. In contrast, cross-presentation can involve a variety of other pathways and processes including, the vacuolar pathway and the endosome-to-cytosol pathway. In the vacuolar pathway, antigen processing and loading onto MHC I molecules occurs within the endo/lysosomal compartment. After internalization of extracellular peptide antigens are degraded by lysosomal proteases and are loaded into MHC class I molecules there. Cathepsin S has been demonstrated to play a role in antigen degradation for the vacuolar pathway.

In the endosome-to-cytosol cross-presentation pathway, internalized extracellular antigens are transported from the endosomal compartment to the cytosol, where they are degraded by the proteasome. Peptides resulting from the degradation by the proteasome are subsequently transported by the transporter associated with antigen processing (TAP) into the ER or back into the antigen-containing endosomes, where they can be loaded onto MHC I molecules.

Cross-presentation can be regulated by intra-endosomal antigen stability. Efficiency of cross-presentation can be negatively affected by rapid lysosomal degradation of internalized extracellular antigens. See e.g. Accapezzato D, et al. J Exp Med. 2005 Sep. 19; 202(6):817-28. Further, lysosomal maturation and activation of lysosomal proteases is finetuned by transcription factor TFFEB, which can thus regulate cross-presentation. See e.g. Samie M and Cresswell P. Nat Immunol. 2015 July; 16(7):729-36. Rapid antigen degradation can quickly destroy a large amount of epitopes before they can be processed and presented into MHC I molecules. Chatterjee et al. Blood. 2012 Sep. 6; 120(10): 2011-20 and Alloatti et al. Immunity. 2015 Dec. 15; 43(6): 1087-100. Peptide loaded MHC I molecules also have a limited life span at the cell membrane. See e.g. Eberl et. al. Eur J Immunol. 1996 September; 26(9):1993-9; Cella et al., Nature (1997) 388:782-7.10.1038/42030; and Rescigno et al. Proc Natl Acad Sci USA. 1998 Apr. 28; 95(9):5229-34.

Antigen Types

The term "antigen" as used throughout this specification refers to a molecule or a portion of a molecule capable of being bound by an antibody, or by a T-cell receptor (TCR) when presented by MHC molecules. At the molecular level, an antigen is characterised by its ability to be bound at the antigen-binding site of an antibody. The specific binding denotes that the antigen will be bound in a highly selective manner by its cognate antibody and not by the multitude of other antibodies which may be evoked by other antigens. An antigen is additionally capable of being recognised by the immune system. In some instances, an antigen is capable of eliciting a humoral immune response in a subject. In some instances, an antigen is capable of eliciting a cellular immune response in a subject, leading to the activation of B- and/or T-lymphocytes.

As used throughout this specification, "immune response" refers to a response by a cell of the immune system, such as a B cell, T-cell (CD4+ or CD8+), regulatory T-cell, antigen-presenting cell, dendritic cell, monocyte, macrophage, NKT-cell, NK cell, basophil, eosinophil, or neutrophil, to a stimulus. In some embodiments, the response is specific for a particular antigen (an "antigen-specific response"), and refers to a response by a CD4 T-cell, CD8 T-cell, or B cell via their antigen-specific receptor. In some embodiments, an immune response is a T-cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

As used herein "T-cell response" refers more specifically to an immune response in which T-cells directly or indirectly mediate or otherwise contribute to an immune response in a subject. T-cell-mediated response may be associated with cell mediated effects, cytokine mediated effects, and even effects associated with B cells if the B cells are stimulated, for example, by cytokines secreted by T-cells. By means of an example and without limitation, effector functions of NMC class I restricted Cytotoxic T lymphocytes (CTLs), may include cytokine and/or cytolytic capabilities, such as lysis of targeT-cells presenting an antigen peptide recognised by the T-cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for NMC class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

In some instances, an antigen is capable of eliciting a humoral and cellular immune response in a subject. Hence, an antigen may be preferably antigenic and immunogenic. Alternatively, an antigen may be antigenic and not immunogenic. Typically, an antigen may be a peptide, polypeptide, protein, nucleic acid, an oligo- or polysaccharide, or a lipid, or any combination thereof, a glycoprotein, proteoglycan, glycolipid, etc. In certain embodiments, an antigen may be a peptide, polypeptide, or protein. An antigen may have one or more than one epitope. The terms "antigenic determinant" or "epitope" generally refer to the region or part of an antigen that specifically reacts with or is recognised by the immune system, specifically by antibodies, B cells, or T-cells. An antigen the administration of which results in the induction of immune tolerance toward the antigen may also be denoted as "tolerogen". The term "immune tolerance" as used throughout this specification refers to any mechanism by which a potentially injurious immune response is prevented, suppressed, delayed in the onset or progression, reduced in the risk of the onset or progression, or shifted to a non-injurious immune response. Specific immune tolerance occurs when immune tolerance is preferentially invoked against certain antigen(s) in comparison with others. Immune tolerance treatments may thus encompass antigen-specific therapies used to attenuate autoreactive T- and/or B-cell responses, while leaving global immune function intact (tolerising vaccines).

An antigen, as contemplated throughout this specification, can be obtained by any means available to a skilled person, e.g., may be isolated from a naturally-occurring material comprising the antigen, or may be produced recombinantly by a suitable host or hosT-cell expression system and optionally isolated therefrom (e.g., a suitable bacterial, yeast, fungal, plant or animal host or hosT-cell expression system), or may be produced recombinantly by cell-free transcription or translation, or non-biological nucleic acid or peptide synthesis.

As used throughout this specification, the term "autoimmune antigen" refers to any self-component, i.e., a component own or native to a subject, e.g., a self-peptide, self-polypeptide, or self-protein, that serves either as a target or cause of an autoimmune condition or disease. Examples of autoimmune antigens include, but are not limited to, myelin basic protein, proteolipid protein, or myelin oligodendrocyte protein (multiple sclerosis); peripheral myelin proteins PO and P2 (Guillain-Barre syndrome); acetylcholine receptor (myasthenia gravis); cardiac myosin (rheumatic fever/myocarditis); proteins of the beta cells of the Islets of Langerhans—glutamic acid decarboxylase, insulin (Type I autoimmune diabetes mellitus); thyroid-stimulating hormone receptor (Grave's disease); platelet antigens (thrombocytopenic purpura); neuromuscular junctions (myasthenia gravis); red blood cell antigens (autoimmune haemolytic anaemia); intracellular antigens (spliceosomes, ribosomes, histones, nucleic acids, etc.) (systemic lupus erythematosus); rheumatoid factor IgG complexes, synovial joint antigens (rheumatoid arthritis); epidermal cadherin (Pemphigus vulgaris); and alpha-3 subunit of type IV collagen (Goodpasture's syndrome).

The term "tumor antigen" as used throughout this specification refers to an antigen that is uniquely or differentially expressed by a tumor cell, whether intracellular or on the tumor cell surface (preferably on the tumor cell surface), compared to a normal or non-neoplastic cell. By means of example, a tumor antigen may be present in or on a tumor cell and not typically in or on normal cells or non-neoplastic cells (e.g., only expressed by a restricted number of normal tissues, such as testis and/or placenta), or a tumor antigen may be present in or on a tumor cell in greater amounts than in or on normal or non-neoplastic cells, or a tumor antigen may be present in or on tumor cells in a different form than that found in or on normal or non-neoplastic cells. The term thus includes tumor-specific antigens (TSA), including tumor-specific membrane antigens, tumor-associated antigens (TAA), including tumor-associated membrane antigens, embryonic antigens on tumors, growth factor receptors, growth factor ligands, etc. The term further includes cancer/testis (CT) antigens. Examples of tumor antigens include, without limitation, 3-human chorionic gonadotropin (PHCG), glycoprotein 100 (gp100/Pme117), carcinoembryonic antigen (CEA), tyrosinase, tyrosinase-related protein 1 (gp75/TRP1), tyrosinase-related protein 2 (TRP-2), NY-BR-1, NY-CO-58, NY-ESO-1, MN/gp250, idiotypes, telomerase, synovial sarcoma X breakpoint 2 (SSX2), mucin 1 (MUC-1), antigens of the melanoma-associated antigen (MAGE) family, high molecular weight-melanoma associated antigen (HMW-MAA), melanoma antigen recognized by T-cells 1 (MART1), Wilms' tumor gene 1 (WT1), HER2/neu, mesothelin (MSLN), alphafetoprotein (AFP), cancer antigen 125 (CA-125), and abnormal forms of ras or p53.

The term "pathogen antigen" as used throughout this specification refers to an antigen of a biological entity that is pathogenic to a subject, hence, capable of causing a pathological condition or disease in the subject. Pathogens encompass pathogenic microorganisms, such as any pathogenic type of bacterium (including archaebacteria and eubacteria), protozoum, fungus (including molds and yeasts), viroid and virus; as well as single-cell and multi-cellular parasites, e.g., helminths (e.g., cestodes, nematodes and trematodes). The term also encompasses biological entities, which display pathogenicity in immunocompromised hosts, but may not ordinarily be pathogenic in a non-immunocompromised host.

In certain embodiments, the pathogen is a bacterial, fungal, protozoal, parasitic, or viral pathogen.

Non-limiting examples of bacterial pathogens from which the pathogen antigen can be derived include any pathogenic bacterial species from a genus selected from the group comprising or consisting of *Bacillus, Bordetella, Borrelia, Brucella, Burkholderia, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, and *Yersinia*.

Non-limiting examples of fungal pathogens from which the pathogen antigen can be derived include any pathogenic fungal species from a genus selected from the group comprising or consisting of *Candida* (e.g., *Candida albicans*), *Aspergillus* (e.g., *Aspergillus fumigatus, Aspergillus flavus, Aspergillus clavatus*), *Cryptococcus* (e.g., *Cryptococcus neoformans, Cryptococcus gattii*), *Histoplasma* (e.g., *Histoplasma capsulatum*), *Microsporum* (e.g., *Microsporum gypseum*), *Pneumocystis* (e.g., *Pneumocystis jirovecii, Pneumocystis carinii*), *Stachybotrys* (e.g., *Stachybotrys chartarum*), and *Trichophyton* (e.g., *Trichophyton rubrum*).

Non-limiting examples of protozoal pathogens from which the pathogen antigen can be derived include, e.g., protists of the genus *Plasmodium*, such as *Plasmodium falciparum, Plasmodium vivax, Plasmodium ovale*, or *Plasmodium malariae*, and further pathogens, such as *Entamoeba histolytica, Giardia lamblia*, or *Trypanosoma brucei*.

Non-limiting examples of parasitic pathogens from which the pathogen antigen can be derived include single-cell and multicellular parasites, such as *Acanthamoeba, Anisakis, Ascaris lumbricoides, Balantidium coli*, Cestoda (tapeworm), Chiggers, *Cochliomyia hominivorax, Entamoeba histolytica, Fasciola hepatica, Giardia lamblia*, Hookworm; *Leishmania, Linguatula serrata*, Liver fluke, *Loa loa, Paragonimus* (lung fluke), Pinworm, *Plasmodium falciparum, Schistosoma, Strongyloides stercoralis*, Tapeworm, *Toxoplasma gondii; Trypanosoma*; Whipworm; or *Wuchereria bancrofti*.

Non-limiting examples of viral pathogens from which the pathogen antigen can be derived include adenoviruses, papillomaviruses, hepaciviruses (e.g., hepatitis B), parvoviruses, pox viruses (e.g., small pox virus, vaccinia virus), Epstein-Barr virus, cytomegalovirus (CMV), herpes simplex viruses, roseolovirus, varicella zoster virus, filoviruses (e.g., Ebola virus, Marburg virus), paramyxoviruses (e.g., measles virus, mumps virus, Nipah virus, Hendra virus, human respiratory syncytial virus (RSV), parainfluenza viruses, Newcastle disease virus, human metapneumovirus), orthomyxoviruses (e.g., influenza A, influenza B, influenza C), rhabdoviruses (e.g., Lyssavirus, also known as rabies virus), arenaviruses (e.g., Lassa virus), coronaviruses (severe acute respiratory syndrome (SARS), Middle East respiratory syndrome (MERS)), human enteroviruses, hepatitis A virus, human rhinoviruses, polio virus, retroviruses (e.g., human immunodeficiency virus 1 (HIV-1)), rotaviruses, flaviviruses (e.g., West Nile virus, dengue virus, yellow fever virus, Zika virus), hepaciviruses (e.g., hepatitis C virus), or rubella virus.

Modified Antigen Presenting/Processing Pathways

The engineered APCs can have a one or more modified antigen presentation pathways. In some embodiments, MHC I restricted presentation pathway is modified, the MHCI II restricted presentation pathway is modified, a cross-presentation pathway is modified, or any combination thereof is modified. In some embodiments, the engineered APCs can have one or more antigen processing pathway gene modified. In some embodiments, that one or more antigen processing pathway gene that is/are modified is/are modified such that the expression of that gene is increased and/or the expression and/or activity of the respective gene product(s) is/are increased. In some embodiments, that one or more antigen processing pathway gene that is/are modified is/are modified such that the expression of that gene is decreased and/or the expression and/or activity of the respective gene product(s) is/are decreased.

As used herein an "antigen processing pathway gene" or "gene relating to the antigen processing pathway" refers to a gene involved in any part of antigen presentation, recognition and processing by an APC. As used herein a "cross-presentation pathway gene" or "gene relating to the cross-presentation pathway" refers to a gene involved in any part of cross-presentation and/or processing of an antigen by an APC.

A "gene product" refers to any product of such gene including proteins, polypeptides, peptides and RNA molecules (i.e. polynucleotides, such as tRNA, rRNA, mRNA). Hence in one embodiment, expression of mRNA, tRNA, rRNA, protein, polypeptide or peptide encoded by said gene relating to antigen processing pathway is determined. In one embodiment, an expression level of said gene product is determined.

As used herein "reduced expression" or "underexpression" refers to a reduced or decreased expression of a gene, such as a gene relating to an antigen processing pathway, or a gene product thereof in sample as compared to the expression of said gene or gene product in a suitable control. As used throughout this specification, "suitable control" is a control that will be instantly appreciated by one of ordinary skill in the art as one that is included such that it can be determined if the variable being evaluated an effect, such as a desired effect or hypothesized effect. One of ordinary skill in the art will also instantly appreciate based on inter alia, the context, the variable(s), the desired or hypothesized effect, what is a suitable or an appropriate control needed. In one embodiment, said control is a sample from a healthy individual or otherwise normal individual. By way of a non-limiting example, if said sample is a sample of a lung tumor and comprises lung tissue, said control is lung tissue of a healthy individual. The term "reduced expression" preferably refers to at least a 25% reduction, e.g., at least a 30%, 40%, 50%, 60%, 70%, 75%, 80%, 85%, 90%, 95%, 98% or 99% reduction, relative to such control.

The term "modification causing said reduced expression" refers to a modification in a gene which affects the expression level of that or another gene such that the expression level of that or another gene is reduced or decreased. In particular embodiments, the modification is in a gene relating to an antigen processing pathway. In some embodiments, the modification is in a gene relating to the cross-presentation pathway. Said modification can be any nucleic acid modification including, but not limited to, a mutation, a deletion, an insertion, a replacement, a ligation, a digestion, a break and a frameshift. Said modification is preferably selected from the group consisting of a mutation, a deletion and a frameshift. In particular embodiments, the modification is a mutation which results in reduced expression of the functional gene product.

As used herein "increased expression" or "overexpression" are both used to refer to an increased expression of a gene, such as a gene relating to an antigen processing and/or presentation pathway, or gene product thereof in a sample as compared to the expression of said gene or gene product in a suitable control. The term "increased expression" preferably refers to 10%, 20%, 30%, 40%, 50%, 60%, 70%, 80%, 90%, 100%0, 110%, 120%, 130%, 140%, 150%1, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, 1000%, 1010%, 1020%, 1030%, 1040%, 1050%, 1060%, 1070%, 1080%, 1090%, 1100%, 1110%, 1120%, 1130%, 1140%, 1150%, 1160%, 1170%, 1180%, 1190%, 1200%, 1210%, 1220%, 1230%, 1240%, 1250%, 1260%, 1270%, 1280%, 1290%, 1300%, 1310%, 1320%, 1330%, 1340%, 1350%, 1360%, 1370%, 1380%, 1390%, 1400%, 1410%, 1420%, 1430%, 1440%, 1450%, 1460%, 1470%, 1480%, 1490%, or/to 1500% or more increased expression relative to a suitable control.

The term "modification causing said increased expression" refers to a modification in a gene which affects the expression level of that or another gene such that expression of that or another gene is increased. In particular embodiments, the modification is in a gene relating to an antigen processing pathway. In some embodiments, the modification is in a gene relating to the cross-presentation pathway. Said modification can be any nucleic acid modification including, but not limited to, a mutation, a deletion, an insertion, a replacement, a ligation, a digestion, a break and a frameshift. Said modification is preferably selected from the group consisting of a mutation, a deletion and a frameshift. In particular embodiments, the modification is a mutation which results in reduced expression of the functional gene product.

Genes that can be modified include, but are not limited to, gene(s) that are involved in and/or regulate antigen presentation in an antigen presenting cell, including but not limited to gene(s) that encode a component of a MHC I or MHC II complex, gene(s) that encode a molecule involved in a signaling and/or other regulatory pathway involved in controlling an antigen processing/presentation pathway, genes that encode a component of an antigen presentation pathway (e.g. MHC I restricted pathway, MHC II restricted pathway, and/or a cross-presentation pathway).

In particular embodiments, the gene encodes a protein involved in antigen presentation, such part of an MHC class I or class II complexes. MHC class I complexes are heterodimers that consist of two polypeptide chains, α and β2-microglobulin (b2m, also referred to herein as B2M). The two chains are linked noncovalently via interaction of b2m and the α3 domain. The α chain is polymorphic and encoded by a HLA gene, the b2m subunit is encoded by the beta-2-microglobulin gene. In one embodiment, said gene encodes a B2M protein.

In some embodiments, one or more genes that encode and/or regulate the function or activity of one or more lysosomal proteases (e.g. Cathepsins L, S, D, and/or B) involved in degrading antigens can be modified in the engineered APC. In some embodiments, the one or more genes are modified such that the expression, function, and/or activity of the lysosomal protease(s) are reduced or inhibited, which can increase the time the antigen is available for processing, such as for cross-presentation. In some embodiments, the one or more genes are modified such that the expression, function, and/or activity of the lysosomal protease(s) are increased, which can decrease the time the antigen is available for processing, such as for cross-presentation, and reduce cross-presentation.

In some embodiments, one or more genes that encode and/or regulate the function or activity of one or more proteins involved in maintain the pH of the endosome can be modified in the engineered APC. In some embodiments, one or more genes that can increase/decrease the alkalization of the endosome can be modified in the engineered APC. In some embodiments, one or more genes can be modified such that they increase the alkalization of the endosome. An increase in the alkalization in the endosome can prevent pH dependent activation of lysosomal proteases. In some embodiments, one or more genes can be modified such that they decrease the alkalization of the endosome. A decrease in the alkalization can increase pH dependent activation of lysosomal proteases, which can increase antigen degradation and reduce cross-presentation. In some embodiments, one or more genes that can modify V-ATPase activity in the engineered APC, particularly in the endosome, can be modified in the engineered APC. In some embodiments, the one or more genes that can modify V-ATPase activity can be modified such that they can reduce V-ATPase activity, which can decrease degradation of an antigen in an endosome. In some embodiments, the one or more genes that can modify V-ATPase activity can be modified such that they can increase V-ATPase activity, which can increase degradation of an antigen in an endosome.

In some embodiments, one or more genes that encode NOX2 or gene product that can regulate and/or recruit NOX2 to the endosomal membrane can be modified in the engineered APC. In some embodiments, the one or more genes that encode NOX2 or gene product that can regulate and/or recruit NOX2 to the endosomal membrane can be modified such that NOX2 or the gene product or activity thereof is decreased. In some embodiments, the one or more genes that encode NOX2 or gene product that can regulate and/or recruit NOX2 to the endosomal membrane can be modified such that NOX2 or the gene product or activity thereof is increased. In some embodiments, one or more genes that encode Rab27a can be modified in the engineered APC. In some embodiments, one or more genes that encode Rab27a can be modified such that expression and/or activity of Rab27a increased. In some embodiments, one or more genes that encode Rab27a can be modified in the engineered APC. In some embodiments, one or more genes that encode Rab27a can be modified such that expression and/or activity of Rab27a decreased. Increased recruitment of NOX2 to the endosomal membrane can mediate the generation of reactive oxygen species (ROS), which can make hydrogen peroxide. Trapping ROS can result in active alkalization and can impair pH dependent activation of lysosomal proteases. In some embodiments, recruitment of NOX2 can be mediated by Rab27a.

In some embodiments, the protein or peptide antigen can be glycosylated. In some embodiments, the glycan is high mannose or a hybrid and capable of being bound or interacting with a mannose receptor. Antigens being capable of being bound or interacting with the mannose receptor can be transported into an endosomal compartment that does not or more slowly degrades the antigen, thus allowing more time for cross-presentation processing. In some embodiments, the engineered APC can contain one or more modified genes that are capable of encoding endocytosis receptors that can specifically target non-degradative endosomal compartments, such as a mannose receptor. In some embodiments, the one or more genes that are capable of encoding endocytosis receptors that can specifically target non-degradative endosomal compartments, such as a mannose receptor, can be modified such that expression of the endocytosis receptor(s) can be increased. In some embodiments, the one or more genes that are capable of encoding endocytosis receptors that can specifically target non-degradative endosomal compartments, such as a mannose receptor, can be modified such that expression of the endocytosis receptor(s) can be decreased.

Increased expression of gamma-interferon-inducible lysosomal thiol reductase (GILT) can increase unfolding and disulfide bridges present in an antigen. Unfolding and a reduction in disulfide bridges can increase the translocation of antigens into the cytosol, which can increase cross-presentation. In some embodiments, one or more genes that can encode GILT can be modified in the engineered APC. In some embodiments, one or more genes that can encode GILT can be modified such that the expression of GILT is increased. In some embodiments, one or more genes that can encode GILT can be modified such that the expression of GILT is decreased.

Members of the ER associated degradation machinery can contribute to antigen translocation for cross-presentation. Such members can include AAA ATPase p97 and Sec61. Reduction in the expression of one or more of these members can increase translocation of antigens for cross-presentation. In some embodiments, one or more genes that encode AAA ATPase p97 can be modified in the engineered APC. In some embodiments, the one more genes that encode the AAA ATPase p97 can be modified such that expression of the AAA ATPase p97 is/are increased. In some embodiments, the one more genes that encode the AAA ATPase p97 can be modified such that expression of the AAA ATPase p97 is/are decreased.

In some embodiments, one or more genes encoding TAP are modified in the engineered APC. In some embodiments, the one or more genes encoding TAP are modified such that TAP expression and/or activity are increased. In some embodiments, the one or more genes encoding TAP are modified such that TAP expression and/or activity are decreased.

ERAP and/or IRAP can mediate protein/peptide antigen trimming for loading into an MHC I molecule. In some embodiments, a gene encoding ERAP can be modified in the engineered APC. In some embodiments, a gene encoding ERAP can be modified in the engineered APC such that the expression and/or activity of ERAP is increased. In some embodiments, a gene encoding ERAP can be modified in the engineered APC such that the expression and/or activity of ERAP is decreased. In some embodiments, a gene encoding IRAP can be modified in the engineered APC. In some embodiments, a gene encoding IRAP can be modified in the engineered APC such that the expression and/or activity of IRAP is increased. In some embodiments, a gene encoding IRAP can be modified in the engineered APC such that the expression and/or activity of IRAP is decreased.

Entry of MHC I into an endosomal recycling compartment from the cell membrane can endosome can play a role in cross-presentation and can be mediated by Rab11a. See e.g. Nair-Gupta P, et al. Cell. 2014 Jul. 31 158(3):506-21. In some embodiments, a gene encoding Rab11a can be modified in the engineered APC. In some embodiments, a gene encoding Rab11a can be modified such that expression and/or activity of Rab11a is increased in the engineered APC. In some embodiments, a gene encoding Rab11a can be modified such that expression and/or activity of Rab11a is decreased in the engineered APC.

SNARE proteins, SNAP23, and MyD88 signaling molecules can be involved in MHC I transport to phagosomes and can play role in cross-presentation. See e.g. Nair-Gupta P, et al. Cell. 2014 Jul. 31 158(3):506-21 and Cebrian et. al. Cell. 2011 Dec. 9; 147(6):1355-68. In some embodiments, a gene encoding a SNARE protein can be modified in the engineered APC. In some embodiments, a gene encoding a SNARE protein can be modified such that expression and/or activity of the SNARE protein is increased in the engineered APC. In some embodiments, a gene encoding the SNARE protein can be modified such that expression and/or activity of the SNARE protein is decreased in the engineered APC. In some embodiments, the SNARE protein that is modified is Sec22b and/or syntaxin 4. In some embodiments, a gene encoding SNAP23 can be modified in the engineered APC. In some embodiments, a gene encoding SNAP23 can be modified such that expression and/or activity of SNAP23 is increased in the engineered APC. In some embodiments, a gene encoding SNAP23 can be modified such that expression and/or activity of SNAP23 is decreased in the engineered APC. In some embodiments, a gene encoding MyD88 can be modified in the engineered APC. In some embodiments, a gene encoding MyD88 can be modified such that expression and/or activity of MyD88 is increased in the engineered APC. In some embodiments, a gene encoding MyD88 can be modified such that expression and/or activity of MyD88 is decreased in the engineered APC.

UNC93B1 may play a role in cross-presentation. In some embodiments, a gene encoding UNC93B1 can be modified such that expression and/or activity of UNC93B1 is increased in the engineered APC. In some embodiments, a gene encoding UNC93B1 can be modified such that expression and/or activity of UNC93B1 is decreased in the engineered APC.

Genes that are involved in cell signaling pathways that can regulate antigen presentation in an APC can include, but are not limited to, MAPK, MAPKKK, MAPKK, p38, INK, ERK1/2, MMK3, MKK6, protein kinase C family members (e.g. PKC alpha, beta (both I and II), atypical PKC ζ, and λ/ι, and novel (δ, ε, and θ), toll-like receptors (e.g. TLR-1, TLR2, TLR-4, TLR-5, TLR7, and TLR9), INF-gamma, IL-4, TNF-alpha, JAK, STAT (e.g. STAT3), Rho GTPases, Rho kinase. See e.g. R. R. Brutkiewicz. 2016. J. Immunol. 197(8):2971-2979. In some embodiments, a genes each encoding a protein selected from the group of MAPK, MAPKKK, MAPKK, p38, INK, ERK1/2, MMK3, MKK6, protein kinase C family members (e.g. PKC alpha, beta (both I and II), atypical PKC ζ, and λ/ι, and novel (δ, ε, and θ), toll-like receptors (e.g. TLR-1, TLR2, TLR-4, TLR-5, TLR7, and TLR9), INF-gamma, IL-4, TNF-alpha, JAK, STAT (e.g. STAT3), Rho GTPases, and Rho kinase can be modified in the engineered APC. In some embodiments, one or more of genes each encoding a protein selected from the group of MAPK, MAPKKK, MAPKK, p38, INK, ERK1/2, MMK3, MKK6, protein kinase C family members (e.g. PKC alpha, beta (both I and II), atypical PKC ζ, and λ/ι, and novel (δ, ε, and θ), toll-like receptors (e.g. TLR-1, TLR2, TLR-4, TLR-5, TLR7, and TLR9), INF-gamma, IL-4, TNF-alpha, JAK, STAT (e.g. STAT3), Rho GTPases, and Rho kinase can be modified such that the expression of these gene(s) and/or protein(s) is increased. In some embodiments, one or more of genes each encoding a protein selected from the group of MAPK, MAPKKK, MAPKK, p38, INK, ERK1/2, MMK3, MKK6, protein kinase C family members (e.g. PKC alpha, beta (both I and II), atypical PKC ζ, and λ/ι, and novel (δ, ε, and θ), toll-like receptors (e.g. TLR-1, TLR2, TLR-4, TLR-5, TLR7, and TLR9), INF-gamma, IL-4, TNF-alpha, JAK, STAT (e.g. STAT3), Rho GTPases, and Rho kinase can be modified such that the expression of these gene(s) and/or protein(s) is decreased.

In particular embodiments, the methods involve modifying and/or determining a modification in the B2M gene. In particular embodiments, the modification is selected from a mutation, insertion, or a deletion. In particular embodiments, the modification is in exon 1 or exon 2.

In some embodiments, the modification of the B2M gene can reduce expression of the B2Mgene. In some embodiments, the modification of the B2M gene can increase expression of the B2Mgene. Multiple mutations resulting in reduced expression of the functional protein have been disclosed for the B2M gene, such as in Madhavi Challa-Malladi et al. 2011; Cancer Cell 20(6): 728-740). The B2M gene encodes a component of MHC (e.g. MHCI and MHCII) molecules. Exemplary missense mutations include, but are not limited to, T62A, T62G, T62C, T80C, G82A, T193G, A245C, C271A, T304G, A353G, T352A; exemplary nonsense mutations include G299A, G309T, C318G, exemplary frameshift mutations include p.Leu13fs, p.Ser14fs and p.Gly63fs. Further examples include Δ(54-63), Δ(91-101), Δ(103-104), Δ(97-98), Δ(239-240); insT (239-240), InsA(345-346); exemplary splice site mutations include T(+2)A, G(+1)A. However, the detection of modifications need not be limited to those exemplified herein. In particular embodiments, the modification is a chromosomal deletion in a chromosome carrying a gene involved in antigen processing pathway. The BM2 gene is located on chromosome 6, such that a deletion in chromosome 6 can affect BM2 expression. In some embodiments, the engineered APC has a modified BM2 gene. In some embodiments, the BM2 gene is modified such that expression of the BM2 gene is increased. In some embodiments, the BM2 gene is modified such that expression of that BM2 is decreased. However, the detection of modifications need not be limited to those exemplified herein.

In particular embodiments, the gene relates to antigen processing pathway is a human leukocyte antigen (HLA) gene, such as HLA-A, HLA-B, HLA-C, HLA-E, HLA-F, and/or HLA-G. An exemplary mutation of the HLA-C gene is p.W23C. In some embodiments, the engineered APC has one or more modified HLA gene. In some embodiments, the HLA gene is modified such that expression of that HLA gene is increased. In some embodiments, the HLA gene is modified such that expression of that HLA is decreased. However, the detection of modifications need not be limited to those exemplified herein In some embodiments, one or more of the following genes can be modified: LAMP2, PSMB8, TAP1, TAP2, ERAP1, CANX, CALR, TAPBP, PDIA3, CD74, HLA-DMA, HLA-DMB, HLA-DOA, TAPBPL, B2M, ERAP2, HLA-E, HLA-F, HLA-G, TLR4, MYD88, TICAM1, LNPEP, TFEB, RAB27A, SEC61A1, RAB3A, RAB3B, BCAP31, EEA1, LAMP1, RAB4A, RAB5A, RAB11A, RAB7A, RHOB, PKN1, PIK3C3, TF, WASF1, DIAPH1, SYK, ICAM1, and any combination thereof.

Methods of Making the Modified Antigen Presenting Pathways

In some embodiments, antigen presenting pathway gene(s) that can be modified can be identified by performing a CRISPR-Cas system-based loss-of-function screen. In some embodiments, the CRISPR-Cas system-based loss-of-function screen can be performed on a selected portion of the genome of an antigen presenting cell. In some embodiments, the CRISPR-Cas system-based loss-of-function screen can be a genome-wide screen of an antigen presenting cell. Generally, a CRISPR-Cas system-based loss of function screen can include introducing one or more (e.g. in a pooled or multiplexed approach) gRNAs and a Cas protein in a desired cell or cell population followed by a phenotype screening of the resulting cell using an appropriate method. In some embodiments this includes identifying genes that are enriched or depleted in response to the loss of function induced by the CRISPR-Cas system using an appropriate sequencing method (e.g. next-generation sequencing method, single cell sequencing method). Changes in other phenotypes (e.g. protein activity, or other functionalities) can also be measured after loss-of-function of one or more target genes is completed. This can include determining protein amount and/or function, and other appropriate functional tests based on the cell functions of interest.

In some embodiments, one or more phenotypes, in an APC, such as a B-cell or any other APC described herein, can be measured after loss-of-function of one or more genes is induced. In some embodiments, the ability of the cell to present antigen in a MHC class I and/or class II molecule can be determined, which can be optionally in addition to performing a gene expression analysis using an appropriate method. In some embodiments, the ability of the cell to cross-present an antigen can be determined, which can be optionally in addition to performing a gene expression analysis using an appropriate method.

In certain embodiments, the screen can include transiently expressing one or more components of a CRISPR-Cas system in an antigen presenting cell. In some embodiments, the screen can include stably expressing one or more components of a CRISPR-Cas system in an antigen presenting cell. In some embodiments, the Cas protein is stably expressed and one or more gRNAs targeting one or more genes of interest are transiently expressed in an antigen presenting cell. In some embodiments, the gRNA(s) and Cas proteins are both transiently expressed. In some embodiments, the target gene(s) of interest are gene(s) are genes that are involved in and/or regulate antigen presentation in an antigen presenting cell. In some embodiments, the target gene(s) are gene(s) that encode a component of a MHC I or MHC II complex, gene(s) that encode a molecule involved in a signaling and/or other regulatory pathway involved in controlling an antigen processing/presentation pathway, genes that encode a component of an antigen presentation pathway (e.g. MHC I restricted pathway, MHC II restricted pathway, and/or a cross-presentation pathway).

CRISPR-Cas Systems

As previously discussed, antigen presenting pathway gene(s) that can be modified can be identified by performing a CRISPR-Cas system-based loss-of-function screen. In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

Class 1 Systems

The methods, systems, and tools provided herein may be designed for use with Class 1 CRISPR proteins. In certain example embodiments, the Class 1 system may be Type I, Type III or Type IV Cas proteins as described in Makarova et al. "Evolutionary classification of CRISPR-Cas systems: a burst of class 2 and derived variants" Nature Reviews Microbiology, 18:67-81 (February 2020), incorporated in its entirety herein by reference, and particularly as described in FIG. 1, p. 326. The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g. Cas1, Cas2, RNA nuclease), and/or one or more accessory proteins (e.g. Cas 4, DNA nuclease), CRISPR associated Rossman fold (CARF) domain containing proteins, and/or RNA transcriptase. Although Class 1 systems have limited sequence similarity, Class 1 system proteins can be identified by their similar architectures, including one or more Repeat Associated Mysterious Protein (RAMP) family subunits, e.g. Cas 5, Cas6, Cas7. RAMP proteins are characterized by having one or more RNA recognition motif domains. Large subunits (for example cas8 or cas10) and small subunits (for example, cas11) are also typical of Class 1 systems. See, e.g., FIGS. 1 and 2. Koonin E V, Makarova K S. 2019 Origins and evolution of CRISPR-Cas systems. Phil. Trans. R. Soc. B 374: 20180087, DOI: 10.1098/rstb.2018.0087. In one embodiment, Class 1 systems are characterized by the signature protein Cas3. The Cascade in particular Class1 proteins can comprise a dedicated complex of multiple Cas proteins that binds pre-crRNA and recruits an additional Cas protein, for example Cas6 or Cas5, which is the nuclease directly responsible for processing pre-crRNA. In one embodiment, the Type I CRISPR protein comprises an effector complex comprises one or more Cas5 subunits and two or more Cas7 subunits. Class 1 subtypes include Type I-A, I-B, I-C, I-U, I-D, I-E, and I-F, Type IV-A and IV-B, and Type III-A, III-D, III-C, and III-B. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al, the CRISPR Journal, v. 1, n5, FIG. 5.

Class 2 Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), Cas12d (CasY), Cas12e (CasX), Cas14, and/or CasΦ.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sep. 12; 154(6):1380-1389), Cas12 (Liu et al. Nature Communications, 8, 2095 (2017), and Cas13 (International Patent Publication Nos. WO 2019/005884 and WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Patent Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33(2): 139-142 and International Patent Publication WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein, "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C·G base pair into a T·A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Rees and Liu. 2018. Nat. Rev. Genet. 19(12): 770-788, particularly at FIGS. 1*b*, 2*a*-2*c*, 3*a*-3*f*, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471.

Other Example Type V base editing systems are described in International Patent Publication Nos. WO 2018/213708, WO 2018/213726, and International Patent Applications No. PCT/US2018/067207, PCT/US2018/067225, and PCT/US2018/067307, each of which is incorporated herein by reference.

In certain example embodiments, the base editing system may be an RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA base editor may be used to delete or introduce a post-translation modification site in the expressed mRNA. In contrast to DNA base editors, whose edits are permanent in the modified cell, RNA base editors can provide edits where finer, temporal control may be needed, for example in modulating a particular immune response. Example Type VI RNA-base editing systems are described in Cox et al. 2017. Science 358: 1019-1027, International Patent Publication Nos. WO 2019/005884, WO 2019/005886, and WO 2019/071048, and International Patent Application Nos. PCT/US20018/05179 and PCT/US2018/067207, which are incorporated herein by reference. An example FnCas9 system that may be adapted for RNA base editing purposes is described in International Patent Publication No. WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system. See e.g. Anzalone et al. 2019. Nature. 576: 149-157. Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion and combinations thereof. Generally, a prime editing system, as exemplified by PE1, PE2, and PE3 (Id.), can include a reverse transcriptase fused or otherwise coupled or associated with an RNA-programmable nickase and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRISPR-Cas systems along with few byproducts and greater or similar efficiency as compared to traditional CRISPR-Cas systems.

In some embodiments, the prime editing guide molecule can specify both the target polynucleotide information (e.g., sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576: 149-157, particularly at FIGS. 1*b*, 1*c*, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576: 149-157, particularly at pgs. 2-3, FIGS. 2a, 3a-3f, 4a-4b, Extended data FIGS. 3a-3b, 4, The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576: 149-157, particularly at pg. 3, FIG. 2a-2b, and Extended Data FIG. 5a-c.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on hosT-cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide refer to polynucleotides capable of guiding Cas to a target genomic locus and are used interchangeably as in foregoing cited documents such as International Patent Publication No. WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a hosT-cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and G M Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it being advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in International Patent Application No. PCT/US2019/045582, specifically paragraphs [0178]-[0333]. which is incorporated herein by reference.

Target Sequences, PAMs, and PFSs

Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

Exemplary Targets

In some embodiments the one or more target genes (or sequences) can be selected from the group of: LAMP2, PSMB8, TAP1, TAP2, ERAP1, CANX, CALR, TAPBP, PDIA3, CD74, HLA-DMA, HLA-DMB, HLA-DOA, TAPBPL, B2M, ERAP2, HLA-E, HLA-F, HLA-G, TLR4, MYD88, TICAM1, LNPEP, TFEB, RAB27A, SEC61A1, RAB3A, RAB3B, BCAP31, EEA1, LAMP1, RAB4A, RAB5A, RAB11A, RAB7A, RHOB, PKN1, PIK3C3, TF, WASF1, DIAPH1, SYK, ICAM1, and any combination thereof.

In some embodiments the one or more target gene(s) can be or include gene(s) that encode and/or regulate the function or activity of one or more lysosomal proteases (e.g. Cathepsins L, S, D, and/or B) involved in degrading antigens can be modified in the engineered APC.

In some embodiments, one or more target gene(s) can be or include gene(s) that encode and/or regulate the function or activity of one or more proteins involved in maintain the pH of the endosome can be modified in the engineered APC.

In some embodiments, the target gene(s) can be or include a gene that encodes a V-ATPase and/or one or more genes that can regulate V-ATPase activity in an APC.

In some embodiments, one or more target genes can be gene(s) that encode and/or regulate the function or activity of NOX2.

In some embodiments, one or more target gene(s) can include or be gene(s) that encode and/or regulate the activity and/or function of endocytosis receptors that can specifically target non-degradative endosomal compartments, such as a mannose receptor.

In some embodiments, one or more target gene(s) can include or be gene(s) that encode and/or regulate the activity and/or function of gamma-interferon-inducible lysosomal thiol reductase (GILT).

In some embodiments, one or more target gene(s) can include or be gene(s) that encode and/or regulate the activity and/or function of one or members of the ER associated degradation machinery, including but not limited to, AAA ATPase p97 and Sec61 and combinations thereof.

In some embodiments, one or more target gene(s) can include or be gene(s) that encode and/or regulate the activity and/or function of TAP.

In some embodiments, one or more target gene(s) can include or be gene(s) that encode and/or regulate the activity and/or function of ERAP and/or IRAP.

In some embodiments, one or more target gene(s) can include or be gene(s) that encode and/or regulate the activity and/or function of Rab11a.

In some embodiments, one or more target gene(s) can include or be gene(s) that encode and/or regulate the activity and/or function of a SNARE protein, including but not limited to, Sec22b and/or syntaxin 4. In some embodiments, one or more target gene(s) can include or be gene(s) that encode and/or regulate the activity and/or function of SNAP23. In some embodiments, one or more target gene(s) can include or be gene(s) that encode and/or regulate the activity and/or function of MyD88.

In some embodiments, one or more target gene(s) can include or be gene(s) that encode and/or regulate the activity and/or function of UNC93B1.

In some embodiments, one or more target gene(s) can include or be gene(s) that encode and/or regulate the activity and/or function of a molecule involved in a cell signaling pathway that regulate antigen presentation in an APC, including but not limited to, MAPK, MAPKKK, MAPKK, p38, INK, ERK1/2, MMK3, MKK6, protein kinase C family members (e.g. PKC alpha, beta (both I and II), atypical PKC ζ, and λ/ι, and novel (δ, ε, and θ), toll-like receptors (e.g. TLR-1, TLR2, TLR-4, TLR-5, TLR7, and TLR9), INF-gamma, TL-4, TNF-alpha, JAK, STAT (e.g. STAT3), Rho GTPases, Rho kinase and combinations thereof.

In some embodiments, one or more target gene(s) can include or be gene(s) that encode and/or regulate the activity and/or function of an HLA gene, including but not limited to HLA-A, HLA-B, HLA-C, HLA-E, HLA-F, and/or HLA-G.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table 1 (from Gleditzsch et al. 2019) below shows several Cas polypeptides and the PAM sequence they recognize.

TABLE 1

Example PAM Sequences

| Cas Protein | PAM Sequence |
|---|---|
| SpCas9 | NGG/NRG |
| SaCas9 | NGRRT or NGRRN |
| NmeCas9 | NNNNGATT |

TABLE 1-continued

Example PAM Sequences

| Cas Protein | PAM Sequence |
|---|---|
| CjCas9 | NNNNRYAC |
| StCas9 | NNAGAAW |
| Cas12a (Cpf1 (including LbCpf1 and AsCp1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein HisA, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: http://dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155(Pt. 3):733-740; Atschul et al. 1990. J. Mol. Biol. 215:403-410; Biswass et al. 2013 RNA Biol. 10:817-827; and Grissa et al. 2007. Nucleic Acid Res. 35:W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Nucleus Targeting and Transportation Sequences for CRISPR-Cas Systems

In some embodiments, one or more components (e.g., the Cas protein and/or deaminase) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO:1) or PKKKRKVEAS (SEQ ID NO:2); the NLS from nucleoplasmin (e.g., the nucleoplasmin bipartite NLS with the sequence KRPAATKKAGQAKKKK (SEQ ID NO:3)); the c-myc NLS having the amino acid sequence PAAKRVKLD (SEQ ID NO:4) or RQRRNELKRSP (SEQ ID NO:5); the hnRNPA1 M9 NLS having the sequence NQSSNFGPMKGGNFGGRSSGPYGGGGQYFAK-PRNQGGY (SEQ ID NO:6); the sequence RMRIZFKNKGKDTAELRRRRVEVSVELRKAKKD-EQILKRRNV (SEQ ID NO:7) of the IBB domain from importin-alpha; the sequences VSRKRPRP (SEQ ID NO:8) and PPKKARED (SEQ ID NO:9) of the myoma T protein; the sequence PQPKKKPL (SEQ ID NO:10) of human p53; the sequence SALIKKKKKMAP (SEQ ID NO:11) of mouse c-abl IV; the sequences DRLRR (SEQ ID NO:12) and PKQKKRK (SEQ ID NO:13) of the influenza virus NS1; the sequence RKLKKKIKKL (SEQ ID NO:14) of the Hepatitis virus delta antigen; the sequence REKKKFLKRR (SEQ ID NO:15) of the mouse Mx1 protein; the sequence KRKGDEVDGVDEVAKKKSKK (SEQ ID NO:16) of the human poly(ADP-ribose) polymerase; and the sequence RKCLQAGMNLEARKTKK (SEQ ID NO:17) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to a nucleotide deaminase or catalytic domain thereof. When such a guide forms a CRISPR complex (e.g., CRISPR-Cas protein binding to guide and target), the adapter proteins bind and the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+nucleotide deaminase (e.g. due to steric hindrance within the three-dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Recombination Templates

In some embodiments, the CRISPR-Cas system for include a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include a sequence that corresponds to both, a first site on the target sequence that is cleaved in a first Cas protein mediated event, and a second site on the target sequence that is cleaved in a second Cas protein mediated event.

In certain embodiments, the template nucleic acid can include a sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include a sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include a sequence which, when integrated, results in decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include a sequence which results in a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50,100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149).

Performing a Screen for Cross-Presentation

In some embodiments, a screen for cross-presentation as generally shown in FIG. 1 and discussed in greater detail in the Examples can be performed. In some embodiments, a lentivector library encoding guide RNAs (gRNA) and the transgenic B cell receptor (BCR) can be used to transduce APC cells, followed by antibiotic selection. Next in some embodiments, one or more a Cas protein, or polynucleotides and/or vector(s) encoding the same, can be appropriately delivered (e.g. by electroporation, retrovirus, RNP, or other suitable delivery and/or expression method) into the APCs cells to result in knockout APC cells. In some embodiments, these cells can then be trained with a peptide antigen that is optionally tagged with a marker peptide, and incubated with an anti-peptide-MHCI nanobody. The cells with bound fluorescent nanobody can then be sorted by flow cytometry into bins expressing higher or lower peptide-MHCI (green shaded peak) than wildtype cells and incubated with the same peptide. Finally, targeted next generation sequencing can be used to identify genes involved in higher or lower cross-presentation.

In some embodiments, the genes identified to result in higher or lower cross-presentation can be optionally modified in the engineered APC such that the desired level of cross-presentation is achieved. In some embodiments, this means modifying genes resulting in higher cross-presentation such that their expression and/or translation is reduced. In some embodiments, this means modifying genes resulting in higher cross-presentation such that their expression and/or translation is increased. In some embodiments, this means modifying genes resulting in lower cross-presentation such that their expression and/or translation is reduced. In some embodiments, this means modifying genes resulting in lower cross-presentation such that their expression and/or translation is increased. In some embodiments, a combination of the previous modifications can be used.

In some embodiments, an antigen presenting cell or engineered antigen presenting cell can be first engineered to express a BCR (if it does not already express on). Conventional recombinant engineering and gene modification techniques can be used to engineer the APC as needed. In some embodiments, the BCR can be an engineered BCR that is specific for a peptide marker (such as FLAG tag). Other peptide tags can also be used instead of FLAG and are generally known in the art. A target T-cell antigen can optionally be coupled to a peptide marker (e.g. FLAG) again using conventional recombinant engineering and peptide production techniques. The antigen can then be incubated with the engineered APC, where it can interact with the BCR or engineered BCR and be taken into the engineered APC. This can train the engineered APCs as noted above.

Alternatively, or additionally, cross-presentation genes can be identified by screening of a selected list of genes in primary human B cells, in the case thaT-cell numbers or viability represent the major limiting factors.

Alternatively, or additionally, cross-presentation genes can be identified by screening of a genome-wide library in 293T-cells, engineered to cross-present antibody-bound antigen by expression of FcγRIIA (Giodini et al. Proc. Natl. Acad. Sci. 106 (2009) 3324-3329. doi:10.1073/pnas.0813305106).

Engineered APCS can be analyzed to determine if they express a desired antigen presentation pathway signature.

The methods can involve determining the presence of modifications in the sample, which modifications result in altered expression of the gene or gene product involved in antigen presentation. Modifications in genes can be determined directly by methods such as but not limited to PCR, sequencing, gradient gel electrophoresis etc.

The methods as provided herein can include, detecting, in a biological sample of a patient, one or more genetic modifications to an antigen processing pathway gene. Methods for determining expression of a gene or a product thereof are known in the art and include, but are not limited to, methods of RNA detection, such as but not limited to Northern blotting, RT-qPCR, RNA sequencing and methods of protein detection, such as but not limited to Western blotting, ELISA, RIA, Histochemical detection etc. In particular embodiments, detection of expression is performed by immunohistochemistry. Antibodies suitable for immunological (e.g. immunohistochemical) detection of proteins involved in antigen processing pathway, such as BM2 or HLA proteins or any others discussed elsewhere herein, are typically commercially available or can be obtained by routine methods. Where the methods involve determining reduced expression, typically the expression of a gene involved in antigen processing pathway is quantified. In particular embodiments, the expression is quantified relative to a control sample for which expression is set at 100%. In particular embodiments, the reduction of expression is at least 20%, more particularly at least 50%, such as at least 90%. In further embodiments, the expression level is reduced to less than 80%, such as between 50-80%, or to less than 50%, such as between 0-50%, such as between 10-50%.

The pathways can be modified in the engineered APC, by modifying one or more genes in the pathways to obtain the desired presentation of antigen. Conventional recombinant and genetic modification techniques can be used and will be appreciated by those of ordinary skill in the art in view of this disclosure.

T-Cell Modulating Agents

The engineered APC can contain, produce, and/or deliver one or more T-cell modulating agents to one or more Target T-cells with which it interacts and/or binds in a target T-cell antigen specific manner. In some embodiments, the T-cell modulating agent can be delivered in such a manner that the T-cell modulating agent also can be delivered to one or more T-cells and/or other cells within effective proximity to the target T-cell. As used in this context, the term "deliver" refers to the transfer of a T-cell modulating agent from an engineered APC to a target T-cell and optionally a T- and/or other cells that are in effective proximity to the target T-cell. Transfer can include transfer through secretion or release of a T-cell modulating agent (e.g. by itself and via endosomes or other vesicles secreted by the engineered APC) by the engineered APC into the microenvironment surrounding the target T-cell and uptake by the target T-cell and optionally other cells within effective proximity to the target T-cell via any uptake mechanism (e.g. receptor-mediated uptake and endocytic mechanisms). Transfer can include transfer from the engineered APC via gap junctions formed by connexons between the engineered APC and target T-cell. Other mechanisms of transfer will be appreciated by those of ordinary skill in the art.

As used herein, the term "effective proximity" refers to the distance, region, or area surrounding a reference point or object in which a desired effect or activity occurs. The effective proximity can be determined by measuring the desired effect or activity in a representative number of species in the area surrounding the reference point or object. By way of non-limiting examples, an agent can be delivered to a specific point in a tissue of a subject and can be diffused through the surrounding tissue and cause effects in cells at a distance from the initial point of delivery. Cells that are affected by the agent can be determined and thus the region of effective proximity can be determined. Cells within that region are said to be within effective proximity to the initial delivery point. Similarly, if a cell is engineered to produce a product and secretes it into the surrounding environment, cells in the surrounding environment that are affected by the secreted product are said to be within effective proximity to the producing cell (or reference point). In some embodiments, effective proximity can range from 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000 microns or mm away from the reference point.

T-Cell Modulating Agents

T-cell modulating agents (also referred to interchangeably herein as "T-cell modulators", "T-cell modulating molecules," and the like) can be any agent that can modulate one or more characteristic, function, process, and/or activity of a T-cell. In some embodiments, the T-cell modulating agent can modulate only T-cells or a specific subset of T-cells. In some embodiments, the T-cell modulating agent can modulate T-cells and one or more other types of cells. As used herein, "agent" refers to any substance, compound, molecule, and the like, which can be biologically active or otherwise can induce a biological and/or physiological effect on a cell.

T-cell modulating agents can be agents that inhibit, eliminate, or reduce one or more one or more characteristic, function, process, and/or activity of a T-cell, such as a target T-cell. Such T-cell modulating agents can be referred to as T-cell inhibitory agents. It will be appreciated that some T-cell modulating agents are not specific to T-cells and can case effects on other cell types, such as those that can be in effective proximity to a target T-cell.

T-cell modulating agents can be agents that can stimulate, induce, increase, or otherwise activate one or more characteristics, function, process, and/or activity of a T-cell, such as a target T-cell. Such T-cell modulating agents are referred to herein as "T-cell stimulating agents."

T-cell modulating agents can include, but are not limited to, cytokines, chemokines, cytokine inhibitors, antibodies, hormones, immune checkpoint molecules, growth factors, peptides, polypeptides, lipids, and the like. In some embodiments, the T-cell modulating agent is a ligand for a receptor on a T-cell and/or a cell that is in effective proximity to a target T-cell.

Cytokines and chemokines can be pro-inflammatory or anti-inflammatory. Cytokines can include, but are not limited to, IL-1, IL-2, IL-1β, IL-6, Il-1ra, IL-4, IL-7, IL-10, IL-11, IL-12, IL-13, IL-15, IL-33, IL-21, IL-23, IL-27 CXCL8, IFNs (e.g. α, β, and γ), colony stimulating factors (e.g. granulocyte colony-stimulating factor and granulocyte-macrophage colony-stimulating factor), some growth factors (e.g. TGF-β and PGDF) and TNF-α. Chemokines can include, but are not limited to, C-C chemokines (e.g. RANTES, monocyte chemoattractant protein or MCP-1, monocyte inflammatory protein or MIP-1α, and MIP-1β), C-X-C chemokines (e.g. IL-8 also called growth related oncogene or GRO/KC), C chemokines (e.g. lymphotactin), and CXXXC chemokines (e.g fractalkine). Cytokine inhibitors can include soluble cytokine receptors, including but not limited to, Soluble TNF receptor p55 (sTNFRI or sTNFRp55), Soluble TNF receptor p75(sTNFRII or sTNFRP75), Soluble IL-1 receptor type 2 (sIL-1RII), and Membrane-bound IL-1 receptor type 2 (mIL-1RII), IL-18 binding protein (IL-18BP).

Immune Checkpoint Molecules

Immune checkpoints are inhibitory pathways that slow down or stop immune reactions and prevent excessive tissue damage from uncontrolled activity of immune cells.

As used herein, "checkpoint blockade (CPB) therapy" refers to therapy that inhibits the inhibitory pathways, allowing more extensive immune activity. Such therapy can comprise treatment with any small molecule chemical compound, antibody, nucleic acid molecule, or polypeptide, or fragment thereof, that inhibits the inhibitory pathways. "Checkpoint blockade therapy" may also refer to stimulation of a preexisting immune response. In certain embodiments, CPB therapy is therapy with an inhibitor of the programmed death-1 (PD-1) pathway, for example an anti-PD1 antibody, such as, but not limited to Nivolumab. In other embodiments, CPB therapy is therapy with an anti-cytotoxic T-lymphocyte-associated antigen (CTLA-4) antibody. In additional embodiments, the CPB therapy is targeted at another member of the CD28CTLA4 Ig superfamily such as BTLA, LAG3, ICOS, PDL1 or KIR (Page et al., Annual Review of Medicine 65:27 (2014)). In further additional embodiments, the CPB therapy is targeted at a member of the TNFR superfamily such as CD40, OX40, CD137, GITR, CD27 or TIM-3. In some cases, targeting a checkpoint inhibitor is accomplished with an inhibitory antibody or similar molecule. In other cases, it is accomplished with an agonist for the target; examples of this class include the stimulatory targets OX40 and GITR. Particularly preferred is CPB therapy comprising therapy with antibodies selected from anti-CTLA4, anti-PD1, anti-PDL1 antibodies and a combination thereof.

In some embodiments, the inhibitory checkpoint molecules are AA2AR, B7-H3, B7-H4, BTLA, CTLA-4, IDO, KIR, LAG3, NOX2, PD1, TIM-3, VISTA, SIGLEC7, or any combination thereof.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation.

In some embodiments, the stimulatory checkpoint molecules are CD27, CD28, CD40, CD122, CD137, OX40, GITR, ICOS or any combination thereof.

In some embodiments, the checkpoint molecule(s) can be selected from CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 TIM-, and combinations thereof.

T-Cell Death Inducing Molecules

In some embodiments, the T-cell modulating agent can be an agent that can induce T-cell death. Such T-cell modulating agents are referred to herein as "T-cell death inducing molecules." In some embodiments, the T-cell death inducing molecule(s) can interact with a target T-cell and/or a cell in effective proximity to a target T-cell and cause activation-induced cell death (AICD) in the target T-cell and/or a cell in effective proximity to a target T-cell (Linterman and Vinuesa. 2010. Progress in Molecular Biology and Translation Science. Vol. 92: 207-248; doi.org/10.1016/S1877-1173(10)92009-7). In some embodiments, the T-cell death inducing molecules can be TNF, CD95L (FasL or Fas ligand), TRAIL, TL1A, IL-2, CD-28 inhibitors, and combinations thereof. CD-28 is a co-stimulatory molecule that protects against ACICD. CD-28 inhibitors can include but are not limited to, soluble domains of CTLA-4 fused with an Ig Fc domain and others as described in Vanhove et al. 2017. Antibodies. 6, 19; doi:10.3390/antib6040019.

Dysfunctional T-Cell Modulating Agents

In some embodiments, the T-cell modulating agent can modulate a dysfunctional T-cell. In some embodiments the T-cell modulating agent capable of modulating a dysfunctional T-cell can be another agent described anywhere else herein. In some embodiments, the T-cell modulating agent capable of modulating a dysfunctional T-cell is an IL-27-induced gene molecule. In some embodiments, the IL-27-induced gene module can include Tim-3, Lag-3, TIGIT, IL-10, and combinations thereof.

In some embodiments, the T-cell modulating agent capable of modulating a dysfunctional T-cell is an ILT-3 ligand. Suitable ILT-3 ligands include, but are not limited to, integrin αvβ, CD166, ANGPT1, ANGPT2, ANGPT3, ANGPT4, ANGPTL1, ANGPTL2, ANGPTL3, ANGPTL4, ANGPTL5, ANGPTL6, ANGPTL7, ANGPTL8 and combinations thereof. In another embodiment of this embodiment the T-cell modulating agent comprises an antibody agent. In another embodiment of this embodiment the antibody agent comprises a variable region selected from the variable regions of ZM3.8, ZM4.1, 293622, and 293623. In another embodiment of this embodiment the T-cell modulating agent comprises a soluble variant of ILT-3. In another embodiment of this embodiment the soluble variant of ILT-3 comprises a polypeptide encoded by NM_001278430. In another embodiment of this embodiment the T-cell modulating agent inhibits the expression, activity and/or function of the ILT-3 gene or gene product or combination thereof. In another embodiment of this embodiment the T-cell modulating agent promotes or activates the expression, activity and/or function of the ILT-3 gene or gene product or combination thereof. In another embodiment of this embodiment the T-cell modulating agent inhibits binding of ILT-3 to one or more ILT-3 ligands. In another embodiment of this embodiment the one or more ILT-3 ligands is selected from integrin αvβ, CD166, ANGPT1, ANGPT2, ANGPT3, ANGPT4, ANGPTL1, ANGPTL2, ANGPTL3, ANGPTL4, ANGPTL5, ANGPTL6, ANGPTL7, and ANGPTL8.

In another embodiment of this embodiment the T-cell modulating agent inhibits the expression, activity and/or function of one or more genes selected from ANGPT1, ANGPT2, ANGPT3, ANGPT4, ANGPTL1, ANGPTL2, ANGPTL3, ANGPTL4, ANGPTL5, ANGPTL6, ANGPTL7, and ANGPTL8 or gene products thereof or combinations thereof.

In another embodiment of this embodiment the T-cell modulating agent promotes or activates the expression, activity and/or function of one or more genes selected from ANGPT1, ANGPT2, ANGPT3, ANGPT4, ANGPTL1, ANGPTL2, ANGPTL3, ANGPTL4, ANGPTL5, ANGPTL6, ANGPTL7, and ANGPTL8 or gene products thereof or combinations thereof.

In another embodiment of this embodiment the T-cell modulating agent promotes the expression, activity and/or function of the CD166 gene or gene product or combination thereof.

In another embodiment of this embodiment the T-cell modulating agent inhibits the expression, activity and/or function of the CD166 gene or gene product or combination thereof.

A T-cell modulating agent or agents can modulate the expression, activity and/or function of one or more target genes or gene products thereof selected from the target genes listed in Table 1-Table 13h of International Patent Application Publication WO/2018/067991 or any combination thereof.

In some embodiments, a T-cell modulating agent for dysfunctional T-cells can be IMP321, BMS-986106, LAG525, TSR022, MTIG7192A, TRX518, InCAGNO1876, GWN323, MEDI1873, MEDI9447, PF-0508526 (utomilumab), BMS-663513 (urelumab), MOXR0916, MED16469, MED16383, PF04518600, KHK4083.

In some embodiments, the T-cell modulating agent can be: an agonist of a cell molecule, such as a cell surface molecule, which when activated is capable of upregulating immune response, such as one or more of an agonist of 4-1BB, an agonist of OX40, an agonist of GITR, an agonist of STING, an agonist of TLR, or an agonist of BTLA; and/or an inhibitor of a cell molecule, such as a cell surface molecule, which when not inhibited is capable of down-regulating immune response, such as a checkpoint inhibitor, or such as one or more of an antagonist of PD1, an antagonist of CTLA4, an antagonist of BTLA, an antagonist of TIGIT, an antagonist of TIM3, an antagonist of LAG3, an antagonist of VISTA, an antagonist of LILRB4, an antagonist of CD160, an antagonist of CD274, or an antagonist of IDO.

In some embodiments, the T-cell modulating agent or agents are capable of modulating the expression, activity and/or function of an angiopoietin or angiopoietin-like protein.

Target T-Cells

In some embodiments, the target T-cell is a pathogenic T-cell. In some embodiments, the target T-cell is a non-pathogenic T-cell. The terms "pathogenic" or "non-pathogenic" as used herein are not to be construed as implying that one target T-cell phenotype is more desirable than the other. As described herein, there are instances in which modulating a pathogenic target T-cell or modulating the target T-cell phenotype towards a non-pathogenic target T-cell phenotype is desirable.

In some embodiments, the target T-cells are naïve T-cells. In some embodiments, the target T-cells are differentiated T-cells. In some embodiments, the target T-cells are partially differentiated T-cells. In some embodiments, the target T-cells are a mixture of naïve T-cells and differentiated T-cells. In some embodiments, the target T-cells are mixture of naïve T-cells and partially differentiated T-cells. In some embodiments, the target T-cells are mixture of partially differentiated T-cells and differentiated T-cells. In some embodiments, the target T-cells are mixture of naïve T-cells, partially differentiated T-cells, and differentiated T-cells.

In some embodiments, the target T-cell is a dysfunctional or exhausted T-cell. T-cell dysfunction or exhaustion is a state of T-cell differentiation that arises in chronic disease settings such as chronic viral infections and cancer. Dysfunctional T-cells exhibit diverse deficits in effector functions, including impaired proliferative capacity, cytotoxicity, and production of pro-inflammatory cytokines (Pardoll, D. M. (2012) Nature reviews. Cancer 12, 252-264; Wherry and Kurachi, (2015) Nature reviews Immunology 15, 486-499). Consequently, dysfunctional T-cells are poor mediators of both viral and tumor clearance. Dysfunctional T-cells express high levels of co-inhibitory receptors, such as Programmed cell death 1 (PD-1) and cytotoxic T-lymphocyte-associated protein 4 (CTLA-4), and blockade of these receptors is associated with recovery of effector T-cell responses in multiple experimental models of chronic viral infection. Exhausted T-cells have also been noted to be poor mediators of viral and/or tumor clearance and express high levels of co-inhibitory receptors, such as PD-1 and CTLA-4. Blockade of these receptors has been associated with the recovery of effector T-cell responses in experimental models of chronic viral infection and cancer (Leach, D. R., et al., (1996) Science 271, 1734-1736; Barber, D. L. et al., (2006) Nature 439, 682-687; Mahoney et al., (2015) Nature reviews Drug discovery 14, 561-584; Wherry and Kurachi, 2015). Indeed, therapeutic blockade of CTLA-4 and PD-1 has been successfully translated to the clinic for the treatment several human cancers (Hodi, F. S. et al., (2010) The New England journal of medicine 363, 711-723; Robert, C. et al., (2011) The New England journal of medicine 364, 2517-2526, Hamid, O. et al., (2013) The New England journal of medicine 369, 134-144; Topalian et al., (2012) The New England journal of medicine 366, 2443-2454).

CTLA-4 and PD-1 are not the only co-inhibitory receptors that are expressed by dysfunctional T-cells. In fact, as described herein, dysfunctional T-cells express multiple co-inhibitory receptors including T-cell immunoglobulin and mucin-domain containing-3 (Tim-3), Lymphocyte-activation gene 3 (Lag-3), and T-cell immunoreceptor with Ig and ITIM domains (TIGIT), indicating shared regulatory mechanisms driving their expression (Anderson et al., (2016) *Immunity* 44, 989-1004; Wherry and Kurachi, 2015). Importantly, as dysfunctional T-cells accumulate expression of co-inhibitory receptors, they develop a "deep" state of dysfunction and begin to produce IL-10, which further contributes to local immune suppression (Wherry, E. J. (2011) *Nature immunology* 12, 492-499).

Thus, the co-expression of co-inhibitory receptors on dysfunctional T-cells has important functional consequences. Indeed, combination therapies that simultaneously target multiple co-inhibitory pathways, such as CTLA-4 together with PD-1, or PD-1 together with TIM-3, LAG-3, or TIGIT, are more potent at restoring anti-tumor immunity than blockade of single co-inhibitory targets in both humans and in experimental mouse tumor models (Wolchok, J. D. et al. (2013) *The New England journal of medicine* 369, 122-133; Woo, S. R. et al. (2012) *Cancer research* 72, 917-927; Johnston, R. J. et al. (2014) *Cancer cell* 26, 923-937; Fourcade, J. et al. (2014) *Cancer research* 74, 1045-1055). Together these observations raise the important issue of understanding how co-inhibitory receptors are induced and co-regulated in exhausted or dysfunctional T-cells.

The extent of co-inhibitory receptor co-expression is directly correlated to the severity of dysfunctional phenotype (Wherry and Kurachi, 2015). Thus, combination therapies that simultaneously target multiple co-inhibitory pathways, such as PD-1 together with CTLA-4 are more efficacious at restoring anti-tumor immunity than blockade of single co-inhibitory targets in both mouse tumor models and patients (Fourcade et al., 2014; Johnston et al., 2014; Sakuishi et al., (2010) *The Journal of experimental medicine* 207, 2187-2194; Wolchok et al., 2013; Woo et al., 2012).

In some embodiments, the dysfunctional T-cell can have aberrant expression of a gene responsive to IL-27 or IL-27 signaling pathway (also referred to herein as an IL-27 gene module). In some embodiments, the IL-27-induced gene module can include Tim-3, Lag-3, TIGIT, IL-10, and combinations thereof. In some embodiments, an IL-27-induced gene module can be a T-cell modulating agent, such as for a dysfunctional T-cell, which are described in greater detail elsewhere herein. In some embodiments, an ILT-3 ligand can be a T-cell modulator, such as for a dysfunctional T-cell. Such T-cell modulating agents are described in greater detail elsewhere herein. Other dysfunctional T-cell modulating agents are described in greater detail elsewhere herein.

In one embodiment, provided herein is a method of modulating T-cell dysfunction, the method comprising contacting a dysfunctional T-cell with a modulating agent or agents that modulate the expression, activity and/or function of an angiopoietin or angiopoietin-like protein.

In another embodiment of this embodiment the T-cell dysfunction is T-cell exhaustion.

In another embodiment of this embodiment the modulation of T-cell exhaustion comprises a decrease in the exhausted T-cell phenotype, such that T-cell activation is increased.

In some embodiments, the target T-cell can be a Th17 cell. Th17 cells produce the pro-inflammatory cytokine and can, as a part of the adaptive immune system, Th17 cells mediate clearance of fungal infections, but they are also strongly implicated in the pathogenesis of autoimmunity (Korn et al., 2009). In mice, although Th17 cells are present at sites of tissue inflammation and autoimmunity (Korn et al., 2009), they are also normally present at mucosal barrier sites, where they maintain barrier functions without inducing tissue inflammation (Blaschitz and Raffatellu, 2010). In humans, functionally distinct Th17 cells have been described; for instance, Th17 cells play a protective role in clearing different types of pathogens like *Candida albicans* (Hernandez-Santos and Gaffen, 2012) or *Staphylococcus aureus* (Lin et al., 2009), and promote barrier functions at the mucosal surfaces (Symons et al., 2012), despite their pro-inflammatory role in autoimmune diseases such as rheumatoid arthritis, multiple sclerosis, psoriasis systemic lupus erythematous and asthma (Waite and Skokos, 2012). Thus, there is considerable diversity in the biological function of Th17 cells and in their ability to induce tissue inflammation or provide tissue protection. Th17 cells can be Th2 or Th1 cells.

As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T-cell that expresses Foxp3.

In some embodiments, the T-cell is a CD8+ T-cell.

In some embodiments, the T-cell is a CD4+ T-cell.

In some embodiments, the T-cell is a tumor infiltrating lymphocyte (TIL), T-cells specific for selected targets (such as antigens), such as malignanT-cells. In some embodiments, the T-cell specific for selected targets are CAR T-cells. Such cells have been developed and described in association with the adoptive cell transfer therapy for treatment of e.g. cancers. See Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T-cell response. Nat. Rev. Immunol. 12(4): 269-281; and Jenson and Riddell, 2014, Design and implementation of adoptive therapy with chimeric antigen receptor-modified T-cells. Immunol Rev. 257(1): 127-144, Poirot et al., 2015, Multiplex genome edited T-cell manufacturing platform for "off-the-shelf" adoptive T-cell immunotherapies, Cancer Res 75 (18): 3853). Various strategies may for example be employed to genetically modify T-cells by altering the specificity of the T-cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

TCR modifications, such as chimeric antigen receptors (CARs), can be used in order to generate immunoresponsive cells, such as T-cells, specific for selected targets, such as malignanT-cells, with a wide variety of receptor chimera constructs having been described (see e.g., U.S. Pat. Nos.

5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T-cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation by any of these techniques may for example include T-cells, Natural Killer (NK) cells, cytotoxic T lymphocytes (CTL), regulatory T-cells, human embryonic stem cells, tumor-infiltrating lymphocytes (TIL) or a pluripotent stem cell from which lymphoid cells may be differentiated. T-cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T-cells (which may for example be assayed by non-enzymatic digital array and/or multi-panel flow cytometry). All cells described herein can be target T-cells.

SynNotch Receptors

In some embodiments, the engineered APC can contain and/or express a SynNotch receptor. The SynNotch receptor can specifically bind and/or otherwise interact with a SynNotch receptor ligand. SynNotch receptor systems are programmable orthogonal receptor system that can couple binding, detection, or some other interaction with a specific ligand (e.g. a synNotch polypeptide) to an endogenous or engineered function in a cell. Each synNotch receptor can be composed of a core Notch domain flanked by modular extracellular and intracellular domains. Binding of a ligand to the synNotch receptor can trigger protease mediated cleavage of a transcription factor, which can be exogenous. In some embodiments, the SynNotch Receptor can be any SynNotch receptor or variant thereof as described in e.g. Roybal et al. 2016. Cell. Vol. 164(4):599-600; Morsut et al., 2016. Cell. 164:780-791; Roybal et al. Cell (2016) 167(2): 419-432, Roybal et al. Cell (2016) 164(4):770-779; U.S. Pat. App. Pub: 2019/0134093, 2018/0355011; 2018/0079812; 2016/0264665; 2018/0208636; 2017/0233474; 2019/0202918; US2019/0010245; US20190270991; US2018/0346589; US20190269728; U.S. Pat. Nos. 9,670,281; 9,834,608; International Pat. Pub.: WO/2017/1993059; WO/2016/138034; WO2019/175428; WO2019/141270; WO2019/178259; WO 2018/039247; WO/2019/10901; WO/2019/195586; WO/2018/222880; WO/2019/016526; WO/2019/19557; WO/2019/166877 the contents of which can be adapted for use with the engineered APCs described herein.

SynNotch receptors are synthetic receptors that can specifically bind or otherwise interact with a SynNotch ligands. In some embodiments, the synNotch ligand is not a soluble ligand. In some embodiments, the synNotch ligand is insoluble and bound to a cell membrane or membrane of a vesicle.

In some embodiments, a synNotch receptor is composed of at least in part an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a Notch receptor. In some instances, the Notch regulatory region of a Notch receptor polypeptide is a mammalian Notch regulatory region, including but not limited to e.g., a mouse Notch (e.g., mouse Notch1, mouse Notch2, mouse Notch3 or mouse Notch4) regulatory region, a rat Notch regulatory region (e.g., rat Notch1, rat Notch2 or rat Notch3), a human Notch regulatory region (e.g., human Notch1, human Notch2, human Notch3 or human Notch4), and the like or a Notch regulatory region derived from a mammalian Notch regulatory region and having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a mammalian Notch regulatory region of a mammalian Notch receptor amino acid sequence.

Such Notch regulatory regions can include or exclude various components (e.g., domains, cleavage sites, etc.) thereof. Examples of such components of Notch regulatory regions that may be present or absent in whole or in part, as appropriate, include e.g., one or more EGF-like repeat domains, one or more Linl2/Notch repeat domains, one or more heterodimerization domains (e.g., HD-N or HD-C), a transmembrane domain, one or more proteolytic cleavage sites (e.g., a furin-like protease site (e.g., an S1 site), an ADAM-family protease site (e.g., an S2 site) and/or a gamma-secretase protease site (e.g., an S3 site)), and the like. Notch receptor polypeptides may, in some instances, exclude all or a portion of one or more Notch extracellular domains, including e.g., Notch-ligand binding domains such as Delta binding domains. Notch receptor polypeptides may, in some instances, include one or more non-functional versions of one or more Notch extracellular domains, including e.g., Notch-ligand binding domains such as Delta-binding domains. Notch receptor polypeptides may, in some instances, exclude all or a portion of one or more Notch intracellular domains, including e.g., Notch Rbp-associated molecule domains (i.e., RAM domains), Notch Ankyrin repeat domains, Notch transactivation domains, Notch PEST domains, and the like. Notch receptor polypeptides may, in some instances, include one or more non-functional versions of one or more Notch intracellular domains, including e.g., non-functional Notch Rbp-associated molecule domains (i.e., RAM domains), non-functional Notch Ankyrin repeat domains, non-functional Notch transactivation domains, non-functional Notch PEST domains, and the like.

In some embodiments, one or more endogenous and/or engineered pathways present in the engineered APC can be activated or inhibited upon interaction/binding of a synNotch ligand to the synNotch receptor. In some embodiments, interaction/binding of the synNotch receptor by the synNotch ligand can stimulate generation and/or release of a T-cell modulator. In some embodiments, the synNotch ligand is expressed on the surface of a target T-cell. In some embodiments, the synNotch ligand is expressed on the surface of a cell or vesicle that is not a target T-cell.

Modular Extracellular Sensor Architecture (MESA) Receptors

In some embodiments, the engineered APC expresses and/or is capable of expressing one or more MESA receptors. MESA is a self-contained receptor and signal transduction platform that can be maximally orthogonal to native or engineered cellular process and includes independent, tunable protein modules that can enable optimization and straightforward engineered of additional MESA that can recognize additional ligands. See e.g. Daringer et al. 2014. ACS Synth Biol. 3(12):892-902; Schwarz et al. 2017 Nat. Chem. Biol. 13(2):202-209; International Pat. App. Pub. WO2018/081039; WO/2018/17585; WO/2013/022739; US. Pat. App. Pub. US2014023485; and U.S. Pat. No. 9,732,392, which can be adapted for use with the engineered APCs described herein. Binding of a ligand (a MESA receptor ligand) to the MESA receptor can induce singling via an orthogonal mechanism to regulate a target pathway, such as expression of a gene. Each MESA receptor can be composed of two engineered transmembrane proteins, one of which includes an intracellular protease domain and the other of which includes an intracellular transcription factor that is initially sequestered at the plasma membrane. The extracellular domains confer recognition of novel inputs (by substituting ligand-recognition domains) and regulation of novel outputs (by substituting the transcription factor domain).

In some embodiments, the ligand for a MESA receptor is a soluble ligand. In some embodiments, one or more endogenous and/or engineered pathways present in the engineered APC can be activated or inhibited upon interaction/binding of a ligand to a MESA receptor on the engineered APC. In some embodiments, interaction/binding of the MESA receptor by the MESA ligand can stimulate generation and/or release of a T-cell modulator. In some embodiments, the MESA ligand is expressed on the surface of a target T-cell. In some embodiments, the MESA ligand is expressed on the surface of a cell or vesicle that is not a target T-cell.

In some embodiments, the target T-cell expresses a MESA receptor and the T-cell modulator is secreted or expressed on the surface of the engineered APC.

Hemichannels

The engineered APCs can contain one or more hemichannels (also referred to as a connexon) that can be capable of interacting with another hemichannel on another cell to form a gap junction between the two cells and allow the transfer of material between cells or between the cytoplasm of one cell and the extracellular space. See e.g. Herve, Jean-Claude; Derangeon, Mickael (2012-09-01). "Gap-junction-mediated cell-to-cell communication". Cell and Tissue Research. 352: 21-31. doi:10.1007/s00441-012-1485-6 and Cheung, Giselle; Chever, Oana; Rouach, Nathalie (2014-11-04). "Connexons and Pannexons: Newcomers in Neurophysiology". Frontiers in Cellular Neuroscience. 8. doi:10.3389/fncel.2014.00348. PMC 4219455. Hemichannels are assemblies of 6 proteins called connexins. See e.g., Cheung, Giselle; Chever, Oana; Rouach, Nathalie (2014-11-04). "Connexons and Pannexons: Newcomers in Neurophysiology". Frontiers in Cellular Neuroscience. 8. doi:10.3389/fncel.2014.00348. PMC 4219455. In some embodiments, the APCs having hemichannels can form gap junctions with a target T-cell and deliver a T-cell modulator to the target T-cell. In some embodiments, the engineered APC can form a gap junction with another cell and obtain antigen or other molecules form the other cell.

Trogocytic Inducer

Trogocytosis is a process whereby lymphocytes (e.g. B, T and NK cells) that are conjugated to antigen presenting cells can extract surface molecules from these cells and express them on their own surface. See e.g., E. Joly and D. Hudrisier. 2003. Nature Immunol. 4:815; Dance. PNAS Sep. 3, 2019 116 (36) 17608-17610. The molecular reorganization that takes place between the lymphocyte and the APC is also referred to by the term of art "immunological synapse". Trogocytosis can be triggered when ta T-cell receptor (TCR) or B cell receptor (BCR) interacts with an antigen recognized on an antigen presenting cells.

In the context of the engineered APCs described herein, the engineered APCs can express and/or be capable of expressing a trogocytic inducer on the surface of the engineered APC. The trogocytic inducer can induce trogocytosis between the engineered APC and another cell, such as a T-cell or B-cell. In some embodiments, the other cell is a target T-cell. In some embodiments, T-cell modulators can be transferred from an engineered APC to a target T-cell through trogocytosis. Trogocytic inducers can include, but are not limited to, antigen receptors (e.g. MHC molecules) BCR and components thereof, TCR and components thereof, CD3, CD3 ligands, anti-CD3 molecules, CD28, CD28 ligands, anti-CD28 molecules, CD80/86, CD 80/86 ligands, anti-CD80/86 molecules, CD8 alpha and beta, CD2, CD2 ligands, anti-CD2 molecules, CD27, CD27 ligands, anti-CD27 molecules, CD9 ligands, CD9, anti-CD9 molecules, CD5, CD5 ligands, anti-CD5 molecules, anti-BCR kappa or mu chain antibodies, CD81, anti-CD81 antibodies, CD81 ligands, OVA peptide,), anti-MHCI molecules, anti-MHCII molecules, FcR gamma, See e.g. Hudrisier et al. J. Immunol. 2007. 178(6):3637-3647; Masuda et al., 2013. Clin. Development. Immunol. Article ID 345745, 6 pages, dx.doi.org/10.1155/2013/345745.

In some embodiments, the engineered APC can be engineered to express one or more trogocytic inducers where the engineered APC does not express the one or more trogocytic inducers. In some embodiments, trogocytosis can be induced by a target T-cell. In some of these embodiments, the target T-cell expresses one or more trogocytic inducers.

Self-Inactivation Molecules

The engineered APCs can be equipped with one or more self-inactivation molecules. These are also referred to in the art as "suicide genes". In some embodiments, the engineered APCs can include a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In some embodiments, the self-inactivation molecule system can be a cytosine deaminase/5-fluorocytosine system used alone or in combination with uracil phosphoribosyltransferase. In some embodiments, the self-inactivation molecule system can be an *E. coli* nitroreductase in combination with the prodrug CB1954, 5-[aziridin-1-yl]-2,4-dinitrobenzamide)(NTR)/CB1954) and/or purine nucleoside phosphorylase/9-([f]-M-2-deoxyerythropento-furanosyl) can also be used. In some embodiments, the engineered APC can be engineered to have a one or more genes that can promote cell death including cytochrome P450 2 B1, carboxylesterase, and cytosine deaminase, which are capable of converting cyclophosphamide, irinotecan, and 5-fluorocytosine, into active metabolites that can lead to cell death.

In use, the engineered APCs containing one or more self-inactivation molecules can be induced to self-inactivate by administering to the subject or cell population a signal molecule which can be taken in by cells or otherwise act upon the cells and lead to inactivation in engineered APCs containing the self-inactivation molecules. In some embodiments, the signal can induce apoptosis. In some embodiments, the signal molecule can be broken down by a self-inactivation molecule or gene product by the engineered APC into an active metabolite or other compound that leads to cell death or inactivation.

Formulations

The engineered APCs or component thereof can be included in a formulation that can be delivered to a subject or cell. In some embodiments, the formulation is a pharmaceutical formulation. One or more of the polypeptides, polynucleotides, vectors, cells, and combinations thereof described herein can be provided to a subject in need thereof or a cell alone or as an active ingredient, such as in a pharmaceutical formulation. As such, also described herein are pharmaceutical formulations containing an amount of one or more of the polypeptides, polynucleotides, vectors, cells, and combinations thereof described herein. In some embodiments, the pharmaceutical formulation can contain an effective amount of the one or more of the polypeptides, polynucleotides, vectors, cells, and combinations thereof described herein. The pharmaceutical formulations described herein can be administered to a subject in need thereof or a cell.

In some embodiments, the amount of the one or more of the polypeptides, polynucleotides, vectors, cells, virus particles, nanoparticles, other delivery particles, and combinations thereof described herein contained in the pharmaceutical formulation can range from about 1 pg/kg to about 10 mg/kg based upon the bodyweight of the subject in need thereof or average bodyweight of the specific patient population to which the pharmaceutical formulation can be administered. The amount of the one or more of the polypeptides, polynucleotides, vectors, cells, and combinations thereof described herein in the pharmaceutical formulation can range from about 1 pg to about 10 g, from about 10 nL to about 10 ml. In embodiments where the pharmaceutical formulation contains one or more cells, the amount can range from about 1 cell to $1\times10^2$, $1\times10^3$, $1\times10^4$, $1\times10^5$, $1\times10^6$, $1\times10^7$, $1\times10^8$, $1\times10^9$, $1\times10^{10}$ or more cells. In embodiments where the pharmaceutical formulation contains one or more cells, the amount can range from about 1 cell to $1\times10^2$, $1\times10^3$, $1\times10^4$, $1\times10^5$, $1\times10^6$, $1\times10^7$, $1\times10^8$, $1\times10^9$, $1\times10^{10}$ or more cells per nL, µL, mL, or L.

Pharmaceutically Acceptable Carriers and Auxiliary Ingredients and Agents

In embodiments, the pharmaceutical formulation containing an amount of one or more of the polypeptides, polynucleotides, vectors, cells, virus particles, nanoparticles, other delivery particles, and combinations thereof described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to an amount of one or more of the engineered APCs described herein, the pharmaceutical formulation can also include an effective amount of an auxiliary active agent, including but not limited to, polynucleotides, amino acids, peptides, polypeptides, antibodies, aptamers, ribozymes, hormones, immunomodulators, antipyretics, anxiolytics, antipsychotics, analgesics, antispasmodics, anti-inflammatories, anti-histamines, anti-infectives, chemotherapeutics, and combinations thereof.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eicosanoids (e.g. arachidonic acid, lipoxins, and prostaglandins), and steroid hormones (e.g. estradiol, testosterone, tetrahydro testosterone Cortisol). Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-K, IFN-ω, and IFN-γ), granulocyte colony-stimulating factor, and imiquimod), chemokines (e.g. CCL3, CCL26 and CXCL7) cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylate, and sodium salicylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotonergic antidepressants (e.g. selective serotonin reuptake inhibitors, tricyclic antidepressants, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromperidol, droperidol, haloperidol, moperone, pipamperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzapine, paliperidone, perospirone, quetiapine, remoxipride, risperidone, sertindole, trimipramine, ziprasidone, zotepine, alstonia, bifeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, nonsteroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupirtine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papaverine, cyclobenzaprine, carisoprodol, orphenadrine, tizanidine, metaxalone, methocarbamol, chlorzoxazone, baclofen, dantrolene, baclofen, tizanidine, and dantrolene. Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, H1-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocetirizine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g. cimetidine, famotidine, lafutidine, nizatidine, raniltidline, and roxatidine), tritoqualine, catechin, cromoglicate, nedocromil, and p2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, albendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proguanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, abacavir/lamivudine/zidovudine, lamivudine/zidovudine, emtricitabine/tenofovir, emtricitabine/lopinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delavirdine, nevirapine, entecavir, lamivudine, adefovir, sofosbuvir, didanosine, tenofovir, abacavir, zidovudine, stavudine, emtricitabine, zalcitabine, telbivudine, simeprevir, boceprevir, telaprevir, lopinavir/ritonavir, fosamprenavir, darunavir, ritonavir, tipranavir, atazanavir, nelfinavir, amprenavir, indinavir, saqulnavir, ribavirin, valacyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, ceftizoxime, and ceftazidime), glycopeptide antibiotics (e.g. vancomycin, dalbavancin, oritavancin, and telavancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erythromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfisoxazole), tetracyclines (e.g. doxycycline, demeclocycline, minocycline, doxycycline/salicylic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, Cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparaginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylate, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, adotrastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In embodiments where there is an auxiliary active agent contained in the pharmaceutical formulation in addition to the one or more of the polypeptides, polynucleotides, CRISPR-Cas complexes, vectors, cells, virus particles, nanoparticles, other delivery particles, and combinations thereof described herein, amount, such as an effective amount, of the auxiliary active agent will vary depending on the auxiliary active agent. In some embodiments, the amount of the auxiliary active agent ranges from 0.001 micrograms to about 1 milligram. In other embodiments, the amount of the auxiliary active agent ranges from about 0.01 IU to about 1000 IU. In further embodiments, the amount of the auxiliary active agent ranges from 0.001 mL to about 1 mL. In yet other embodiments, the amount of the auxiliary active agent ranges from about 1% w/w to about 50% w/w of the total pharmaceutical formulation. In additional embodiments, the amount of the auxiliary active agent ranges from about 1% v/v to about 50% v/v of the total pharmaceutical formulation. In still other embodiments, the amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the targeted effector fusion protein and/or complex thereof or composition containing the one or more of the polypeptides, polynucleotides, vectors, cells, and combinations thereof described herein. The oral dosage form can be administered to a subject in need thereof.

Where appropriate, the dosage forms described herein can be microencapsulated.

The dosage form can also be prepared to prolong or sustain the release of any ingredient. In some embodiments, the one or more of the polypeptides, polynucleotides, vectors, cells, and combinations thereof described herein can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Welterstadt, Germany), zein, shellac, and polysaccharides.

Coatings may be formed with a different ratio of water-soluble polymer, water insoluble polymers, and/or pH dependent polymers, with or without water insoluble/water soluble non-polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the one or more of the polypeptides, polynucleotides, vectors, cells, and combinations thereof described herein can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the one or more of the polypeptides, polynucleotides, vectors, cells, and combinations thereof described herein is contained in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g. the one or more of the polypeptides, polynucleotides, vectors, cells, and combinations thereof described herein and/or auxiliary active agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the one or more of the polypeptides, polynucleotides, vectors, cells, and combinations thereof described herein and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of one or more of the polypeptides, polynucleotides, vectors, cells, and combinations thereof described herein. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the one or more of the polypeptides, polynucleotides, vectors, cells, and combinations thereof described herein, an auxiliary active ingredient, and/or pharmaceutically acceptable salt thereof, such a dosage form can contain a powder base such as lactose, glucose, trehalose, manitol, and/or starch. In some of these embodiments, the one or more of the polypeptides, polynucleotides, vectors, cells, and combinations thereof described herein is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the one or more of the polypeptides, polynucleotides, vectors, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, gingival, subgingival, intrathecal, intravitreal, intracerebral, and intracerebroventricular) can include aqueous and/or non-aqueous sterile injection solutions, which can contain anti-oxidants, buffers, bactriostatic, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or nonaqueous sterile solutions that can optionally be adapted for injection, and which can optionally contain anti-oxidants, buffers, bacteriostats, solutes that render the composition isotonic with the eye or fluid contained therein or around the eye of the subject, and aqueous and nonaqueous sterile suspensions, which can include suspending agents and thickening agents.

For some embodiments, the dosage form contains a predetermined amount of the one or more of the polypeptides, polynucleotides, vectors, cells, and combinations thereof described herein per unit dose. In some embodiments, the predetermined amount of the Such unit doses may therefore be administered once or more than once a day. Such pharmaceutical formulations may be prepared by any of the methods well known in the art.

Kits

Also described herein are kits that contain one or more of the one or more of the polypeptides, polynucleotides, vectors, cells, or other components described herein and combinations thereof and pharmaceutical formulations described herein. In embodiments, one or more of the polypeptides, polynucleotides, vectors, cells, and combinations thereof described herein can be presented as a combination kit. As used herein, the terms "combination kit" or "kit of parts" refers to the compounds, or formulations and additional components that are used to package, screen, test, sell, market, deliver, and/or administer the combination of elements or a single element, such as the active ingredient, contained therein. Reagents, tools, and/or instructions for performing the methods described herein can be provided in a kit. For example, the kit can contain reagents, tools, and instructions for detecting and/or isolating antigen presenting cells in patient samples. Such a kit can include reagents for collecting a tissue sample from a patient, such as by biopsy, and reagents for processing the tissue. The kit can also include one or more reagents for performing a FACS analysis and/or gene or gene product expression analysis, such as reagents for performing nucleic acid amplification (e.g RT-PCR, qPCR), sequencing (e.g. next generation sequencing, whole exome sequencing), northern blot, proteomic analysis, or immunohistochemistry to determine expression levels of gene or gene product markers in a sample of a patient. For example, primers for performing RT-PCR, probes for performing northern blot analyses, and/or antibodies for performing proteomic analysis such as Western blot, immunohistochemistry and ELISA analyses can be included in such kits. Appropriate buffers for the assays can also be included. Detection reagents required for any of these assays can also be included. The appropriate reagents and methods are described in further detail below. The kits may include suitable primers and/or probes to detect the expression levels of at least one (up to all) of the genetic modifications disclosed herein. Where expression is determined at the protein level, the kit may contain binding reagents specific for the proteins of interest. The binding reagents may comprise antibodies to include all fragments and derivatives thereof. In the context of the various embodiments of the present invention the term "antibody" includes all immunoglobulins or immunoglobulin-like molecules with specific binding affinity for the relevant protein (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant protein. These derivatives and fragments may include Fab fragments, F(ab')2 fragments, Fv fragments, single chain antibodies, single domain antibodies, Fc fragments etc. The term "antibody" encompasses antibodies comprised of both heavy and light chains, but also heavy chain (only) antibodies (which may be derived from various species of cartilaginous fish or camelids). In specific embodiments, the antibodies may be engineered so as to be specific for more than protein, for example bi-specific to permit binding to two different target proteins.

In some embodiments, the kits may also contain a specific therapeutic agent to be administered to a subject in need thereof and/or engineer an APC isolated from a subject to generate an engineered APC described herein that can be administered to the subject as an adoptive cell therapy. This agent may be provided in a form, such as a dosage form, that is tailored to the specific treatment. The kit may be provided with suitable instructions for administration according to an appropriate treatment regimen.

The kit can include one or more reagents for modifying an antigen presentation pathway in an isolated antigen presenting cell.

The kits featured herein can also include an instruction sheet describing how to perform the assays for measuring gene or gene product expression. The instruction sheet can also include instructions for how to determine a reference cohort, including how to determine expression levels of gene or gene product markers in the reference cohort and how to assemble the expression data to establish a reference for comparison to a test patient or reference cell. The instruction sheet can also include instructions for e.g. isolating one or more antigen presenting cells from a subject, modifying one or more antigen presentation pathways in the isolated cell, presenting an antigen in the engineered APC, and/or delivering said engineered APC to the subject in need thereof. The instructions can also include directions for assaying gene or gene product expression in a test patient and for comparing the expression level with the expression in the reference cohort to subsequently determine the appropriate gene(s) in an antigen presentation pathway and/or T-cell regulators to engineer the APC to produce and/or express. Methods for determining the appropriate chemotherapy are described above and can be described in detail in the instruction sheet.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about isolating APCs from a subject, culturing and clonally expanding the APCs, modifying one or more antigen presentation pathways in the APCs, engineering the APCs to include or be capable of producing one or more T-cell antigens, processing and expressing one or more target T-cell antigens in an MHC of the engineered APCs, and/or performing a gene expression analysis and interpreting the results, and the like The kit can also include instructions in a tangible medium of expression that can contain information and/or directions regarding the content of the components and/or formulations contained therein, safety information regarding the content of the components(s) and/or formulation(s) contained therein, information regarding the amounts, dosages, indications for use, screening methods, component design recommendations and/or information, recommended treatment regimen(s) for the components(s) and/or formulations contained therein. As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory drive or CD-ROM or on a server that can be accessed by a user via, e.g. a web interface.

Methods of Making an Engineered Antigen Presenting Cell

Generally, the engineered antigen presenting cells can be made by isolating one or more native antigen presenting cells, such as a professional antigen presenting cell using an appropriate method (e.g. FACS), modifying an antigen presentation pathway (e.g. a cross-presentation, MHCI restricted presentation pathway, and/or MHCII restricted presentation pathway), and loading and/or expressing an extracellular and/or intracellular target T-cell antigen in the engineered APC. In some embodiments, the isolated and/or engineered APCs can be clonally expanded in vitro/ex vivo. In some embodiments, such as those where the engineered APCs are engineered to express a target T-cell specific antigen, the engineered APCs can be clonally expanded after being engineered to express the target T-cell specific antigen. Methods of modifying an antigen presentation pathway are described in greater detail elsewhere herein and can be employed to generate the engineered APCs. Methods of clonal expansion of immune cells, such as antigen presenting cells, are generally known in the art, and can be employed to clonally expand the cells, such as the engineered APCs and/or isolated APCs described herein.

As previously described, the engineered APCs can process and express a target T-cell specific antigen. In some embodiments, the target T-cell antigen is an extracellular antigen and can be loaded into the engineered APC via a cell surface receptor (e.g. a B cell receptor), or other intake mechanism (e.g. phagocytosis). In some embodiments, the extracellular antigen can be a recombinant polypeptide or peptide extracellular antigen that is composed of a polypeptide or peptide antigen coupled to a peptide epitope marker (e.g. FLAG, His, Myc, and the like). In some embodiments, the engineered APC can be engineered to express a modified cell surface receptor, such as a modified B-cell receptor, that is modified to specifically recognize the peptide epitope marker of the recombinant polypeptide or peptide extracellular antigen. This can facilitate uptake efficiency of the extracellular antigen.

The term "antigen loading" as used throughout this specification refers to a method or process of delivering one or more antigens to immune cells, such as particularly to the engineered antigen-presenting cells described herein, such that the antigenic epitopes of the antigen(s) are presented on MHC, whether intracellular or on the immune cell surface. Typically, the engineered APCs may be loaded with antigen (s) by a process comprising contacting or incubating the engineered APCs in vitro/ex vivo with a composition comprising the antigen(s) or a composition comprising nucleic acid(s) encoding the antigen(s) under conditions that permit the engineered APC to contact, express (if needed), process and present the antigen(s) on MHC. The skilled person will know the incubation temperature and time periods sufficient to allow for effective loading of antigens. For example, incubation steps may be typically from between about 1 to about 2 or about 4 hours, at temperatures of between about 25° C. to about 37° C. and/or may be overnight at about 4° C., and the like. By means of an example, the engineered APCs may be contacted with a composition comprising an isolated antigen, for example, an antigen isolated from a naturally-occurring source of the antigen, or an antigen produced recombinantly by a suitable host or hosT-cell expression system and isolated therefrom (e.g., a suitable bacterial, yeast, fungal, plant or animal host or hosT-cell expression system), or produced recombinantly by cell-free transcription or translation, or non-biological nucleic acid or peptide synthesis. By means of another example, the engineered APCs may be contacted with a composition comprising a naturally-occurring source of the antigen, i.e., substantially without isolating the antigen from said naturally-occurring source. For instance, the immune cells may be contacted with a composition comprising cells which naturally express the antigen or cell debris of such cells, e.g., tumor cells expressing tumour antigen(s). Suitably, such cells may be rendered non-viable and preferably lysed, for example, killed and preferably lysed by a mechanical, chemical or physical treatment, such as heat killed, apoptotic, necrotic or otherwise processed. By means of a further example, the engineered APCs cells may be contacted with cells of a suitable host or hosT-cell expression system which recombinantly produce the antigen, i.e., substantially without isolating the antigen from said cells. Suitably, such cells may be rendered non-viable and preferably lysed, for example, killed and preferably lysed by a mechanical, chemical or physical treatment, such as heat killed or otherwise processed.

Engineered APCs may also be loaded with an antigen by introducing into the immune cells a nucleic acid, commonly a recombinant nucleic acid, encoding the target T-cell antigen, whereby the engineered APCs express the target T-cell antigen intracellularly. Such an approach can yield an "intracellular antigen" that can be processed and presented via cellular mechanisms present in the engineered APC for processing and presenting intracellular antigens. Nucleic acid vectors and delivery systems are generally known in the art.

In some embodiments the engineered APCs can be incubated, expanded, and/or otherwise cultured in the presence of one or more cells from a subject, such as a subject in need thereof. The subjecT-cells can be diseased cells. In some embodiments, the diseased cells can be autoreactive immune cells. In some embodiments, the diseased cells can be tumor cells. In some embodiments, the diseased cells can be cancer cells. The subjecT-cells can be obtained by any suitable sample obtained from the subject. The engineered APC can internalize antigens from the subjecT-cells and process and present them on the surface of the APC. In this way, the engineered APCs can interact with T-cells targeting the subjecT-cells (e.g. those T-cells that have TCRs specific to the subjecT-cell antigens presented by the engineered APCS). In some embodiments, the engineered APCs can modify the response these target T-cells towards the subjecT-cells in vivo.

As discussed herein the engineered APCs or antigen can be modified. Various recombinant polynucleotide techniques can be used to generate engineered constructs and used to modify the cells described herein and/or to produce a recombinant antigen. Such techniques are now discussed in greater detail. It will be appreciated that the methods of

Vectors

Also provided herein are vectors that can contain one or more of engineered APC polynucleotides or antigen polynucleotides described herein. As used herein the term "engineered APC polynucleotides" refers to any polynucleotide that can be used to generate one or more modifications in an antigen presenting cells to produce the engineered APCs described herein. As used herein "antigen polynucleotides" refers to any polynucleotide that can encode a target T-cell antigen described herein. Such modifications are described elsewhere herein. In embodiments, the vector can contain one or more polynucleotides encoding one or more elements of engineered APC and/or antigen described herein. The vectors can be useful in producing bacterial, fungal, yeast, planT-cells, animal cells, and transgenic animals that can express one or more components of the engineered APC polynucleotides or antigen polynucleotides described herein. Within the scope of this disclosure are vectors containing one or more of the polynucleotide sequences described herein. One or more of the polynucleotides that are part of the engineered APC or antigen described herein can be included in a vector or vector system. The vectors and/or vector systems can be used, for example, to express one or more of the polynucleotides in a cell, such as a producer cell, to engineered APC polynucleotide or antigen polynucleotide virus delivery particles described elsewhere herein. Other uses for the vectors and vector systems described herein are also within the scope of this disclosure. In general, and throughout this specification, the term "vector" refers to a tool that allows or facilitates the transfer of an entity from one environment to another. In some contexts which will be appreciated by those of ordinary skill in the art, "vector" can be a term of art to refer to a nucleic acid molecule capable of transporting another nucleic acid to which it has been linked. A vector can be a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a hosT-cell. Certain vectors are capable of autonomous replication in a hosT-cell into which they are introduced (e.g. bacterial vectors having a bacterial origin of replication and episomal mammalian vectors). Other vectors (e.g., non-episomal mammalian vectors) are integrated into the genome of a hosT-cell upon introduction into the hosT-cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can be composed of a nucleic acid (e.g. a polynucleotide) of the invention in a form suitable for expression of the nucleic acid in a hosT-cell, which means that the recombinant expression vectors include one or more regulatory elements, which can be selected on the basis of the hosT-cells to be used for expression, that is operatively-linked to the nucleic acid sequence to be expressed. Within a recombinant expression vector, "operably linked" and "operatively-linked" are used interchangeably herein and further defined elsewhere herein. In the context of a vector, the term "operably linked" is intended to mean that the nucleotide sequence of interest is linked to the regulatory element(s) in a manner that allows for expression of the nucleotide sequence (e.g., in an in vitro transcription/translation system or in a hosT-cell when the vector is introduced into the hosT-cell). Advantageous vectors include lentiviruses and adeno-associated viruses, and types of such vectors can also be selected for targeting particular types of cells. These and other embodiments of the vectors and vector systems are described elsewhere herein.

In some embodiments, the vector can be a bicistronic vector. In some embodiments, a bicistronic vector can be used for one or more elements of the engineered APCs and/or antigens described herein. In some embodiments, expression of elements of the e engineered APCs and/or antigens described herein can be driven by the CBh promoter. Where the element of the engineered APCs and/or antigen is an RNA, its expression can be driven by a Pol III promoter, such as a U6 promoter. In some embodiments, the two are combined.

Cell-Based Vector Amplification and Expression

Vectors can be designed for expression of one or more elements of the engineered APCs and/or antigens described herein (e.g. nucleic acid transcripts, proteins, enzymes, and combinations thereof) in a suitable hosT-cell. In some embodiments, the suitable hosT-cell is a prokaryotic cell. Suitable hosT-cells include, but are not limited to, bacterial cells, yeasT-cells, insecT-cells, and mammalian cells. The vectors can be viral-based or non-viral based. In some embodiments, the suitable hosT-cell is a eukaryotic cell. In some embodiments, the suitable hosT-cell is a suitable bacterial cell. Suitable bacterial cells include, but are not limited to, bacterial cells from the bacteria of the species *Escherichia coli*. Many suitable strains of *E. coli* are known in the art for expression of vectors. These include, but are not limited to Pir1, Stbl2, Stbl3, Stbl4, TOP10, XL1 Blue, and XL10 Gold. In some embodiments, the hosT-cell is a suitable insecT-cell. Suitable insecT-cells include those from *Spodoptera frugiperda*. Suitable strains of *S. frugiperda* cells include, but are not limited to, Sf9 and Sf21. In some embodiments, the hosT-cell is a suitable yeasT-cell. In some embodiments, the yeasT-cell can be from *Saccharomyces cerevisiae*. In some embodiments, the hosT-cell is a suitable mammalian cell. Many types of mammalian cells have been developed to express vectors. Suitable mammalian cells include, but are not limited to, HEK293, Chinese Hamster Ovary Cells (CHOs), mouse myeloma cells, HeLa, U2OS, A549, HT1080, CAD, P19, NIH 3T3, L929, N2a, MCF-7, Y79, SO-Rb50, HepG G2, DIKX-X11, J558L, Baby hamster kidney cells (BHK), and chicken embryo fibroblasts (CEFs). Suitable hosT-cells are discussed further in Goeddel, GENE EXPRESSION TECHNOLOGY: METHODS IN ENZYMOLOGY 185, Academic Press, San Diego, Calif. (1990).

In some embodiments, the vector can be a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeasT-cell. Many suitable yeast expression vectors and features thereof are known in the art; for example, various vectors and techniques are illustrated in in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors can contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2 plasmids, yeast integrative plasmids, yeast replicative plasmids, shuttle vectors, and episomal plasmids.

In some embodiments, the vector is a baculovirus vector or expression vector and can be suitable for expression of polynucleotides and/or proteins in insecT-cells. Baculovirus vectors available for expression of proteins in cultured insecT-cells (e.g., SF9 cells) include the pAc series (Smith, et al., 1983. Mol. Cell. Biol. 3: 2156-2165) and the pVL series (Luckow and Summers, 1989. Virology 170: 31-39). rAAV (recombinant Adeno-associated viral) vectors are preferably produced in insecT-cells, e.g., *Spodoptera frugiperda* Sf9 insecT-cells, grown in serum-free suspension culture. Serum-free insecT-cells can be purchased from commercial vendors, e.g., Sigma Aldrich (EX-CELL 405).

In some embodiments, the vector is a mammalian expression vector. In some embodiments, the mammalian expression vector is capable of expressing one or more polynucleotides and/or polypeptides in a mammalian cell. Examples of mammalian expression vectors include, but are not limited to, pCDM8 (Seed, 1987. Nature 329: 840) and pMT2PC (Kaufman, et al., 1987. EMBO J. 6: 187-195). The mammalian expression vector can include one or more suitable regulatory elements capable of controlling expression of the one or more polynucleotides and/or proteins in the mammalian cell. For example, commonly used promoters are derived from polyoma, adenovirus 2, cytomegalovirus, simian virus 40, and others disclosed herein and known in the art. More detail on suitable regulatory elements are described elsewhere herein.

For other suitable expression vectors and vector systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T-cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments can utilize viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element can be operably linked to one or more elements of an engineered APCs and/or antigens so as to drive expression of the one or more elements of the engineered APCs and/or antigens described herein.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a hosT-cell or host organism.

In some embodiments, the vector can be a fusion vector or fusion expression vector. In some embodiments, fusion vectors add a number of amino acids to a protein encoded therein, such as to the amino terminus, carboxy terminus, or both of a recombinant protein. Such fusion vectors can serve one or more purposes, such as: (i) to increase expression of recombinant protein; (ii) to increase the solubility of the recombinant protein; and (iii) to aid in the purification of the recombinant protein by acting as a ligand in affinity purification. In some embodiments, expression of polynucleotides (such as non-coding polynucleotides) and proteins in prokaryotes can be carried out in *Escherichia coli* with vectors containing constitutive or inducible promoters directing the expression of either fusion or non-fusion polynucleotides and/or proteins. In some embodiments, the fusion expression vector can include a proteolytic cleavage site, which can be introduced at the junction of the fusion vector backbone or other fusion moiety and the recombinant polynucleotide or protein to enable separation of the recombinant polynucleotide or protein from the fusion vector backbone or other fusion moiety subsequent to purification of the fusion polynucleotide or protein. Such enzymes, and their cognate recognition sequences, include Factor Xa, thrombin and enterokinase. Example fusion expression vectors include pGEX (Pharmacia Biotech Inc; Smith and Johnson, 1988.

Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion E. coli expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, one or more vectors driving expression of one or more elements of an engineered APC and/or antigen described herein are introduced into a hosT-cell such that expression of the elements of the engineered delivery system described herein direct formation of an engineered APC and/or antigen described herein. For example, different elements of the engineered APC and/or antigen described herein can each be operably linked to separate regulatory elements on separate vectors. RNA(s) of different elements of the engineered delivery system described herein can be delivered to an animal or mammal or cell thereof to produce an animal or mammal or cell thereof that constitutively or inducibly or conditionally expresses different elements of the engineered APC and/or antigen described herein that incorporates one or more elements of the engineered APC and/or antigen described herein or contains one or more cells that incorporates and/or expresses one or more elements of the engineered delivery system described herein.

In some embodiments, two or more of the elements expressed from the same or different regulatory element(s), can be combined in a single vector, with one or more additional vectors providing any components of the system not included in the first vector. engineered APC and/or antigen polynucleotides that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. =In some embodiments, a single promoter drives expression of a transcript encoding one or more engineered APC and/or antigen proteins, embedded within one or more intron sequences (e.g., each in a different intron, two or more in at least one intron, or all in a single intron). In some embodiments, the engineered APC and/or antigen polynucleotides can be operably linked to and expressed from the same promoter.

Vector Features

The vectors can include additional features that can confer one or more functionalities to the vector, the polynucleotide to be delivered, a virus particle produced there from, or polypeptide expressed thereof. Such features include, but are not limited to, regulatory elements, selectable markers, molecular identifiers (e.g. molecular barcodes), stabilizing elements, and the like. It will be appreciated by those skilled in the art that the design of the expression vector and additional features included can depend on such factors as the choice of the hosT-cell to be transformed, the level of expression desired, etc.

Regulatory Elements

In embodiments, the polynucleotides and/or vectors thereof described herein (such as the engineered APC and/or antigen polynucleotides of the present invention) can include one or more regulatory elements that can be operatively linked to the polynucleotide. The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of hosT-cell and those that direct expression of the nucleotide sequence only in certain hosT-cells (e.g., tissue-specific regulatory sequences). A tissue-specific promoter can direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the 3-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981).

In some embodiments, the regulatory sequence can be a regulatory sequence described in U.S. Pat. No. 7,776,321, U.S. Pat. Pub. No. 2011/0027239, and PCT publication WO 2011/028929, the contents of which are incorporated by reference herein in their entirety. In some embodiments, the vector can contain a minimal promoter. In some embodiments, the minimal promoter is the Mecp2 promoter, tRNA promoter, or U6. In a further embodiment, the minimal promoter is tissue specific. In some embodiments, the length of the vector polynucleotide the minimal promoters and polynucleotide sequences is less than 4.4 Kb.

To express a polynucleotide, the vector can include one or more transcriptional and/or translational initiation regulatory sequences, e.g. promoters, that direct the transcription of the gene and/or translation of the encoded protein in a cell. In some embodiments a constitutive promoter may be employed. Suitable constitutive promoters for mammalian cells are generally known in the art and include, but are not limited to SV40, CAG, CMV, EF-1α, β-actin, RSV, and PGK. Suitable constitutive promoters for bacterial cells, yeasT-cells, and fungal cells are generally known in the art, such as a T-7 promoter for bacterial expression and an alcohol dehydrogenase promoter for expression in yeast.

In some embodiments, the regulatory element can be a regulated promoter. "Regulated promoter" refers to promoters that direct gene expression not constitutively, but in a temporally- and/or spatially-regulated manner, and includes tissue-specific, tissue-preferred and inducible promoters. Regulated promoters include conditional promoters and inducible promoters. In some embodiments, conditional promoters can be employed to direct expression of a polynucleotide in a specific cell type, under certain environmental conditions, and/or during a specific state of development. Suitable tissue specific promoters can include, but are not limited to, liver specific promoters (e.g. APOA2, SERPIN A1 (hAAT), CYP3A4, and MIR122), pancreatic cell promoters (e.g. INS, IRS2, Pdx1, Alx3, Ppy), cardiac specific promoters (e.g. Myh6 (alpha MHC), MYL2 (MLC-2v), TNI3 (cTn1), NPPA (ANF), Slc8a1 (Ncx1)), central nervous system cell promoters (SYN1, GFAP, INA, NES, MOBP, MBP, TH, FOXA2 (HNF3 beta)), skin cell specific promoters (e.g. FLG, K14, TGM3), immune cell specific promoters, (e.g. ITGAM, CD43 promoter, CD14 promoter, CD45 promoter, CD68 promoter), urogenital cell specific promoters (e.g. Pbsn, Upk2, Sbp, Fer114), endothelial cell specific promoters (e.g. ENG), pluripotent and embryonic germ layer cell specific promoters (e.g. Oct4, NANOG, Synthetic Oct4, T brachyury, NES, SOX17, FOXA2, MIR122), and muscle cell specific promoter (e.g. Desmin). Other tissue and/or cell specific promoters are generally known in the art and are within the scope of this disclosure.

Inducible/conditional promoters can be positively inducible/conditional promoters (e.g. a promoter that activates transcription of the polynucleotide upon appropriate interaction with an activated activator, or an inducer (compound, environmental condition, or other stimulus) or a negative/conditional inducible promoter (e.g. a promoter that is repressed (e.g. bound by a repressor) until the repressor condition of the promotor is removed (e.g. inducer binds a repressor bound to the promoter stimulating release of the promoter by the repressor or removal of a chemical repressor from the promoter environment). The inducer can be a compound, environmental condition, or other stimulus. Thus, inducible/conditional promoters can be responsive to any suitable stimuli such as chemical, biological, or other molecular agents, temperature, light, and/or pH. Suitable inducible/conditional promoters include, but are not limited to, Tet-On, Tet-Off, Lac promoter, pBad, AlcA, LexA, Hsp70 promoter, Hsp90 promoter, pDawn, XVE/OlexA, GVG, and pOp/LhGR.

Where expression in a planT-cell is desired, the components of the e engineered APC and/or antigen described herein are typically placed under control of a plant promoter, i.e. a promoter operable in planT-cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. Different promoters may direct the expression of a gene in different tissues or cell types, or at different stages of development, or in response to different environmental conditions. In particular embodiments, one or more of the engineered APC and/or antigen components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the engineered APC and/or antigen are found in Kawamata et al., (1997) PlanT-cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that can allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome), such as a Light Inducible Transcriptional Effector (LITE) that direct changes in transcriptional activity in a sequence-specific manner. The components of a light inducible system may include one or more elements of the engineered APC and/or antigen described herein, a light-responsive cytochrome heterodimer (e.g. from *Arabidopsis thaliana*), and a transcriptional activation/repression domain. In some embodiments, the vector can include one or more of the inducible DNA binding proteins provided in PCT publication WO 2014/018423 and US Publications, 2015/0291966, 2017/0166903, 2019/0203212, which describe e.g. embodiments of inducible DNA binding proteins and methods of use and can be adapted for use with the present invention.

In some embodiments, transient or inducible expression can be achieved by including, for example, chemical-regulated promotors, i.e. whereby the application of an exogenous chemical induces gene expression. Modulation of gene expression can also be obtained by including a chemical-repressible promoter, where application of the chemical represses gene expression. Chemical-inducible promoters include, but are not limited to, the maize In 2-2 promoter, activated by benzene sulfonamide herbicide safeners (De Veylder et al., (1997) PlanT-cell Physiol 38:568-77), the maize GST promoter (GST-ll-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

In some embodiments, the vector or system thereof can include one or more elements capable of translocating and/or expressing an engineered APC and/or antigen polynucleotide to/in a specific cell component or organelle. Such organelles can include, but are not limited to, nucleus, ribosome, endoplasmic reticulum, golgi apparatus, chloroplast, mitochondria, vacuole, lysosome, cytoskeleton, plasma membrane, cell wall, peroxisome, centrioles, etc.

Selectable Markers and Tags

One or more of the engineered APC and/or antigen polynucleotides can be can be operably linked, fused to, or otherwise modified to include a polynucleotide that encodes or is a selectable marker or tag, which can be a polynucleotide or polypeptide. In some embodiments, the polypeptide encoding a polypeptide selectable marker can be incorporated in the engineered APC and/or antigen polynucleotide such that the selectable marker polypeptide, when translated, is inserted between two amino acids between the N- and C-terminus of the engineered APC and/or antigen polypeptide or at the N- and/or C-terminus of the engineered APC and/or antigen polypeptide. In some embodiments, the selectable marker or tag is a polynucleotide barcode or unique molecular identifier (UMI).

It will be appreciated that the polynucleotide encoding such selectable markers or tags can be incorporated into a polynucleotide encoding one or more components of the engineered APC and/or antigen described herein in an appropriate manner to allow expression of the selectable marker or tag. Such techniques and methods are described elsewhere herein and will be instantly appreciated by one of ordinary skill in the art in view of this disclosure. Many such selectable markers and tags are generally known in the art and are intended to be within the scope of this disclosure.

Suitable selectable markers and tags include, but are not limited to, affinity tags, such as chitin binding protein (CBP), maltose binding protein (MBP), glutathione-S-transferase (GST), poly(His) tag; solubilization tags such as thioredoxin (TRX) and poly(NANP), MBP, and GST; chromatography tags such as those consisting of polyanionic amino acids, such as FLAG-tag; epitope tags such as V5-tag, Myc-tag, HA-tag and NE-tag; protein tags that can allow specific enzymatic modification (such as biotinylation by biotin ligase) or chemical modification (such as reaction with FlAsH-EDT2 for fluorescence imaging), DNA and/or RNA segments that contain restriction enzyme or other enzyme cleavage sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipienT-cell (e.g., tRNA genes, auxotrophic markers); DNA and/or RNA segments that encode products which can be readily identified (e.g., phenotypic markers such as β-galactosidase, GUS; fluorescent proteins such as green fluorescent protein (GFP), cyan (CFP), yellow (YFP), red (RFP), luciferase, and cell surface proteins); polynucleotides that can generate one or more new primer sites for PCR (e.g., the juxtaposition of two DNA sequences not previously juxtaposed), DNA sequences not acted upon or acted upon by a restriction endonuclease or other DNA modifying enzyme, chemical, etc.; epitope tags (e.g. GFP, FLAG- and His-tags), and, DNA sequences that make a molecular barcode or unique molecular identifier (UMI), DNA sequences required for a specific modification (e.g., methylation) that allows its identification. Other suitable markers will be appreciated by those of skill in the art.

Selectable markers and tags can be operably linked to one or more components of the engineered APC and/or antigen described herein via suitable linker, such as a glycine or glycine serine linkers as short as GS or GG up to (GGGGG)$_3$ (SEQ ID NO: 18) or (GGGGS)$_3$ (SEQ ID NO: 19). Other suitable linkers are described elsewhere herein.

The vector or vector system can include one or more polynucleotides encoding one or more targeting moieties. In some embodiments, the targeting moiety encoding polynucleotides can be included in the vector or vector system, such as a viral vector system, such that they are expressed within and/or on the virus particle(s) produced such that the virus particles can be targeted to specific cells, tissues, organs, etc. In some embodiments, the targeting moiety encoding polynucleotides can be included in the vector or vector system such that the engineered APC and/or antigen polynucleotide(s) and/or products expressed therefrom include the targeting moiety and can be targeted to specific cells, tissues, organs, etc. In some embodiments, such as non-viral carriers, the targeting moiety can be attached to the carrier (e.g. polymer, lipid, inorganic molecule etc.) and can be capable of targeting the carrier and any attached or associated engineered APC and/or antigen polynucleotide(s) to specific cells, tissues, organs, etc.

Cell-Free Vector and Polynucleotide Expression

In some embodiments, the polynucleotide encoding one or more features of the engineered APC and/or antigen can be expressed from a vector or suitable polynucleotide in a cell-free in vitro system. In other words, the polynucleotide can be transcribed and optionally translated in vitro. In vitro transcription/translation systems and appropriate vectors are generally known in the art and commercially available. Generally, in vitro transcription and in vitro translation systems replicate the processes of RNA and protein synthesis, respectively, outside of the cellular environment. Vectors and suitable polynucleotides for in vitro transcription can include T7, SP6, T3, promoter regulatory sequences that can be recognized and acted upon by an appropriate polymerase to transcribe the polynucleotide or vector.

In vitro translation can be stand-alone (e.g. translation of a purified polyribonucleotide) or linked/coupled to transcription. In some embodiments, the cell-free (or in vitro) translation system can include extracts from rabbit reticulocytes, wheat germ, and/or E. coli. The extracts can include various macromolecular components that are needed for translation of exogenous RNA (e.g. 70S or 80S ribosomes, tRNAs, aminoacyl-tRNA, synthetases, initiation, elongation factors, termination factors, etc.). Other components can be included or added during the translation reaction, including but not limited to, amino acids, energy sources (ATP, GTP), energy regenerating systems (creatine phosphate and creatine phosphokinase (eukaryotic systems)) (phosphoenol pyruvate and pyruvate kinase for bacterial systems), and other co-factors (Mg2+, K+, etc.). As previously mentioned, in vitro translation can be based on RNA or DNA starting material. Some translation systems can utilize an RNA template as starting material (e.g. reticulocyte lysates and wheat germ extracts). Some translation systems can utilize a DNA template as a starting material (e.g. E coli-based systems). In these systems transcription and translation are coupled and DNA is first transcribed into RNA, which is subsequently translated. Suitable standard and coupled cell-free translation systems are generally known in the art and are commercially available.

Codon Optimization of Vector Polynucleotides

As described elsewhere herein, the polynucleotide encoding one or more embodiments of the engineered APC and/or antigen s described herein can be codon optimized. In some embodiments, one or more polynucleotides contained in a vector ("vector polynucleotides") described herein that are in addition to an optionally codon optimized polynucleotide encoding embodiments of the engineered APC and/or antigen described herein can be codon optimized. In general, codon optimization refers to a process of modifying a nucleic acid sequence for enhanced expression in the hosT-cells of interest by replacing at least one codon (e.g., about or more than about 1, 2, 3, 4, 5, 10, 15, 20, 25, 50, or more codons) of the native sequence with codons that are more frequently or most frequently used in the genes of that hosT-cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis.

Accordingly, genes can be tailored for optimal gene expression in a given organism based on codon optimization. Codon usage tables are readily available, for example, at the "Codon Usage Database" available at www.kazusa.or.jp/codon and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular hosT-cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at http://www.yeastgenome.org/community/codon_usage.shtml, or Codon selection in yeast, Bennetzen and Hall, J Biol Chem. 1982 Mar. 25; 257(6):3026-31. As to codon usage in plants including algae, reference is made to *Codon usage in higher plants, green algae, and cyanobacteria*, Campbell and Gowri, Plant Physiol. 1990 January; 92(1): 1-11.; as well as *Codon usage in plant genes*, Murray et al, Nucleic Acids Res. 1989 Jan. 25; 17(2):477-98; or *Selection on the codon bias of chloroplast and cyanelle genes in different plant and algal lineages*, Morton B R, J Mol Evol. 1998 April; 46(4):449-59.

The vector polynucleotide can be codon optimized for expression in a specific cell-type, tissue type, organ type, and/or subject type. In some embodiments, a codon optimized sequence is a sequence optimized for expression in a eukaryote, e.g., humans (i.e. being optimized for expression in a human or human cell), or for another eukaryote, such as another animal (e.g. a mammal or avian) as is described elsewhere herein. Such codon optimized sequences are within the ambit of the ordinary skilled artisan in view of the description herein. In some embodiments, the polynucleotide is codon optimized for a specific cell type. Such cell types can include, but are not limited to, epithelial cells (including skin cells, cells lining the gastrointestinal tract, cells lining other hollow organs), nerve cells (nerves, brain cells, spinal column cells, nerve supporT-cells (e.g. astrocytes, glial cells, Schwann cells etc.), muscle cells (e.g. cardiac muscle, smooth muscle cells, and skeletal muscle cells), connective tissue cells (fat and other soft tissue padding cells, bone cells, tendon cells, cartilage cells), blood cells, stem cells and other progenitor cells, immune system cells, germ cells, and combinations thereof. Such codon optimized sequences are within the ambit of the ordinary skilled artisan in view of the description herein. In some embodiments, the polynucleotide is codon optimized for a specific tissue type. Such tissue types can include, but are not limited to, muscle tissue, connective tissue, connective tissue, nervous tissue, and epithelial tissue. Such codon optimized sequences are within the ambit of the ordinary skilled artisan in view of the description herein. In some embodiments, the polynucleotide is codon optimized for a specific organ. Such organs include, but are not limited to, muscles, skin, intestines, liver, spleen, brain, lungs, stomach, heart, kidneys, gallbladder, pancreas, bladder, thyroid, bone, blood vessels, blood, and combinations thereof. Such codon optimized sequences are within the ambit of the ordinary skilled artisan in view of the description herein.

In some embodiments, a vector polynucleotide is codon optimized for expression in particular cells, such as prokaryotic or eukaryotic cells. The eukaryotic cells may be those of or derived from a particular organism, such as a plant or a mammal, including but not limited to human, or non-human eukaryote or animal or mammal as discussed herein, e.g., mouse, rat, rabbit, dog, livestock, or non-human mammal or primate.

Non-Viral Vectors and Carriers

In some embodiments, the vector is a non-viral vector or carrier. In some embodiments, non-viral vectors can have the advantage(s) of reduced toxicity and/or immunogenicity and/or increased bio-safety as compared to viral vectors The terms of art "Non-viral vectors and carriers" and as used herein in this context refers to molecules and/or compositions that are not based on one or more component of a virus or virus genome (excluding any nucleotide to be delivered and/or expressed by the non-viral vector) that can be capable of attaching to, incorporating, coupling, and/or otherwise interacting with an engineered APC and/or antigen polynucleotide of the present invention and can be capable of ferrying the polynucleotide to a cell and/or expressing the polynucleotide. It will be appreciated that this does not exclude the inclusion of a virus-based polynucleotide that is to be delivered. For example, if a gRNA to be delivered is directed against a virus component and it is inserted or otherwise coupled to an otherwise non-viral vector or carrier, this would not make said vector a "viral vector". Non-viral vectors and carriers include naked polynucleotides, chemical-based carriers, polynucleotide (non-viral) based vectors, and particle-based carriers. It will be appreciated that the term "vector" as used in the context of non-viral vectors and carriers refers to polynucleotide vectors and "carriers" used in this context refers to a non-nucleic acid or polynucleotide molecule or composition that be attached to or otherwise interact with a polynucleotide to be delivered, such as an engineered APC and/or antigen polynucleotide of the present invention.

Naked Polynucleotides

In some embodiments one or more engineered APC and/or antigen polynucleotides described elsewhere herein can be included in a naked polynucleotide. The term of art "naked polynucleotide" as used herein refers to polynucleotides that are not associated with another molecule (e.g. proteins, lipids, and/or other molecules) that can often help protect it from environmental factors and/or degradation. As used herein, associated with includes, but is not limited to, linked to, adhered to, adsorbed to, enclosed in, enclosed in or within, mixed with, and the like. Naked polynucleotides that include one or more of the engineered APC and/or antigen polynucleotides described herein can be delivered directly to a hosT-cell and optionally expressed therein. The naked polynucleotides can have any suitable two- and three-dimensional configurations. By way of non-limiting examples, naked polynucleotides can be single-stranded molecules, double stranded molecules, circular molecules (e.g. plasmids and artificial chromosomes), molecules that contain portions that are single stranded and portions that are double stranded (e.g. ribozymes), and the like. In some embodiments, the naked polynucleotide contains only the engineered APC and/or antigen polynucleotide(s) of the present invention. In some embodiments, the naked polynucleotide can contain other nucleic acids and/or polynucleotides in addition to the engineered APC and/or antigen polynucleotide(s) of the present invention. The naked polynucleotides can include one or more elements of a transposon system. Transposons and system thereof are described in greater detail elsewhere herein.

Non-Viral Polynucleotide Vectors

In some embodiments, one or more of the engineered APC and/or antigen polynucleotides can be included in a non-viral polynucleotide vector. Suitable non-viral polynucleotide vectors include, but are not limited to, transposon vectors and vector systems, plasmids, bacterial artificial chromosomes, yeast artificial chromosomes, AR (antibiotic resistance)-free plasmids and miniplasmids, circular covalently closed vectors (e.g. minicircles, minivectors, miniknots,), linear covalently closed vectors ("dumbbell shaped"), MIDGE (minimalistic immunologically defined gene expression) vectors, MiLV (micro-linear vector) vectors, Ministrings, mini-intronic plasmids, PSK systems (post-segregationally killing systems), ORT (operator repressor titration) plasmids, and the like. See e.g. Hardee et al. 2017. Genes. 8(2):65.

In some embodiments, the non-viral polynucleotide vector can have a conditional origin of replication. In some embodiments, the non-viral polynucleotide vector can be an ORT plasmid. In some embodiments, the non-viral polynucleotide vector can have a minimalistic immunologically defined gene expression. In some embodiments, the non-viral polynucleotide vector can have one or more post-segregationally killing system genes. In some embodiments, the non-viral polynucleotide vector is AR-free. In some embodiments, the non-viral polynucleotide vector is a mini-vector. In some embodiments, the non-viral polynucleotide vector includes a nuclear localization signal. In some embodiments, the non-viral polynucleotide vector can include one or more CpG motifs. In some embodiments, the non-viral polynucleotide vectors can include one or more scaffold/matrix attachment regions (S/MARs). See e.g. Mirkovitch et al. 1984. Cell. 39:223-232, Wong et al. 2015. Adv. Genet. 89:113-152, whose techniques and vectors can be adapted for use in the present invention. S/MARs are AT-rich sequences that play a role in the spatial organization of chromosomes through DNA loop base attachment to the nuclear matrix. S/MARs are often found close to regulatory elements such as promoters, enhancers, and origins of DNA replication. Inclusion of one or S/MARs can facilitate a once-per-cell-cycle replication to maintain the non-viral polynucleotide vector as an episome in daughter cells. In embodiments, the S/MAR sequence is located downstream of an actively transcribed polynucleotide (e.g. one or more engineered APC and/or antigen of the present invention) included in the non-viral polynucleotide vector. In some embodiments, the S/MAR can be a S/MAR from the beta-interferon gene cluster. See e.g. Verghese et al. 2014. Nucleic Acid Res. 42:e53; Xu et al. 2016. Sci. China Life Sci. 59:1024-1033; Jin et al. 2016. 8:702-711; Koirala et al. 2014. Adv. Exp. Med. Biol. 801:703-709; and Nehlsen et al. 2006. Gene Ther. Mol. Biol. 10:233-244, whose techniques and vectors can be adapted for use in the present invention.

In some embodiments, the non-viral vector is a transposon vector or system thereof. As used herein, "transposon" (also referred to as transposable element) refers to a polynucleotide sequence that is capable of moving form location in a genome to another. There are several classes of transposons. Transposons include retrotransposons and DNA transposons. Retrotransposons require the transcription of the polynucleotide that is moved (or transposed) in order to transpose the polynucleotide to a new genome or polynucleotide. DNA transposons are those that do not require reverse transcription of the polynucleotide that is moved (or transposed) in order to transpose the polynucleotide to a new genome or polynucleotide. In some embodiments, the non-viral polynucleotide vector can be a retrotransposon vector. In some embodiments, the retrotransposon vector includes long terminal repeats. In some embodiments, the retrotransposon vector does not include long terminal repeats. In some embodiments, the non-viral polynucleotide vector can be a DNA transposon vector. DNA transposon vectors can include a polynucleotide sequence encoding a transposase. In some embodiments, the transposon vector is configured as a non-autonomous transposon vector, meaning that the transposition does not occur spontaneously on its own. In some of these embodiments, the transposon vector lacks one or more polynucleotide sequences encoding proteins required for transposition. In some embodiments, the non-autonomous transposon vectors lack one or more Ac elements.

In some embodiments a non-viral polynucleotide transposon vector system can include a first polynucleotide vector that contains the engineered APC and/or antigen polynucleotide(s) of the present invention flanked on the 5' and 3' ends by transposon terminal inverted repeats (TIRs) and a second polynucleotide vector that includes a polynucleotide capable of encoding a transposase coupled to a promoter to drive expression of the transposase. When both are expressed in the same cell the transposase can be expressed from the second vector and can transpose the material between the TIRs on the first vector (e.g. the engineered APC and/or antigen polynucleotide(s) of the present invention) and integrate it into one or more positions in the hosT-cell's genome. In some embodiments the transposon vector or system thereof can be configured as a gene trap. In some embodiments, the TIRs can be configured to flank a strong splice acceptor site followed by a reporter and/or other gene (e.g. one or more of the engineered APC and/or antigen polynucleotide(s) of the present invention) and a strong poly A tail. When transposition occurs while using this vector or system thereof, the transposon can insert into an intron of a gene and the inserted reporter or other gene can provoke a mis-splicing process and as a result it in activates the trapped gene.

Any suitable transposon system can be used. Suitable transposon and systems thereof can include, Sleeping Beauty transposon system (Tc1/mariner superfamily) (see e.g. Ivics et al. 1997. Cell. 91(4): 501-510), piggyBac (piggyBac superfamily) (see e.g. Li et al. 2013 110(25): E2279-E2287 and Yusa et al. 2011. PNAS. 108(4): 1531-1536), Tol2 (superfamily hAT), Frog Prince (Tc1/mariner superfamily) (see e.g. Miskey et al. 2003 Nucleic Acid Res. 31(23):6873-6881) and variants thereof.

Chemical Carriers

In some embodiments the engineered APC and/or antigen polynucleotide(s) can be coupled to a chemical carrier. Chemical carriers that can be suitable for delivery of polynucleotides can be broadly classified into the following classes: (i) inorganic particles, (ii) lipid-based, (iii) polymer-based, and (iv) peptide based. They can be categorized as (1) those that can form condensed complexes with a polynucleotide (such as the engineered APC and/or antigen polynucleotide(s) of the present invention), (2) those capable of targeting specific cells, (3) those capable of increasing delivery of the polynucleotide (such as the engineered APC and/or antigen polynucleotide(s) of the present invention) to the nucleus or cytosol of a hosT-cell, (4) those capable of disintegrating from DNA/RNA in the cytosol of a hosT-cell, and (5) those capable of sustained or controlled release. It will be appreciated that any one given chemical carrier can include features from multiple categories. The term "particle" as used herein, refers to any suitable sized particles for delivery of the engineered APC and/or antigen components described herein. Suitable sizes include macro-, micro-, and nano-sized particles.

In some embodiments, the non-viral carrier can be an inorganic particle. In some embodiments, the inorganic particle, can be a nanoparticle. The inorganic particles can be configured and optimized by varying size, shape, and/or porosity. In some embodiments, the inorganic particles are optimized to escape from the reticulo endothelial system. In some embodiments, the inorganic particles can be optimized to protect an entrapped molecule from degradation, the Suitable inorganic particles that can be used as non-viral carriers in this context can include, but are not limited to, calcium phosphate, silica, metals (e.g. gold, platinum, silver, palladium, rhodium, osmium, iridium, ruthenium, mercury, copper, rhenium, titanium, niobium, tantalum, and combinations thereof), magnetic compounds, particles, and materials, (e.g. supermagnetic iron oxide and magnetite), quantum dots, fullerenes (e.g. carbon nanoparticles, nanotubes, nanostrings, and the like), and combinations thereof. Other suitable inorganic non-viral carriers are discussed elsewhere herein.

In some embodiments, the non-viral carrier can be lipid-based. Suitable lipid-based carriers are also described in greater detail herein. In some embodiments, the lipid-based carrier includes a cationic lipid or an amphiphilic lipid that is capable of binding or otherwise interacting with a negative charge on the polynucleotide to be delivered (e.g. such as an e engineered APC and/or antigen polynucleotide of the present invention). In some embodiments, chemical non-viral carrier systems can include a polynucleotide such as the engineered APC and/or antigen polynucleotide(s) of the present invention) and a lipid (such as a cationic lipid). These are also referred to in the art as lipoplexes. Other embodiments of lipoplexes are described elsewhere herein. In some embodiments, the non-viral lipid-based carrier can be a lipid nano emulsion. Lipid nano emulsions can be formed by the dispersion of an immiscible liquid in another stabilized emulsifying agent and can have particles of about 200 nm that are composed of the lipid, water, and surfactant that can contain the polynucleotide to be delivered (e.g. the engineered APC and/or antigen polynucleotide(s) of the present invention). In some embodiments, the lipid-based non-viral carrier can be a solid lipid particle or nanoparticle.

In some embodiments, the non-viral carrier can be peptide-based. In some embodiments, the peptide-based non-viral carrier can include one or more cationic amino acids. In some embodiments, 35 to 40, 45, 50, 55, 60, 65, 70, 75, 80, 85, 90, 95, 99 or 100% of the amino acids are cationic. In some embodiments, peptide carriers can be used in conjunction with other types of carriers (e.g. polymer-based carriers and lipid-based carriers to functionalize these carriers). In some embodiments, the functionalization is targeting a hosT-cell. Suitable polymers that can be included in the polymer-based non-viral carrier can include, but are not limited to, polyethylenimine (PEI), chitosan, poly (DL-lactide) (PLA), poly (DL-Lactide-co-glycoside) (PLGA), dendrimers (see e.g. US Pat. Pub. 2017/0079916 whose techniques and compositions can be adapted for use with the engineered APC and/or antigen polynucleotides of the present invention), polymethacrylate, and combinations thereof.

In some embodiments, the non-viral carrier can be configured to release an engineered delivery system polynucleotide that is associated with or attached to the non-viral carrier in response to an external stimulus, such as pH, temperature, osmolarity, concentration of a specific molecule or composition (e.g. calcium, NaCl, and the like), pressure and the like. In some embodiments, the non-viral carrier can be a particle that is configured includes one or more of the engineered APC and/or antigen polynucleotides describe herein and a environmental triggering agent response element, and optionally a triggering agent. In some embodiments, the particle can include a polymer that can be selected from the group of polymethacrylates and polyacrylates. In some embodiments, the non-viral particle can include one or more embodiments of the compositions microparticles described in US Pat. Pubs. 20150232883 and 20050123596, whose techniques and compositions can be adapted for use in the present invention.

In some embodiments, the non-viral carrier can be a polymer-based carrier. In some embodiments, the polymer is cationic or is predominantly cationic such that it can interact in a charge-dependent manner with the negatively charged polynucleotide to be delivered (such as the engineered APC and/or antigen polynucleotide(s) of the present invention). Polymer-based systems are described in greater detail elsewhere herein.

Viral Vectors

In some embodiments, the vector is a viral vector. The term of art "viral vector" and as used herein in this context refers to polynucleotide based vectors that contain one or more elements from or based upon one or more elements of a virus that can be capable of expressing and packaging a polynucleotide, such as an engineered APC and/or antigen polynucleotide of the present invention, into a virus particle and producing said virus particle when used alone or with one or more other viral vectors (such as in a viral vector system). Viral vectors and systems thereof can be used for producing viral particles for delivery of and/or expression of one or more components of the engineered APC and/or antigen described herein. The viral vector can be part of a viral vector system involving multiple vectors. In some embodiments, systems incorporating multiple viral vectors can increase the safety of these systems. Suitable viral vectors can include retroviral-based vectors, lentiviral-based vectors, adenoviral-based vectors, adeno associated vectors, helper-dependent adenoviral (HdAd) vectors, hybrid adenoviral vectors, herpes simplex virus-based vectors, poxvirus-based vectors, and Epstein-Barr virus-based vectors. Other embodiments of viral vectors and viral particles produce therefrom are described elsewhere herein. In some embodiments, the viral vectors are configured to produce replication incompetent viral particles for improved safety of these systems.

Retroviral and Lentiviral Vectors

Retroviral vectors can be composed of cis-acting long terminal repeats with packaging capacity for up to 6-10 kb of foreign sequence. The minimum cis-acting LTRs are sufficient for replication and packaging of the vectors, which are then used to integrate the therapeutic gene into the targeT-cell to provide permanent transgene expression. Suitable retroviral vectors for the engineered APC and/or antigen can include those based upon murine leukemia virus (MuLV), gibbon ape leukemia virus (GaLV), Simian immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700), vectors and systems thereof based on baboon endogenous retrovirus or include one or more polynucleotides capable of expression one or more baboon endogenous retrovirus envelope or other protein such that the resulting viral particle has a baboon endogenous retrovirus pseudotype (see e.g. Girard et al., 2012 RNA VIRAL VECTORS1 VOLUME 20, SUPPLEMENT 1, S1, May 1, 2012; Girard-Gagnepain et al.

2014. Blood. 124: 1221-1231; Levy et al. 2016. J. Thrombosis and Haemostasis, 14:2478-2492; Hum Gene Ther. 2019 May; 30(5):601-617. doi: 10.1089/hum.2018.022. Epub 2019 Mar. 15). In some embodiments, the retroviral vector or vector system can be based on baboon endogenous retrovirus or include one or more polynucleotides capable of expression one or more Baboon endogenous retrovirus envelope or other protein such that the resulting viral particle has a baboon endogenous retrovirus pseudotype. In some embodiments, the retroviral vector can be a BaEVRless vector as described in Hum Gene Ther. 2019 May; 30(5): 601-617. doi: 10.1089/hum.2018.022. Epub 2019 Mar. 15) e.g. or a modified version thereof that is adapted for use with the invention described and provided herein. Selection of a retroviral gene transfer system may therefore depend on the target tissue.

The tropism of a retrovirus can be altered by incorporating foreign envelope proteins, expanding the potential target population of targeT-cells. Lentiviral vectors are retroviral vectors that are able to transduce or infect non-dividing cells and are described in greater detail elsewhere herein. A retrovirus can also be engineered to allow for conditional expression of the inserted transgene, such that only certain cell types are infected by the lentivirus.

Lentiviruses are complex retroviruses that have the ability to infect and express their genes in both mitotic and post-mitotic cells. Advantages of using a lentiviral approach can include the ability to transduce or infect non-dividing cells and their ability to typically produce high viral titers, which can increase efficiency or efficacy of production and delivery. Suitable lentiviral vectors include, but are not limited to, human immunodeficiency virus (HIV)-based lentiviral vectors, feline immunodeficiency virus (FIV)-based lentiviral vectors, simian immunodeficiency virus (SIV)-based lentiviral vectors, Moloney Murine Leukaemia Virus (Mo-MLV), Visna.maedi virus (VMV)-based lentiviral vector, caprine arthritis-encephalitis virus (CAEV)-based lentiviral vector, bovine immune deficiency virus (BIV)-based lentiviral vector, and Equine infectious anemia (EIAV)-based lentiviral vector. In some embodiments, an HIV-based lentiviral vector system can be used. In some embodiments, a FIV-based lentiviral vector system can be used.

In some embodiments, the lentiviral vector is an EIAV-based lentiviral vector or vector system. EIAV vectors have been used to mediate expression, packaging, and/or delivery in other contexts, such as for ocular gene therapy (see, e.g., Balagaan, J Gene Med 2006; 8: 275-285). In another embodiment, RetinoStat®, (see, e.g., Binley et al., HUMAN GENE THERAPY 23:980-991 (September 2012)), which describes RetinoStat®, an equine infectious anemia virus-based lentiviral gene therapy vector that expresses angio-static proteins endostatin and angiostatin that is delivered via a subretinal injection for the treatment of the wet form of age-related macular degeneration. Any of these vectors described in these publications can be modified for the elements of the engineered APC and/or antigen described herein.

In some embodiments, the lentiviral vector or vector system thereof can be a first-generation lentiviral vector or vector system thereof. First-generation lentiviral vectors can contain a large portion of the lentivirus genome, including the gag and pol genes, other additional viral proteins (e.g. VSV-G) and other accessory genes (e.g. vif, vprm vpu, nef, and combinations thereof), regulatory genes (e.g. tat and/or rev) as well as the gene of interest between the LTRs. First generation lentiviral vectors can result in the production of virus particles that can be capable of replication in vivo, which may not be appropriate for some instances or applications.

In some embodiments, the lentiviral vector or vector system thereof can be a second-generation lentiviral vector or vector system thereof. Second-generation lentiviral vectors do not contain one or more accessory virulence factors and do not contain all components necessary for virus particle production on the same lentiviral vector. This can result in the production of a replication-incompetent virus particle and thus increase the safety of these systems over first-generation lentiviral vectors. In some embodiments, the second-generation vector lacks one or more accessory virulence factors (e.g. vif, vprm, vpu, nef, and combinations thereof). Unlike the first-generation lentiviral vectors, no single second generation lentiviral vector includes all features necessary to express and package a polynucleotide into a virus particle. In some embodiments, the envelope and packaging components are split between two different vectors with the gag, pol, rev, and tat genes being contained on one vector and the envelope protein (e.g. VSV-G) are contained on a second vector. The gene of interest, its promoter, and LTRs can be included on a third vector that can be used in conjunction with the other two vectors (packaging and envelope vectors) to generate a replication-incompetent virus particle.

In some embodiments, the lentiviral vector or vector system thereof can be a third-generation lentiviral vector or vector system thereof. Third-generation lentiviral vectors and vector systems thereof have increased safety over first- and second-generation lentiviral vectors and systems thereof because, for example, the various components of the viral genome are split between two or more different vectors but used together in vitro to make virus particles, they can lack the tat gene (when a constitutively active promoter is included up-stream of the LTRs), and they can include one or more deletions in the 3'LTR to create self-inactivating (SIN) vectors having disrupted promoter/enhancer activity of the LTR. In some embodiments, a third-generation lentiviral vector system can include (i) a vector plasmid that contains the polynucleotide of interest and upstream promoter that are flanked by the 5' and 3' LTRs, which can optionally include one or more deletions present in one or both of the LTRs to render the vector self-inactivating; (ii) a "packaging vector(s)" that can contain one or more genes involved in packaging a polynucleotide into a virus particle that is produced by the system (e.g. gag, pol, and rev) and upstream regulatory sequences (e.g. promoter(s)) to drive expression of the features present on the packaging vector, and (iii) an "envelope vector" that contains one or more envelope protein genes and upstream promoters. In embodiments, the third-generation lentiviral vector system can include at least two packaging vectors, with the gag-pol being present on a different vector than the rev gene.

In some embodiments, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) can be used/and/or adapted to the engineered APC and/or antigen of the present invention.

In some embodiments, the pseudotype and infectivity or tropism of a lentivirus particle can be tuned by altering the type of envelope protein(s) included in the lentiviral vector or system thereof. As used herein, an "envelope protein" or "outer protein" means a protein exposed at the surface of a viral particle that is not a capsid protein. For example, envelope or outer proteins typically comprise proteins embedded in the envelope of the virus. In some embodiments, a lentiviral vector or vector system thereof can include a VSV-G envelope protein. VSV-G mediates viral attachment to an LDL receptor (LDLR) or an LDLR family member present on a hosT-cell, which triggers endocytosis of the viral particle by the hosT-cell. Because LDLR is expressed by a wide variety of cells, viral particles expressing the VSV-G envelope protein can infect or transduce a wide variety of cell types. Other suitable envelope proteins can be incorporated based on the hosT-cell that a user desires to be infected by a virus particle produced from a lentiviral vector or system thereof described herein and can include, but are not limited to, feline endogenous virus envelope protein (RD114) (see e.g. Hanawa et al. Molec. Ther. 2002 5(3) 242-251), modified Sindbis virus envelope proteins (see e.g. Morizono et al. 2010. J. Virol. 84(14) 6923-6934; Morizono et al. 2001. J. Virol. 75:8016-8020; Morizono et al. 2009. J. Gene Med. 11:549-558; Morizono et al. 2006 Virology 355:71-81; Morizono et al J. Gene Med. 11:655-663, Morizono et al. 2005 Nat. Med. 11:346-352), baboon retroviral envelope protein (see e.g. Girard-Gagnepain et al. 2014. Blood. 124: 1221-1231 Girard et al., 2012 RNA VIRAL VECTORS1 VOLUME 20, SUPPLEMENT 1, S1, May 1, 2012; Levy et al. 2016. J. Thrombosis and Haemostasis, 14:2478-2492; Hum Gene Ther. 2019 May; 30(5): 601-617. doi: 10.1089/hum.2018.022. Epub 2019 Mar. 15)); Tupaia paramyxovirus glycoproteins (see e.g. Enkirch T. et al., 2013. Gene Ther. 20:16-23); measles virus glycoproteins (see e.g. Funke et al. 2008. Molec. Ther. 16(8): 1427-1436), rabies virus envelope proteins, MLV envelope proteins, Ebola envelope proteins, baculovirus envelope proteins, filovirus envelope proteins, hepatitis E1 and E2 envelope proteins, gp41 and gp120 of HIV, hemagglutinin, neuraminidase, M2 proteins of influenza virus, and combinations thereof. In some embodiments, the lentiviral particle can be pseudotyped based upon baboon endogenous retrovirus. In some of these embodiments, the viral particle can include and/or express a baboon endogenous retrovirus envelope protein.

In some embodiments, the tropism of the resulting lentiviral particle can be tuned by incorporating cell targeting peptides into a lentiviral vector such that the cell targeting peptides are expressed on the surface of the resulting lentiviral particle. In some embodiments, a lentiviral vector can contain an envelope protein that is fused to a cell targeting protein (see e.g. Buchholz et al. 2015. Trends Biotechnol. 33:777-790; Bender et al. 2016. PLoS Pathog. 12(e1005461); and Friedrich et al. 2013. Mol. Ther. 2013. 21: 849-859.

In some embodiments, a split-intein-mediated approach to target lentiviral particles to a specific cell type can be used (see e.g. Chamoun-Emanuelli et al. 2015. Biotechnol. Bioeng. 112:2611-2617, Ramirez et al. 2013. Protein. Eng. Des. Sel. 26:215-233. In these embodiments, a lentiviral vector can contain one half of a splicing-deficient variant of the naturally split intein from *Nostoc punctiforme* fused to a cell targeting peptide and the same or different lentiviral vector can contain the other half of the split intein fused to an envelope protein, such as a binding-deficient, fusion-competent virus envelope protein. This can result in production of a virus particle from the lentiviral vector or vector system that includes a split intein that can function as a molecular Velcro linker to link the cell-binding protein to the pseudotyped lentivirus particle. This approach can be advantageous for use where surface-incompatibilities can restrict the use of, e.g., cell targeting peptides.

In some embodiments, a covalent-bond-forming protein-peptide pair can be incorporated into one or more of the lentiviral vectors described herein to conjugate a cell targeting peptide to the virus particle (see e.g. Kasaraneni et al. 2018. Sci. Reports (8) No. 10990). In some embodiments, a lentiviral vector can include an N-termial PDZ domain of InaD protein (PDZ1) and its pentapeptide ligand (TEFCA) from NorpA, which can conjugate the cell targeting peptide to the virus particle via a covalent bond (e.g. a disulfide bond). In some embodiments, the PDZ1 protein can be fused to an envelope protein, which can optionally be binding deficient and/or fusion competent virus envelope protein and included in a lentiviral vector. In some embodiments, the TEFCA can be fused to a cell targeting peptide and the TEFCA-CPT fusion construct can be incorporated into the same or a different lentiviral vector as the PDZ1-envelope protein construct. During virus production, specific interaction between the PDZ1 and TEFCA facilitates producing virus particles covalently functionalized with the cell targeting peptide and thus capable of targeting a specific cell-type based upon a specific interaction between the cell targeting peptide and cells expressing its binding partner. This approach can be advantageous for use where surface-incompatibilities can restrict the use of, e.g., cell targeting peptides.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015. Any of these systems or a variant thereof can be used to deliver an engineered APC and/or antigen polynucleotide described herein to a cell.

In some embodiments, a lentiviral vector system can include one or more transfer plasmids. Transfer plasmids can be generated from various other vector backbones and can include one or more features that can work with other retroviral and/or lentiviral vectors in the system that can, for example, improve safety of the vector and/or vector system, increase virial titers, and/or increase or otherwise enhance expression of the desired insert to be expressed and/or packaged into the viral particle. Suitable features that can be included in a transfer plasmid can include, but are not limited to, 5'LTR, 3'LTR, SIN/LTR, origin of replication (Ori), selectable marker genes (e.g. antibiotic resistance genes), Psi (Ψ), RRE (rev response element), cPPT (central polypurine tract), promoters, WPRE (woodchuck hepatitis post-transcriptional regulatory element), SV40 polyadenylation signal, pUC origin, SV40 origin, F1 origin, and combinations thereof.

Adenoviral Vectors, Helper-Dependent Adenoviral Vectors, and Hybrid Adenoviral Vectors In some embodiments, the vector can be an adenoviral vector. In some embodiments, the adenoviral vector can include elements such that the virus particle produced using the vector or system thereof can be serotype 2 or serotype 5. In some embodiments, the polynucleotide to be delivered via the adenoviral particle can be up to about 8 kb. Thus, in some embodiments, an adenoviral vector can include a DNA polynucleotide to be delivered that can range in size from about 0.001 kb to about 8 kb. Adenoviral vectors have been used successfully in several contexts (see e.g. Teramato et al. 2000. Lancet. 355:1911-1912; Lai et al. 2002. DNA Cell. Biol. 21:895-913; Flotte et al., 1996. Hum. Gene. Ther. 7:1145-1159; and Kay et al. 2000. Nat. Genet. 24:257-261.

In some embodiments the vector can be a helper-dependent adenoviral vector or system thereof. These are also referred to in the art as "gutless" or "gutted" vectors and are a modified generation of adenoviral vectors (see e.g. Thrasher et al. 2006. Nature. 443:E5-7). In embodiments of the helper-dependent adenoviral vector system one vector (the helper) can contain all the viral genes required for replication but contains a conditional gene defect in the packaging domain. The second vector of the system can contain only the ends of the viral genome, one or more engineered APC and/or antigen polynucleotides, and the native packaging recognition signal, which can allow selective packaged release from the cells (see e.g. Cideciyan et al. 2009. N Engl J Med. 361:725-727). Helper-dependent adenoviral vector systems have been successful for gene delivery in several contexts (see e.g. Simonelli et al. 2010. J Am Soc Gene Ther. 18:643-650; Cideciyan et al. 2009. N Engl J Med. 361:725-727; Crane et al. 2012. Gene Ther. 19(4):443-452; Alba et al. 2005. Gene Ther. 12:18-S27; Croyle et al. 2005. Gene Ther. 12:579-587; Amalfitano et al. 1998. J. Virol. 72:926-933; and Morral et al. 1999. PNAS. 96:12816-12821). The techniques and vectors described in these publications can be adapted for inclusion and delivery of the engineered APC and/or antigen polynucleotides described herein. In some embodiments, the polynucleotide to be delivered via the viral particle produced from a helper-dependent adenoviral vector or system thereof can be up to about 37 kb. Thus, in some embodiments, a adenoviral vector can include a DNA polynucleotide to be delivered that can range in size from about 0.001 kb to about 37 kb (see e.g. Rosewell et al. 2011. J. Genet. Syndr. Gene Ther. Suppl. 5:001).

In some embodiments, the vector is a hybrid-adenoviral vector or system thereof. Hybrid adenoviral vectors are composed of the high transduction efficiency of a gene-deleted adenoviral vector and the long-term genome-integrating potential of adeno-associated, retroviruses, lentivirus, and transposon based-gene transfer. In some embodiments, such hybrid vector systems can result in stable transduction and limited integration site. See e.g. Balague et al. 2000. Blood. 95:820-828; Morral et al. 1998. Hum. Gene Ther. 9:2709-2716; Kubo and Mitani. 2003. J. Virol. 77(5): 2964-2971; Zhang et al. 2013. PloS One. 8(10) e76771; and Cooney et al. 2015. Mol. Ther. 23(4):667-674), whose techniques and vectors described therein can be modified and adapted for use in the engineered APC and/or antigen of the present invention. In some embodiments, a hybrid-adenoviral vector can include one or more features of a retrovirus and/or an adeno-associated virus. In some embodiments the hybrid-adenoviral vector can include one or more features of a spuma retrovirus or foamy virus (FV). See e.g. Ehrhardt et al. 2007. Mol. Ther. 15:146-156 and Liu et al. 2007. Mol. Ther. 15:1834-1841, whose techniques and vectors described therein can be modified and adapted for use in the engineered APC and/or antigen of the present invention. Advantages of using one or more features from the FVs in the hybrid-adenoviral vector or system thereof can include the ability of the viral particles produced therefrom to infect a broad range of cells, a large packaging capacity as compared to other retroviruses, and the ability to persist in quiescent (non-dividing) cells. See also e.g. Ehrhardt et al. 2007. Mol. Ther. 156:146-156 and Shuji et al. 2011. Mol. Ther. 19:76-82, whose techniques and vectors described therein can be modified and adapted for use in the engineered APC and/or antigen of the present invention.

Adeno Associated Viral (AAV) Vectors

In an embodiment, the vector can be an adeno-associated virus (AAV) vector. See, e.g., West et al., Virology 160:38-47 (1987); U.S. Pat. No. 4,797,368; WO 93/24641; Kotin, Human Gene Therapy 5:793-801 (1994); and Muzyczka, J. Clin. Invest. 94:1351 (1994). Although similar to adenoviral vectors in some of their features, AAVs have some deficiency in their replication and/or pathogenicity and thus can be safer that adenoviral vectors. In some embodiments the AAV can integrate into a specific site on chromosome 19 of a human cell with no observable side effects. In some embodiments, the capacity of the AAV vector, system thereof, and/or AAV particles can be up to about 4.7 kb.

The AAV vector or system thereof can include one or more regulatory molecules. In some embodiments the regulatory molecules can be promoters, enhancers, repressors and the like, which are described in greater detail elsewhere herein. In some embodiments, the AAV vector or system thereof can include one or more polynucleotides that can encode one or more regulatory proteins. In some embodiments, the one or more regulatory proteins can be selected from Rep78, Rep68, Rep52, Rep40, variants thereof, and combinations thereof.

The AAV vector or system thereof can include one or more polynucleotides that can encode one or more capsid proteins. The capsid proteins can be selected from VP1, VP2, VP3, and combinations thereof. The capsid proteins can be capable of assembling into a protein shell of the AAV virus particle. In some embodiments, the AAV capsid can contain 60 capsid proteins. In some embodiments, the ratio of VP1:VP2:VP3 in a capsid can be about 1:1:10.

In some embodiments, the AAV vector or system thereof can include one or more adenovirus helper factors or polynucleotides that can encode one or more adenovirus helper factors. Such adenovirus helper factors can include, but are not limited, E1A, E1B, E2A, E4ORF6, and VA RNAs. In some embodiments, a producing hosT-cell line expresses one or more of the adenovirus helper factors.

The AAV vector or system thereof can be configured to produce AAV particles having a specific serotype. In some embodiments, the serotype can be AAV-1, AAV-2, AAV-3, AAV-4, AAV-5, AAV-6, AAV-8, AAV-9 or any combinations thereof. In some embodiments, the AAV can be AAV1, AAV-2, AAV-5 or any combination thereof. One can select the AAV of the AAV with regard to the cells to be targeted; e.g., one can select AAV serotypes 1, 2, 5 or a hybrid capsid AAV-1, AAV-2, AAV-5 or any combination thereof for targeting brain and/or neuronal cells; and one can select AAV-4 for targeting cardiac tissue; and one can select AAV8 for delivery to the liver. Thus, in some embodiments, an AAV vector or system thereof capable of producing AAV particles capable of targeting the brain and/or neuronal cells can be configured to generate AAV particles having serotypes 1, 2, 5 or a hybrid capsid AAV-1, AAV-2, AAV-5 or any combination thereof. In some embodiments, an AAV vector or system thereof capable of producing AAV particles capable of targeting cardiac tissue can be configured to generate an AAV particle having an AAV-4 serotype. In some embodiments, an AAV vector or system thereof capable of producing AAV particles capable of targeting the liver can be configured to generate an AAV having an AAV-8 serotype. In some embodiments, the AAV vector is a hybrid AAV vector or system thereof. Hybrid AAVs are AAVs that include genomes with elements from one serotype that are packaged into a capsid derived from at least one different serotype. For example, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the 2nd plasmid, the pRepCap will be different. In this plasmid, called pRep2/Cap5, the Rep gene is still derived from AAV2, while the Cap gene is derived from AAV5. The production scheme is the same as the above-mentioned approach for AAV2 production. The resulting rAAV is called rAAV2/5, in which the genome is based on recombinant AAV2, while the capsid is based on AAV5. It is assumed the cell or tissue-tropism displayed by this AAV2/5 hybrid virus should be the same as that of AAV5.

A tabulation of certain AAV serotypes as to these cells can be found in Grimm, D. et al, J. Virol. 82: 5887-5911 (2008) (Table 2):

TABLE 2

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

In some embodiments, the AAV vector or system thereof is configured as a "gutless" vector, similar to that described in connection with a retroviral vector. In some embodiments, the "gutless" AAV vector or system thereof can have the cis-acting viral DNA elements involved in genome amplification and packaging in linkage with the heterologous sequences of interest (e.g. the engineered APC and/or antigen polynucleotide(s)).

Herpes Simplex Viral Vectors

In some embodiments, the vector can be a Herpes Simplex Viral (HSV)-based vector or system thereof. HSV systems can include the disabled infections single copy (DISC) viruses, which are composed of a glycoprotein H defective mutant HSV genome. When the defective HSV is propagated in complementing cells, virus particles can be generated that are capable of infecting subsequent T-cells permanently replicating their own genome but are not capable of producing more infectious particles. See e.g. 2009. Trobridge. Exp. Opin. Biol. Ther. 9:1427-1436, whose techniques and vectors described therein can be modified and adapted for use in the engineered APC and/or antigen of the present invention. In some embodiments where an HSV vector or system thereof is utilized, the host T-cell can be a complementing cell. In some embodiments, HSV vector or system thereof can be capable of producing virus particles capable of delivering a polynucleotide cargo of up to 150 kb. Thus, in some embodiment the engineered APC and/or antigen polynucleotide(s) included in the HSV-based viral vector or system thereof can sum from about 0.001 to about 150 kb. HSV-based vectors and systems thereof have been successfully used in several contexts including various models of neurologic disorders. See e.g. Cockrell et al. 2007. Mol. Biotechnol. 36:184-204; Kafri T. 2004. Mol. Biol. 246:367-390; Balaggan and Ali. 2012. Gene Ther. 19:145-153; Wong et al. 2006. Hum. Gen. Ther. 2002. 17:1-9; Azzouz et al. J. Neruosci. 22L10302-10312; and Betchen and Kaplitt. 2003. Curr. Opin. Neurol. 16:487-493, whose techniques and vectors described therein can be modified and adapted for use in the engineered APC and/or antigen of the present invention.

Poxvirus Vectors

In some embodiments, the vector can be a poxvirus vector or system thereof. In some embodiments, the poxvirus vector can result in cytoplasmic expression of one or more engineered APC and/or antigen polynucleotides of the present invention. In some embodiments the capacity of a poxvirus vector or system thereof can be about 25 kb or more. In some embodiments, a poxvirus vector or system thereof can include an engineered APC encoding polynucleotide and/or antigen of the present invention.

Vector Construction

The vectors described herein can be constructed using any suitable process or technique. In some embodiments, one or more suitable recombination and/or cloning methods or techniques can be used to the vector(s) described herein. Suitable recombination and/or cloning techniques and/or methods can include, but not limited to, those described in U.S. Application publication No. US 2004-0171156 A1. Other suitable methods and techniques are described elsewhere herein.

Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Any of the techniques and/or methods can be used and/or adapted for constructing an AAV or other vector described herein.

In some embodiments, the vector can have one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors.

Delivery vehicles, vectors, particles, nanoparticles, formulations and components thereof for expression of one or more elements of an engineered APC and/or antigen described herein are as used in the foregoing documents, such as WO 2014/093622 (PCT/US2013/074667) and are discussed in greater detail herein.

Virus Particle Production from Viral Vectors

Retroviral Production

In some embodiments, one or more viral vectors and/or system thereof can be delivered to a suitable cell line for production of virus particles containing the polynucleotide or other payload to be delivered to a hosT-cell. Suitable hosT-cells for virus production from viral vectors and systems thereof described herein are known in the art and are commercially available. For example, suitable hosT-cells include HEK 293 cells and its variants (HEK 293T and HEK 293TN cells). In some embodiments, the suitable hosT-cell for virus production from viral vectors and systems thereof described herein can stably express one or more genes involved in packaging (e.g. pol, gag, and/or VSV-G) and/or other supporting genes.

In some embodiments, after delivery of one or more viral vectors to the suitable hosT-cells for or virus production from viral vectors and systems thereof, the cells are incubated for an appropriate length of time to allow for viral gene expression from the vectors, packaging of the polynucleotide to be delivered (e.g. an engineered APC and/or antigen polynucleotide), and virus particle assembly, and secretion of mature virus particles into the culture media. Various other methods and techniques are generally known to those of ordinary skill in the art.

Mature virus particles can be collected from the culture media by a suitable method. In some embodiments, this can involve centrifugation to concentrate the virus. The titer of the composition containing the collected virus particles can be obtained using a suitable method. Such methods can include transducing a suitable cell line (e.g. NIH 3T3 cells) and determining transduction efficiency, infectivity in thaT-cell line by a suitable method. Suitable methods include PCR-based methods, flow cytometry, and antibiotic selection-based methods. Various other methods and techniques are generally known to those of ordinary skill in the art. The concentration of virus particle can be adjusted as needed. In some embodiments, the resulting composition containing virus particles can contain $1 \times 10^1$-$1 \times 10^{20}$ particles/mL.

AAV Particle Production

There are two main strategies for producing AAV particles from AAV vectors and systems thereof, such as those described herein, which depend on how the adenovirus helper factors are provided (helper v. helper free). In some embodiments, a method of producing AAV particles from AAV vectors and systems thereof can include adenovirus infection into cell lines that stably harbor AAV replication and capsid encoding polynucleotides along with AAV vector containing the polynucleotide to be packaged and delivered by the resulting AAV particle (e.g. the engineered APC and/or antigen polynucleotide(s)). In some embodiments, a method of producing AAV particles from AAV vectors and systems thereof can be a "helper free" method, which includes co-transfection of an appropriate producing cell line with three vectors (e.g. plasmid vectors): (1) an AAV vector that contains a polynucleotide of interest (e.g. the engineered APC and/or antigen polynucleotide(s)) between 2 ITRs; (2) a vector that carries the AAV Rep-Cap encoding polynucleotides; and (helper polynucleotides. One of skill in the art will appreciate various methods and variations thereof that are both helper and -helper free and as well as the different advantages of each system.

Vector and Virus Particle Delivery

A vector (including non-viral carriers) described herein can be introduced into hosT-cells to thereby produce transcripts, proteins, or peptides, including fusion proteins or peptides encoded by nucleic acids as described herein (e.g., engineered APC and/or antigen transcripts, proteins, enzymes, mutant forms thereof, fusion proteins thereof, etc.), and virus particles (such as from viral vectors and systems thereof).

One or more engineered APC and/or antigen polynucleotides can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus.

For plasmid delivery, the route of administration, formulation and dose can be as in U.S. Pat. No. 5,846,946 and as in clinical studies involving plasmids. In some embodiments, doses can be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into or otherwise delivered to the tissue or cell of interest.

In terms of in vivo delivery, AAV is advantageous over other viral vectors for a couple of reasons such as low toxicity (this may be due to the purification method not requiring ultra-centrifugation of cell particles that can activate the immune response) and a low probability of causing insertional mutagenesis because it doesn't integrate into the host genome.

The vector(s) and virus particles described herein can be delivered in to a hosT-cell in vitro, in vivo, and/or ex vivo. Delivery can occur by any suitable method including, but not limited to, physical methods, chemical methods, and biological methods. Physical delivery methods are those methods that employ physical force to counteract the membrane barrier of the cells to facilitate intracellular delivery of the vector. Suitable physical methods include, but are not limited to, needles (e.g. injections), ballistic polynucleotides (e.g. particle bombardment, micro projectile gene transfer, and gene gun), electroporation, sonoporation, photoporation, magnetofection, hydroporation, and mechanical massage. Chemical methods are those methods that employ a chemical to elicit a change in the cells membrane permeability or other characteristic(s) to facilitate entry of the vector into the cell. For example, the environmental pH can be altered which can elicit a change in the permeability of the cell membrane. Biological methods are those that rely and capitalize on the hosT-cell's biological processes or biological characteristics to facilitate transport of the vector (with or without a carrier) into a cell. For example, the vector and/or its carrier can stimulate an endocytosis or similar process in the cell to facilitate uptake of the vector into the cell.

Delivery of engineered APC and/or antigen components (e.g. polynucleotides encoding engineered APC and/or antigen polypeptides) to cells via particles. The term "particle" as used herein, refers to any suitable sized particles for delivery of the engineered APC and/or antigen components described herein. Suitable sizes include macro-, micro-, and nano-sized particles. In some embodiments, any of the engineered APC and/or antigen components (e.g. polypeptides, polynucleotides, vectors and combinations thereof described herein) can be attached to, coupled to, integrated with, otherwise associated with one or more particles or component thereof as described herein. The particles described herein can then be administered to a cell or organism by an appropriate route and/or technique. In some embodiments, particle delivery can be selected and be advantageous for delivery of the polynucleotide or vector components. It will be appreciated that in embodiments, particle delivery can also be advantageous for other engineered APC and/or antigen molecules and formulations described elsewhere herein.

Methods of Modulating an Immune Response

The engineered APCs described herein can modulate an immune response of a T-cell, such as a target T-cell, and thus can modulate the immune response of a subject to which the engineered APCs are delivered to. In some embodiments, the engineered APCs can be used to modify the response of or otherwise regulate an engineered T-cell, such as a CAR-T-cell, that is also administered to a subject. The engineered APCs can modulate a T-cell or other immune cell response via delivery of one or more T-cell modulating agents to a target T-cell or a T or other cell that is in effective proximity of the target T-cell. In at least these ways, the engineered APCs described herein can be used to treat and/or prevent an immune or immune mediated disease and/or a symptom thereof in a subject in need thereof.

As used throughout this specification, the terms "treat", "treating" and "treatment" refer to the alleviation or measurable lessening of one or more symptoms or measurable markers of a pathological condition such as a disease or disorder. Measurable lessening includes any statistically significant decline in a measurable marker or symptom. Generally, the terms encompass both curative treatments and treatments directed to reduce symptoms and/or slow progression of the disease. The terms encompass both the therapeutic treatment of an already developed pathological condition, as well as prophylactic or preventative measures, wherein the aim is to prevent or lessen the chances of incidence of a pathological condition. In certain embodiments, the terms may relate to therapeutic treatments. In certain other embodiments, the terms may relate to preventative treatments. Treatment of a chronic pathological condition during the period of remission may also be deemed to constitute a therapeutic treatment. The term may encompass ex vivo or in vivo treatments as appropriate in the context of the present invention.

As used throughout this specification, the terms "prevent", "preventing" and "prevention" refer to the avoidance or delay in manifestation of one or more symptoms or measurable markers of a pathological condition, such as a disease or disorder. A delay in the manifestation of a symptom or marker is a delay relative to the time at which such symptom or marker manifests in a control or untreated subject with a similar likelihood or susceptibility of developing the pathological condition. The terms "prevent", "preventing" and "prevention" include not only the avoidance or prevention of a symptom or marker of the pathological condition, but also a reduced severity or degree of any one of the symptoms or markers of the pathological condition, relative to those symptoms or markers in a control or non-treated individual with a similar likelihood or susceptibility of developing the pathological condition, or relative to symptoms or markers likely to arise based on historical or statistical measures of populations affected by the disease or disorder. By "reduced severity" is meant at least a 10% reduction in the severity or degree of a symptom or measurable marker relative to a control or reference, e.g., at least 15%, 20%, 30%, 40%, 50%, 60%, 70%, 80%, 90%, 95%, 99% or even 100% (i.e., no symptoms or measurable markers).

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic embodiments of an immune cell or immune cell population may be modulated without substantially altering other (unintended, undesired) phenotypic embodiment(s).

In certain embodiments, the immune cell or immune cell population (such as the engineered APC or engineered APC population described herein) is autologous to said subject, i.e., the immune cell or immune cell population (such as the engineered APC or engineered APC population described herein) is isolated from the same subject as the subject to which/whom the immune cell or immune cell population is to be administered. In certain further embodiments, the immune cell or immune cell population (such as the engineered APC or engineered APC population described herein) is syngeneic to said subject, i.e., the immune cell or immune cell population is isolated from an identical twin of the subject to which/whom the immune cell or immune cell population is to be administered. In certain further embodiments, the immune cell or immune cell population (such as the engineered APC or engineered APC population described herein) is allogeneic to said subject, i.e., the immune cell or immune cell population is isolated from a different subject of the same species as the subject to which/whom the immune cell or immune cell population is to be administered. In certain embodiments, the immune cell or immune cell population (such as the engineered APC or engineered APC population described herein) can be xenogeneic to said subject, i.e., the immune cell or immune cell population may be isolated from a subject of a different species than the subject to which/whom the immune cell or immune cell population is to be administered. It will be appreciated that when an engineered APC is said to be allogenic, it means that the cell that is modified to produce the engineered APC was isolated from a different subject the same species as the subject to which/whom it is to be administered. Likewise, it will be appreciated that when an engineered APC is said to autologous it means that the cell that is modified to produce the engineered APC was isolated from the same subject to which/whom it is to be administered.

In some embodiments, autologous cells can be selected such as to maximise the tissue compatibility between the subject and the administered cells, thereby reducing the chance of rejection of the administered cells by patient's immune system or graft-vs.-host reaction. For example, advantageously the cells may be typically selected which have either identical HLA haplotypes (including one or preferably more HLA-A, HLA-B, HLA-C, HLA-D, HLA-DR, HLA-DP and HLA-DQ) to the subject, or which have the most HLA antigen alleles common to the subject and none or the least of HLA antigens to which the subject contains pre-existing anti-HLA antibodies.

Approaches such as the foregoing may be adapted to provide methods of treating, preventing, and/or increasing survival of a subject having a disease or a symptom thereof by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T-cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

Activating an Immune Response or Immune Cell

In some embodiments, the engineered APC can stimulate activation of an immune response or more particularly a T-cell response, in a target T-cell and/or a cell within effective proximity to the target T-cell. "Activation" generally refers to the state of a cell, such as preferably T-cell, following sufficienT-cell surface moiety ligation (e.g., interaction between the T-cell receptor on the surface of a T-cell (such as naturally-occurring TCR or genetically engineered TCR, e.g., chimeric antigen receptor, CAR) and MHC-bound antigen peptide presented on the surface of the immune cell (e.g. engineered APC) as taught herein) to induce a noticeable biochemical or morphological change of the cell, such as preferably T-cell. In particular, "activation" may refer to the state of a T-cell that has been sufficiently stimulated to induce detectable cellular proliferation of the T-cell. Activation can also encompass induced cytokine production, and detectable T-cell effector functions, e.g., regulatory or cytolytic effector functions. The T-cells and immune cells may be suitably contacted by admixing the T-cells and immune cells in an aqueous composition, e.g., in a culture medium, in sufficient numbers and for a sufficient duration of time to produce the desired T-cell activation. As is described elsewhere herein the T-cell can be a target T-cell.

Inhibiting or Ablating an Immune Response or Immune Cell

In some embodiments, the engineered APC can trigger inhibition or ablation of an immune response or more particularly a T-cell response, in a target T-cell and/or a cell within effective proximity to the target T-cell. "Inhibition" generally refers to the state of a cell, such as preferably T-cell, following sufficienT-cell surface moiety ligation (e.g., interaction between the T-cell receptor on the surface of a T-cell (such as naturally-occurring TCR or genetically engineered TCR, e.g., chimeric antigen receptor, CAR) and MHC-bound antigen peptide presented on the surface of the immune cell (e.g. engineered APC) as taught herein) to induce a noticeable biochemical or morphological change of the cell, such as preferably T-cell. In particular, "inhibition" may refer to the state of a T-cell that has been sufficiently inhibited such that there is no detectable cellular proliferation of the T-cell. Inhibition can also encompass reduced or eliminated cytokine production, and detectable T-cell effector functions, e.g., regulatory or cytolytic effector functions. The T-cells and immune cells may be suitably contacted by admixing the T-cells and immune cells in an aqueous composition, e.g., in a culture medium, in sufficient numbers and for a sufficient duration of time to produce the desired T-cell inhibition. As is described elsewhere herein the T-cell can be a target T-cell.

As used in this context "ablation" refers to the elimination to at least below detectable levels of T-cell proliferation and any effector or regulatory function of the T-cell, such as the target T-cell. Ablation also includes death of the T-cell, such as the target T-cell, which would necessarily result in elimination of T-cell functions.

Adoptive Cell Therapy

Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

The engineered APCs described herein can be used as an adoptive cell therapy in a subject in need thereof. In some embodiments, the engineered APCs can be used as a co-therapy with another adoptive therapy (e.g. CAR-T-cells).

In some embodiments, a method can include delivering an autologous engineered APC to a subject in need thereof via an appropriate administration route. In some embodiments, the subject has or will also be treated with another adoptive cell therapy.

Diseases to be Treated or Prevented

As used herein, the terms "disease" or "disorder" are used interchangeably throughout this specification, and refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, indisposition, or affliction.

In certain embodiments, the pathological condition may be an infection, inflammation, proliferative disease, autoimmune disease, or allergy. In some embodiments, the disease is an inflammatory disease.

As used herein, "infection" as used herein refers to presence of an infective agent, such as a pathogen, e.g., a microorganism, in or on a subject, which, if its presence or growth were inhibited, would result in a benefit to the subject. Hence, the term refers to the state produced by the establishment, more particularly invasion and multiplication, of an infective agent, such as a pathogen, e.g., a microorganism, in or on a suitable host. An infection may produce tissue injury and progress to overt disease through a variety of cellular and toxic mechanisms.

As used herein, "inflammation" generally refers to a response in vasculated tissues to cellular or tissue injury usually caused by physical, chemical and/or biological agents, that is marked in the acute form by the classical sequences of pain, heat, redness, swelling, and loss of function, and serves as a mechanism initiating the elimination, dilution or walling-off of noxious agents and/or of damaged tissue. Inflammation histologically involves a complex series of events, including dilation of the arterioles, capillaries, and venules with increased permeability and blood flow, exudation of fluids including plasma proteins, and leukocyte migration into the inflammatory focus.

Further, the term encompasses inflammation caused by extraneous physical or chemical injury or by biological agents, e.g., viruses, bacteria, fungi, protozoan or metazoan parasite infections, as well as inflammation which is seemingly unprovoked, e.g., which occurs in the absence of demonstrable injury or infection, inflammation responses to self-antigens (auto-immune inflammation), inflammation responses to engrafted xenogeneic or allogeneic cells, tissues or organs, inflammation responses to allergens, etc. The term covers both acute inflammation and chronic inflammation. Also, the term includes both local or localised inflammation, as well as systemic inflammation, i.e., where one or more inflammatory processes are not confined to a particular tissue but occur generally in the endothelium and/or other organ systems.

Systemic inflammatory conditions may particularly encompass systemic inflammatory response syndrome (SIRS) or sepsis. "SIRS" is a systemic inflammatory response syndrome with no signs of infection. It can be characterised by the presence of at least two of the four following clinical criteria: fever or hypothermia (temperature of 38.0° C.) or more, or temperature of 36.0° C. or less); tachycardia (at least 90 beats per minute); tachypnea (at least 20 breaths per minute or $PaCO_2$ less than 4.3 kPa (32.0 mm Hg) or the need for mechanical ventilation); and an altered white blood cell (WBC) count of $12 \times 10^6$ cells/mL or more, or an altered WBC count of $4 \times 10^6$ cells/mL or less, or the presence of more than 10% band forms. "Sepsis" can generally be defined as SIRS with a documented infection, such as for example a bacterial infection. Infection can be diagnosed by standard textbook criteria or, in case of uncertainty, by an infectious disease specialist. Bacteraemia is defined as sepsis where bacteria can be cultured from blood. Sepsis may be characterised or staged as mild sepsis, severe sepsis (sepsis with acute organ dysfunction), septic shock (sepsis with refractory arterial hypotension), organ failure, multiple organ dysfunction syndrome and death.

As used herein, "proliferative disease" generally refers to any disease or disorder characterised by neoplastic cell growth and proliferation, whether benign, pre-malignant, or malignant. The term proliferative disease generally includes all transformed cells and tissues and all cancerous cells and tissues. Proliferative diseases or disorders include, but are not limited to abnormal cell growth, benign tumours, pre-malignant or precancerous lesions, malignant tumors, and cancer.

The terms "tumor" or "tumor tissue" refer to an abnormal mass of tissue resulting from excessive cell division. A tumor or tumor tissue comprises "tumor cells" which are neoplastic cells with abnormal growth properties and no useful bodily function. Tumors, tumor tissue and tumor cells may be benign, pre-malignant or malignant, or may represent a lesion without any cancerous potential. A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

The term "cancer" refers to a malignant neoplasm characterised by deregulated or unregulated cell growth. The term "cancer" includes primary malignant T-cells or tumors (e.g., those whose cells have not migrated to sites in the subject's body other than the site of the original malignancy or tumor) and secondary malignant T-cells or tumors (e.g., those arising from metastasis, the migration of malignant T-cells or tumor cells to secondary sites that are different from the site of the original tumor. The term "metastatic" or "metastasis" generally refers to the spread of a cancer from one organ or tissue to another non-adjacent organ or tissue.

The occurrence of the proliferative disease in the other non-adjacent organ or tissue is referred to as metastasis.

Examples of cancer include but are not limited to: carcinoma, lymphoma, blastoma, sarcoma, and leukaemia or lymphoid malignancies. More particular examples of such cancers include without limitation: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulvar cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, or haematological cancer.

Other non-limiting examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumours, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Glioblastoma, Childhood Cerebellar Astrocytoma, Childhood Cerebral Astrocytoma, Childhood Extracranial Germ Cell Tumours, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumours, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas islet cell Carcinoma, Endometrial Cancer, Ependymoma, Epithelial Cancer, Esophageal Cancer, Ewing's Sarcoma and Related Tumours, Exocrine Pancreatic Cancer, Extracranial Germ Cell Tumour, Extragonadal Germ Cell Tumour, Extrahepatic Bile Duct Cancer, Eye Cancer, Female Breast Cancer, Gaucher's Disease, Gallbladder Cancer, Gastric Cancer, Gastrointestinal Carcinoid Tumour, Gastrointestinal Tumours, Germ Cell Tumours, Gestational Trophoblastic Tumour, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet cell Carcinoma, Islet cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumour, Pancreatic Cancer, Paraproteinemias, Purpura, Parathyroid Cancer, Penile Cancer, Pheochromocytoma, Pituitary Tumour, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumours, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, or Wilms' Tumour.

As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjögren's syndrome; systemic lupus erythematosus; Takayasu's arteritis;

temporal arteritis; vitiligo; warm autoimmune hemolytic anemia; or Wegener's granulomatosis.

Any such diseases, disorders, and/or symptoms thereof described herein can, in some embodiments, be treated or prevented by administration of one or more engineered APCs described herein to the subject in need thereof.

Further embodiments are illustrated in the following Examples which are given for illustrative purposes only and are not intended to limit the scope of the invention.

EXAMPLES

Example 1—Engineered B Cells Loaded with and/or Expressing a Target T-Cell Specific Antigen This example can demonstrate B cells capable of targeting antigen-specific T-cells by incorporating a T-cell specific antigen into the B cell for processing and presentation in one or more MHC molecules. The target T-cell specific antigen can be an extracellular target T-cell antigen that can be loaded into a cell via a B cell receptor mediated antigen sampling pathway or other B cell extracellular antigen sampling mechanism. The target T-cell specific antigen can be incorporated into an expression construct or vector, which can be introduced to the cell using an appropriate technique and can express the target T-cell specific antigen as an intracellular antigen.

The loading and/or expression of a target T-cell specific antigen into the B cell in this Example is described in the context of otherwise unmodified or native B cells. However, it will be appreciated by those of ordinary skill in the art that the approaches and techniques can be coupled with and applied to other B cell engineering strategies described herein.

To this end, B-cells can be engineered to first be e.g. loaded with an extracellular target T-cell antigen ex vivo to program these B cells to target antigen-specific T-cells by presenting peptides on major histocompatibility complexes (MHCs). Antigen processing pathways of the B cell can result in the presentation of the extracellular target T-cell antigen into one or more MHC molecules.

The B cells can be engineered to express a target T-cell specific antigen intracellularly. A B cell described herein (native or otherwise engineered as described elsewhere herein) can be modified by introducing an expression construct capable of producing a target T-cell specific antigen inside the B cell via a suitable genetic modification technique. The produced target T-cell specific antigen can be processed by an antigen presentation pathway such that it is expressed on an MHC molecule.

Although native B cells express a cross-presentation pathway that can result in expression of an antigen, whether it be an extracellular or intracellular antigen, in both MCH I and MHC II molecules, depending on the source (intracellular or extracellular) the antigen can be primarily or exclusively presented in a MHC I molecule or a MHC II molecule. The processing/presentation pathway for intracellular originating antigens can result in primary or exclusive presentation of the processed antigen in MHC I molecules. The processing/presentation pathway for extracellular originating antigens can result in primary or exclusive presentation of the processed antigen in MHC II molecules.

The extent of MHC I or MHC I presentation exclusivity will depend on the extent of cross-presentation facilitated by processing of the intracellularly produced antigen through the cross-presentation pathway. The expression in MHC I vs MHC II can be evaluated using an appropriate method (e.g. employing techniques using antibodies specific for MHC I-peptide or MHC-II peptide complexes), which are described and/or demonstrated elsewhere herein. The B-cells presenting the extracellular and/or intracellular target T-cell specific antigen can be optionally screened for desired presentation of the target T-cell specific antigen using an appropriate screening method. Suitable screening can include FACS or other technique using an antibody or fragment thereof specific to the MHC I-peptide or MHC II-peptide complex in a fashion similar to that shown in FIGS. 4-6B. The selected cells can be further modified as desired, expanded, and/or otherwise manipulated, and/or administered to a subject in need thereof.

Example 2—Engineered B Cells with Recombinant B Cell Receptors

The B cells can be modified to express a recombinant B cell receptor. The recombinant B cell receptor can be engineered to recognize or be specific for a tag that can be operably coupled to an antigen to be loaded into the B cell as previously described. As shown in e.g. FIG. 1, a viral vector (such as a lentivirus, e.g. lentivirus pseudotyped for measles) can be used to modify a B cell (either a native B cell or any other engineered B cell described elsewhere herein) to express a recombinant B cell receptor specific to a tag molecule such as FLAG. The peptide or polypeptide antigen can be operably coupled to that tag molecule, e.g. FLAG, such that the B cell receptor will specifically recognize the tagged antigen and thus more efficiently increase its uptake into the B cell for processing and presentation by the B cell. See also e.g. FIGS. 1 and 3.

Example 3—Engineered B Cells with Modified Antigen Presentation Pathways

As demonstrated in Example 1, the presentation of the antigen in MHC I and/or MHC II is a function of whether the antigen is extracellular or intracellular and how much cross-presentation there is. It can be desirable to achieve a specifically desired antigen presentation profile on major histocompatibility complex (MHC) I and/or MHCII molecules. For example, it can be desirable to express an extracellular target T-cell specific antigen in an MHC I molecule because the target T-cell is a CD8+ T-cell. CD8+ T-cells have T-cell receptors (TCRs) that recognize MHC I molecules. For example, if an extracellular target T-cell antigen is loaded into a B cell, such as a B cell having a recombinant BCR as demonstrated in Examples 1 and 2, without any other modification it would most likely be primarily presented in MHC II molecules, which would not be as effective at targeting a target CD8+ T-cell as if the antigen were expressed in MHC I molecules. Also, by way of example, CD4+ T-cells have T-cell receptors (TCRs) that recognize MHC II molecules. Thus, if the B cells were engineered to intracellularly express a target T-cell antigen (see e.g. Example 1), without any modification to the antigen processing and/or presentation pathways, the antigen would primarily be expressed in MHC I molecules, which would not be as effective at targeting a target CD4+ T-cell as if the antigen were expressed in MHC IL molecules.

Described in this Example are engineered B cells that can have modified presentation pathways such that presentation of the antigen in MHC molecules can be controlled and optimized to achieve a desired presentation profile optimized for the MHC preference of the target T-cell. In some embodiments, this can involve modification of the cross-presentation capacity, MHC I presentation capacity, and/or MHC II presentation capacity of a B cell. A genome-wide CRISPR-Cas9 knockout screen in primary human B cells can be used to identify genes that regulate cross-presentation or other embodiments of antigen processing and/or presentation in MHC complexes in the B cell. Details of such CRISPR-based screens are also described elsewhere herein. Engineered B cells having a specific or desired antigen presentation capability (e.g. presentation in one or both of MHC I or II molecules) can then made by modulating the expression of one or more genes in an antigen processing or presentation pathway identified by the aforementioned screen in a B cell (native or as otherwise describe and/or demonstrated elsewhere herein). The engineered B cells (eBCs) thus can have a desired antigen presentation profile and can allow for efficient targeting of the target T-cell.

FIG. 1—shows a strategy for generating and screening engineered antigen presenting cells (e.g. engineered B-cells) having a desired presentation of an antigen and/or to determine cross-presentation of antigen by the B cell or screen for B cells expression a desired antigen presenting pathway (e.g. a cross-presentation pathway). In some embodiments, one or more genes in the antigen presenting pathway (e.g. cross-presentation pathway) are modulated using a suitable genetic engineering technique (e.g. a CRISPR-Cas system). In some embodiments, the B-cells can be engineered to express a recombinant B-cell receptor via a suitable technique (e.g. lentiviral vector mediated expression). In some embodiments, the recombinant B cell-receptor can be specific to a known antigen, e.g. a FLAG molecule to which a target T-cell antigen can be attached, which can facilitate loading of the target T-cell antigen into the B cell. B cells expressing the desired antigen presentation pathway can be screened by measuring the expression of MHC I-peptide (antigen) and/or MHC II-peptide (antigen) complexes by the engineered B cell.

Figure 2A:
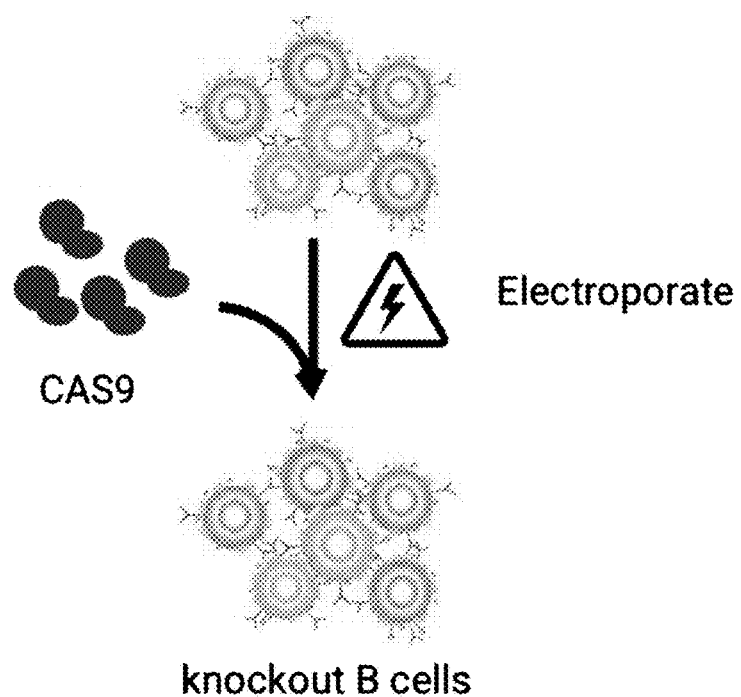
FIGS. 2A-2C—A strategy for engineering B cells to have modulated gene expression of one or more genes, such as one or more genes in an antigen presenting pathway.
Figure 2B:
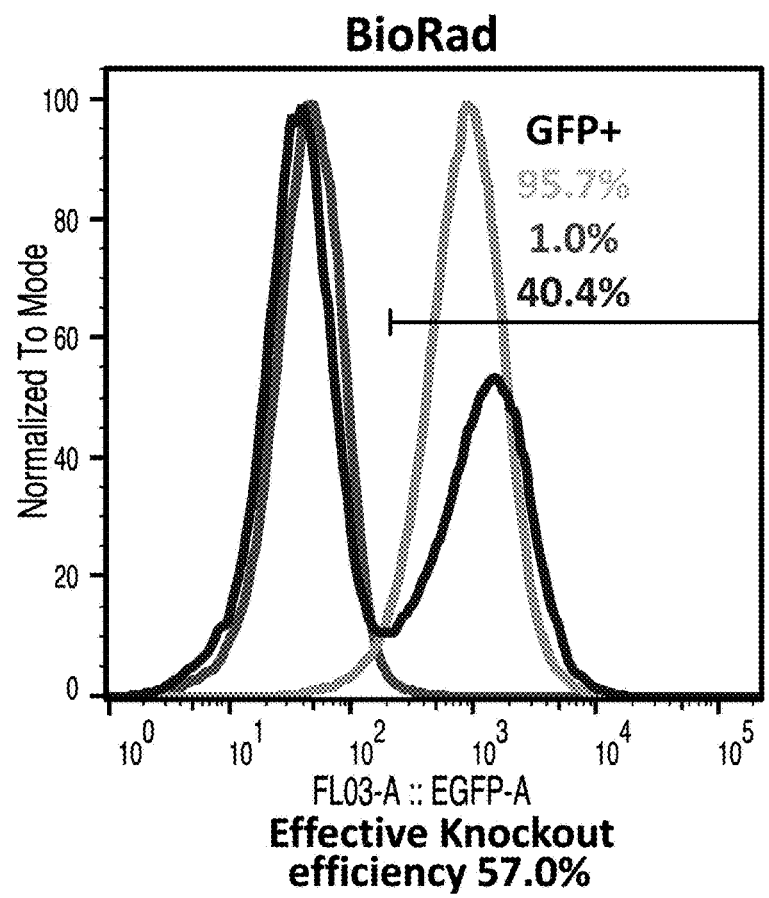
Figure 2C:
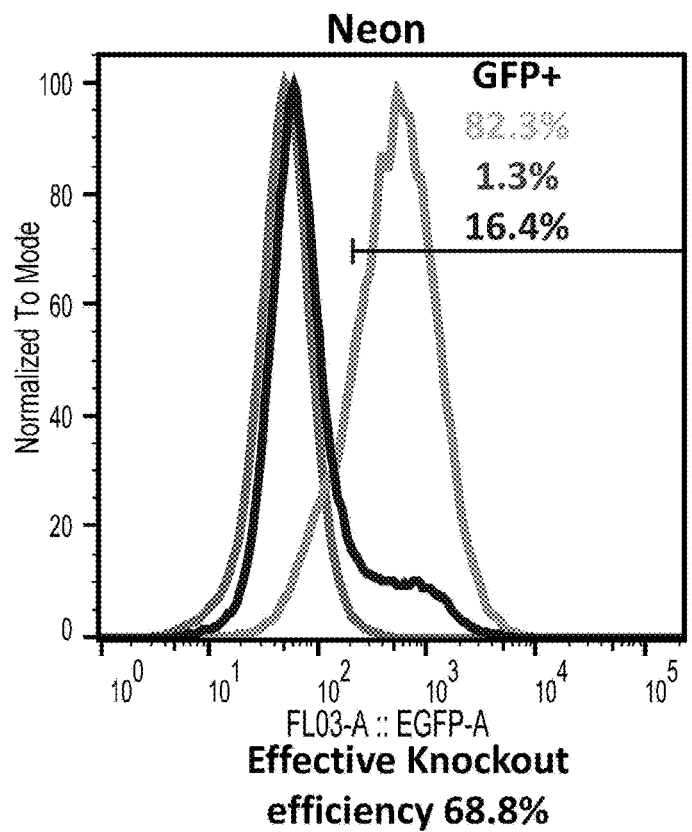
Figure 3:
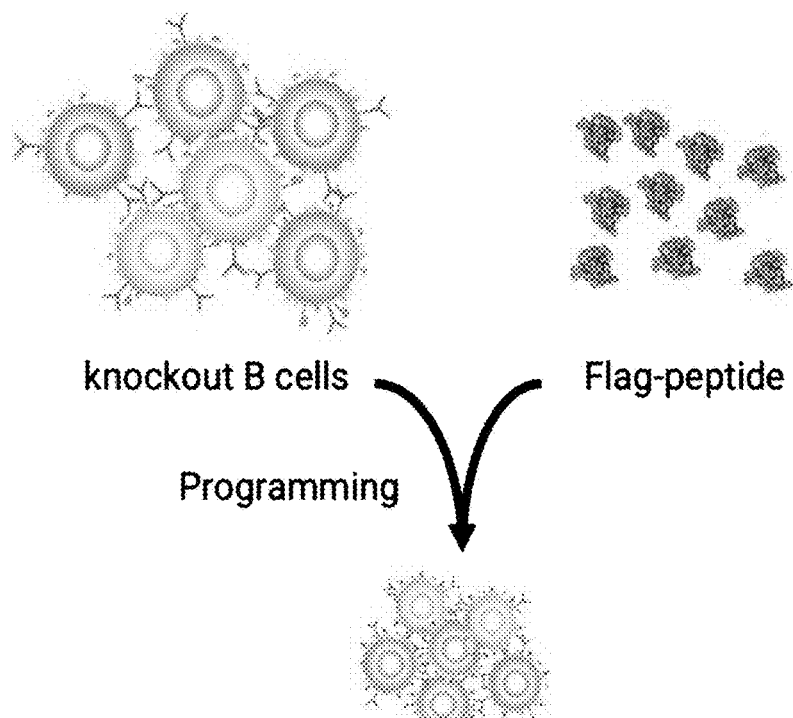
FIG. 3—A strategy to introduce a FLAG-target T-cell peptide antigen into the engineered B cells. As previously discussed, the engineered B cells can express a recombinant FLAG specific B cell receptor, which can target the FLAG-target T-cell peptide antigen complex and facilitate its delivery into the cell for antigen processing and presentation by the B cell.

FIG. 2A-2C—shows a strategy or engineering B cells to have modulated gene expression of one or more genes, such as one or more genes in an antigen presenting pathway. (FIG. 2A) to and graphs (FIGS. 2B-2C) demonstrating knock-out efficiency in the CCL156 cells by a CRISPR-Cas9 system.

Figure 4:
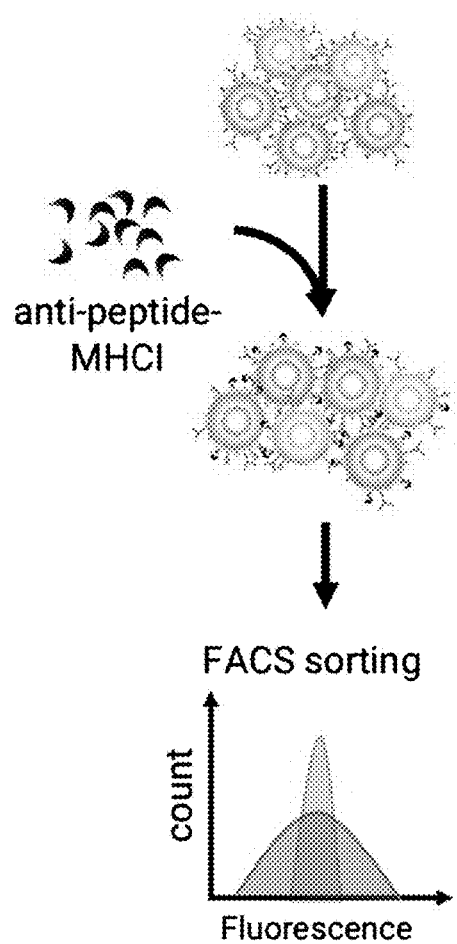
FIG. 4—A strategy for screening for engineered B cells having a desired antigen presentation pathway and/or desired antigen presentation.

FIG. 4—shows a strategy for screening for engineered B cells having a desired antigen presentation pathway and/or desired antigen presentation.

Figure 5:
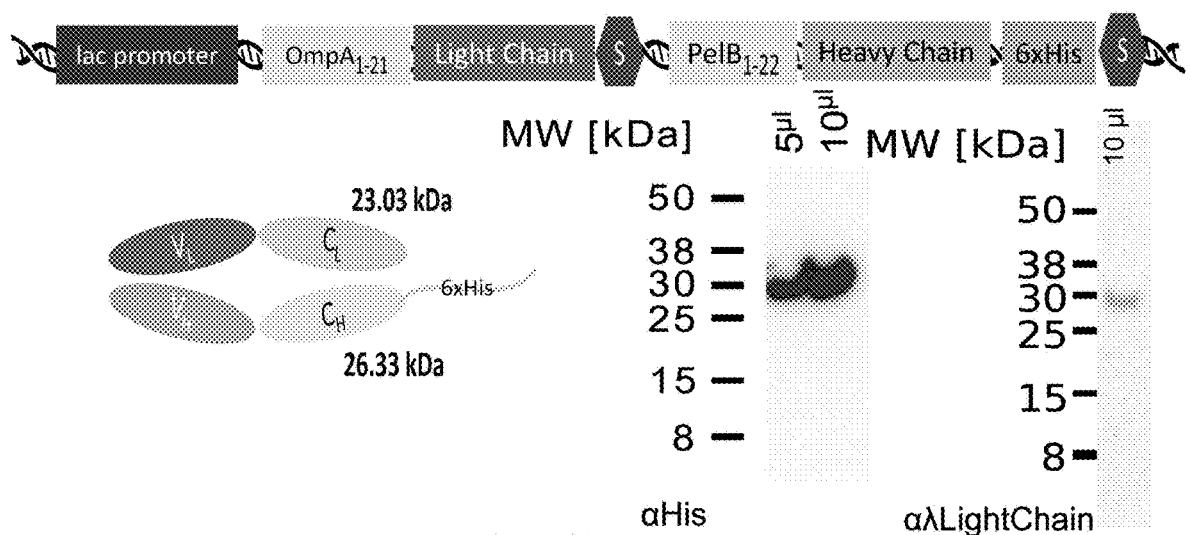
FIG. 5—A strategy and results for purification of a Fab fragment specific for HLA-A2 NYESO-1 peptide complexes.

FIG. 5—shows a strategy and results for purification of a Fab fragment specific for HLA-A2 NYESO-1 peptide complexes, which can more broadly demonstrate development of antibodies or fragments thereof capable of detecting specific MHC-antigen complexes on the surface of the engineered antigen presenting cells herein.

Figure 6A:
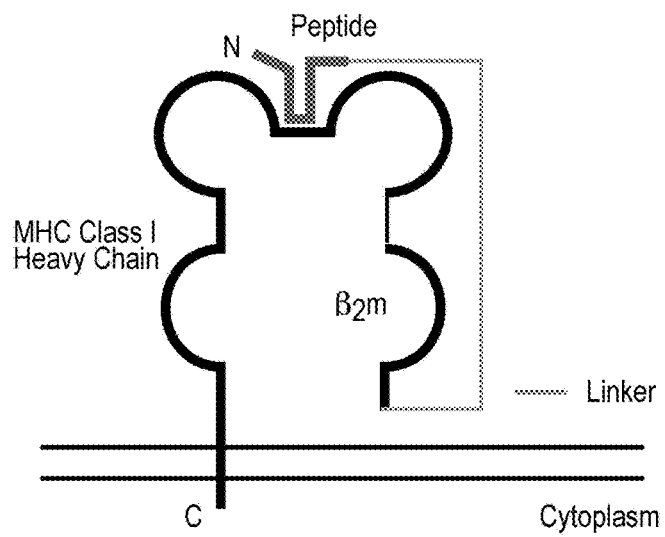
FIGS. 6A-6B—A schematic of peptide presentation by an MHC molecule (FIG. 6A) and specific detection of exemplary MHC-peptide complex (K562-HLA-A2: NYESO1) various concentrations of Fab (FIG. 6B). The K562-HLA-A2:MART1 complex served as a control for the Fab specific to K562-HLA-A2: NYESO1.
Figure 6B:
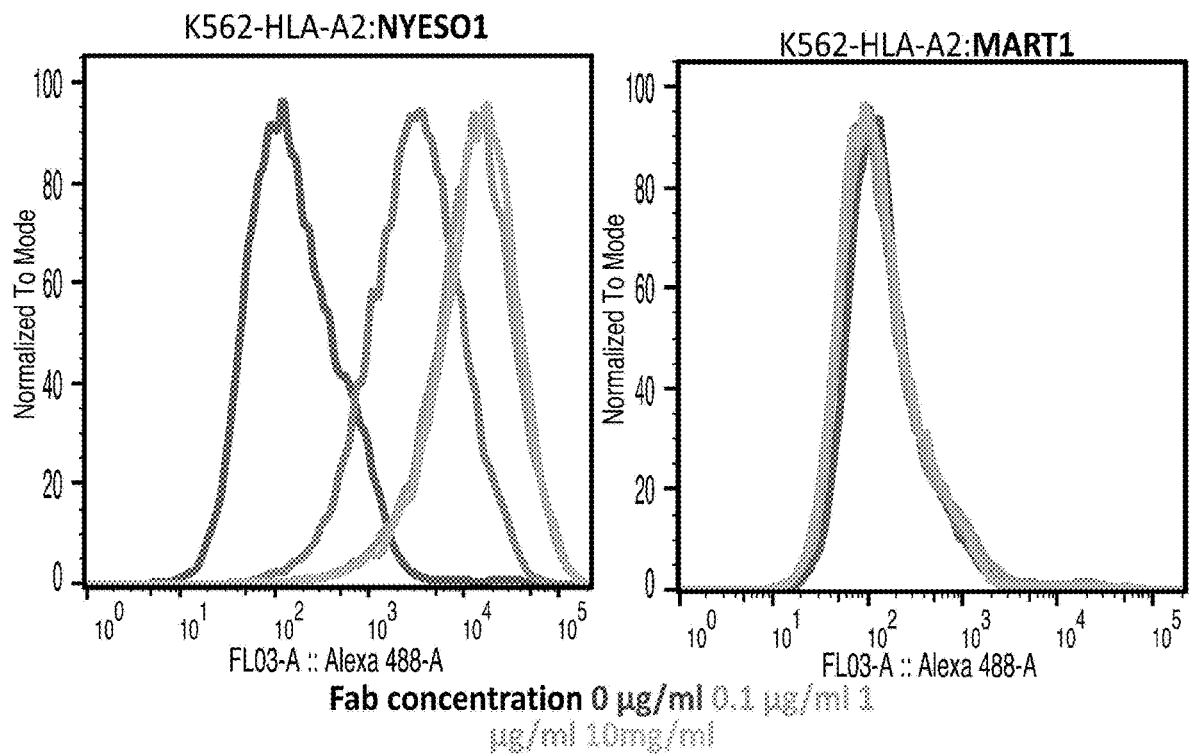

FIGS. 6A-6B—shows a schematic of peptide presentation by an MHC molecule (FIG. 6A) and specific detection of exemplary MHC-peptide complex (K562-HLA-A2: NYESO1) various concentrations of Fab (FIG. 6B). The K562-HLA-A2:MART1 complex served as a control for the Fab specific to K562-HLA-A2: NYESO1.

Figure 7:
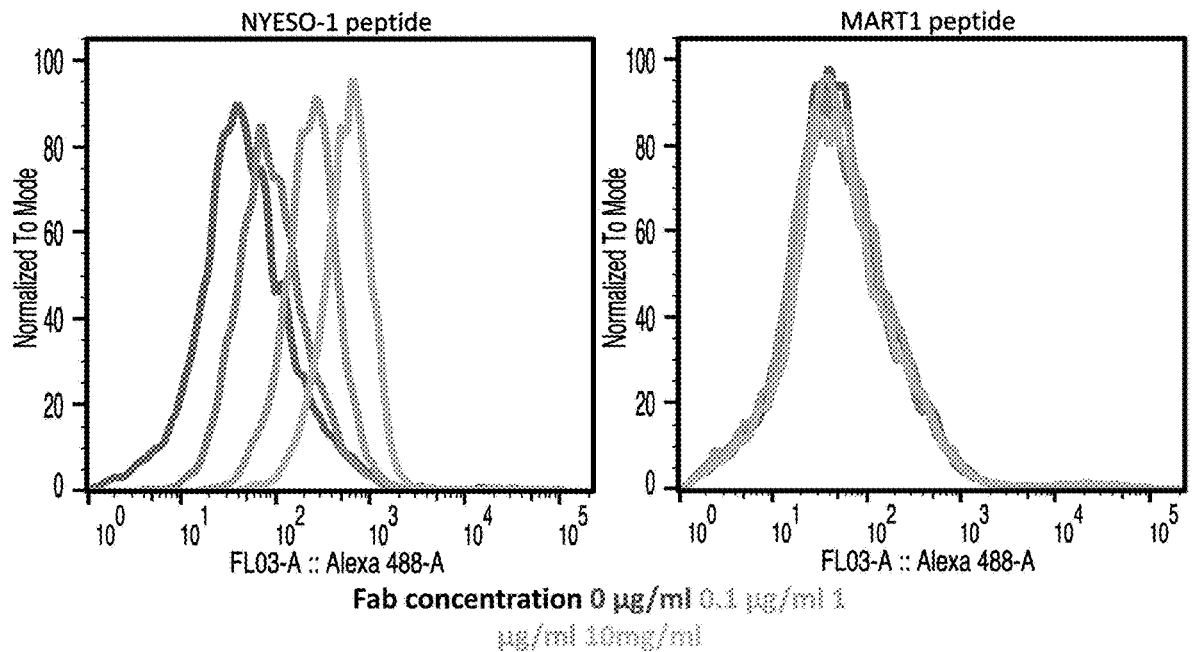
FIG. 7—Specificity of the designed Fab for the desired NYESO-1 peptide antigen that was complexed to the MHC demonstrated in FIGS. 5-6A.

FIG. 7—shows graphs that demonstrate specificity of the designed Fab for the desired NYESO-1 peptide antigen that was complexed to the MHC demonstrated in FIGS. 5-6A.

Figure 11A:
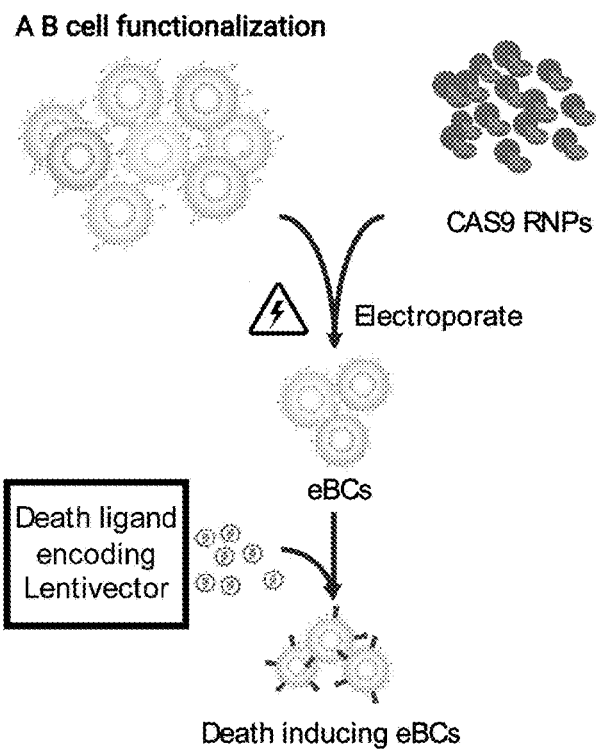
FIGS. 11A-11C—Schematics for engineered B cell functionalization (FIG. 11A), engineered B cell programming (FIG. 11B), and an exemplary application of the engineered B cells in vivo (FIG. 11C). The engineered B cells can be further functionalized (beyond e.g. a desired presentation of a desired antigen) to express other genes or other cargo molecules that can be delivered by the B cell to a target T-cell and used to modulate a target T-cell or another T-cell within effective proximity to a target T-cell.
Figure 11B:
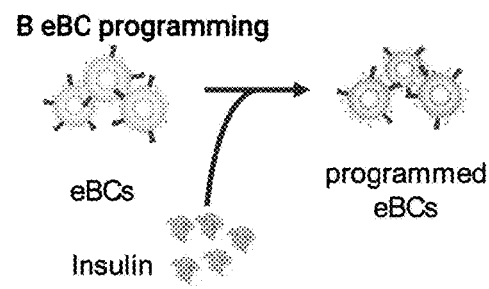

Example 4—Programming Engineered B Cells with Modified Antigen Presentation Pathways It can be desirable to program an engineered B cell described herein to interact with a specific T-cell population based on a known target of the T-cell population like a protein or tumor. Programming via this method does not necessarily require knowledge of the specific TCR antigens because it relies on programming the B cells based on what the desired T-cells specifically interact with. Programming via this method can also result in a heterogenous engineered B cell population that is responsive to multiple T-cells because the population will contain engineered B cells presenting different antigens from the same target protein, cell, or tissue. Engineered B cells having a modified antigen presentation pathway can be programmed as shown in FIG. 11B by incubating the engineered B cells ex vivo with purified protein, cell, or tissue, which will then allow eBCs sample and process various antigens from the purified protein, cell, or tissue and present them in MHC I and/or MHC II cells depending on the expression of the engineered antigen presentation pathway.

Example 5—Isolation and Culture of B Cells for Engineering

B cells suitable for engineering as described herein can be described from either the bone marrow or more advantageously from the peripheral blood. Because suitable B cells for modification are in abundance in the peripheral blood, the engineered B cells described herein are adventurous for autologous adoptive transfer techniques and can be an improvement over others that require more invasive collection of cells to be manipulated than a peripheral blood collection. This Example can demonstrate isolation and in vitro culture of suitable B cells for B cell engineering from the peripheral blood.

Figure 8A:
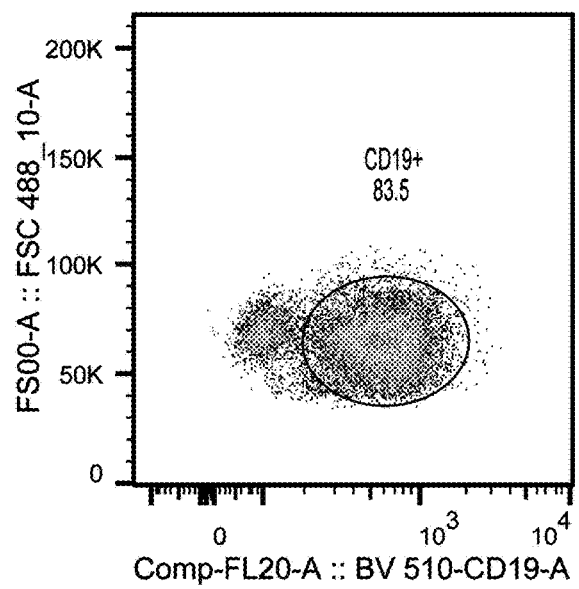
Figures 8B, 8C:
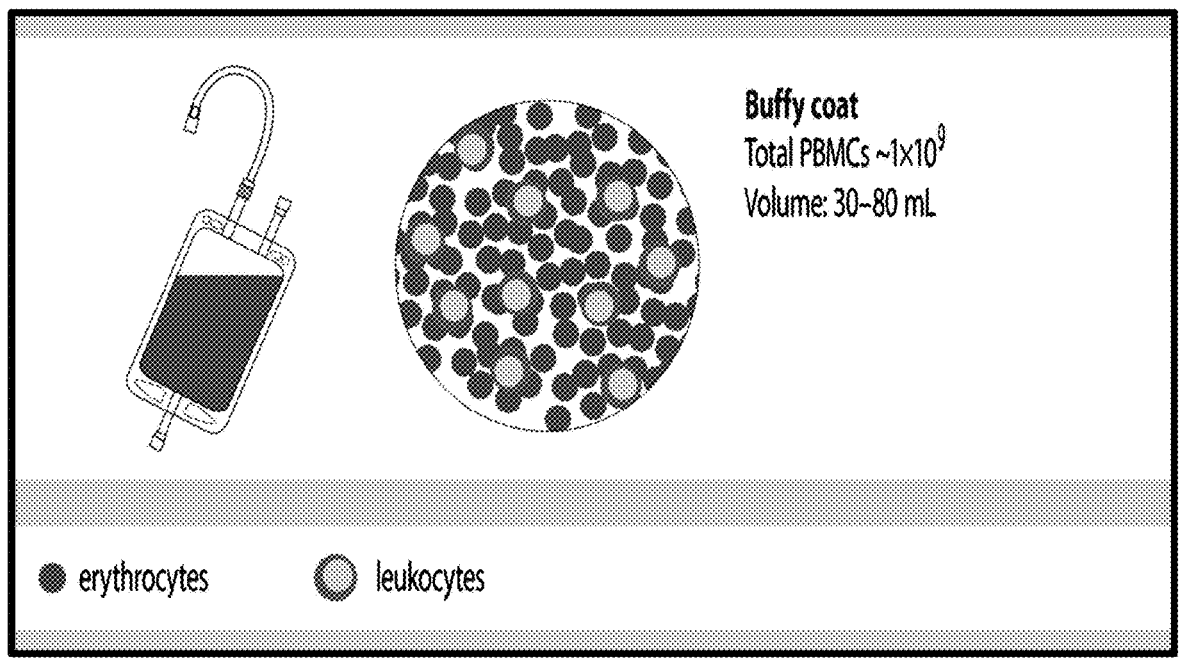

FIGS. 8A-8C—demonstrates isolation using MACS of primary cells from buffy coat of peripheral blood. Monocytes were selected using positive selection with CD14 beads. Pan T-cells and Pan B cells were negatively selected for.

Figures 9A, 9B:
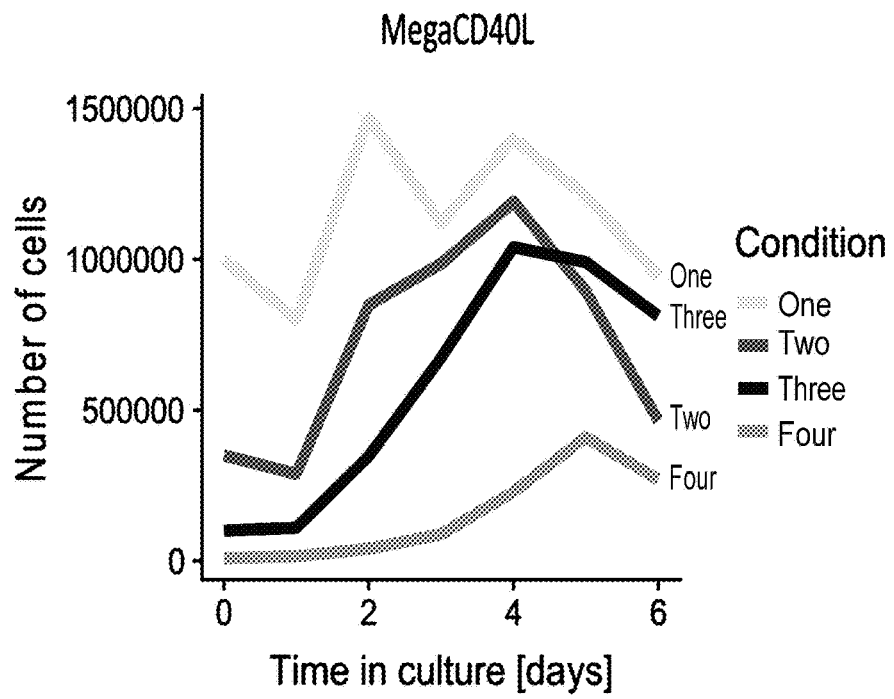
FIGS. 9A-9B—Results from culturing B cells in vitro supplemented with MegaCD40L protein and can demonstrate growth as a function of seeding density over time. Cells were seeded at four densities and cultured for over one week. MegaCD40L protein was replenished on days 2 and 4 in culture to provide a constant source of stimulation. Cells were reseeded on day 6 in culture. It was observed that initial seeding density can affect the B cells ability to expand in vitro, with lowest density of about $1 \times 10^4$ cells per mL seeding density having the greatest fold expansion over a 5 day culture period. It was also observed that the media should be replenished to prevent depletion of nutrients and cytokines. This replenishment can take place at about day 4-5 in culture prior to reseeding.

FIGS. 9A-9B—show a graph (FIG. 9A) and a table (FIG. 9B) showing results from culturing B cells in vitro supplemented with MegaCD40L protein and can demonstrate growth as a function of seeding density over time. Cells were seeded at four densities and cultured for over one week. MegaCD40L protein was replenished on days 2 and 4 in culture to provide a constant source of stimulation. Cells were reseeded on day 6 in culture. It was observed that initial seeding density can affect the B cells ability to expand in vitro, with lowest density of about $1 \times 10^4$ cells per mL seeding density having the greatest fold expansion over a 5 day culture period. It was also observed that the media should be replenished to prevent depletion of nutrients and cytokines. This replenishment can take place at about day 4-5 in culture prior to reseeding.

Figure 10B:
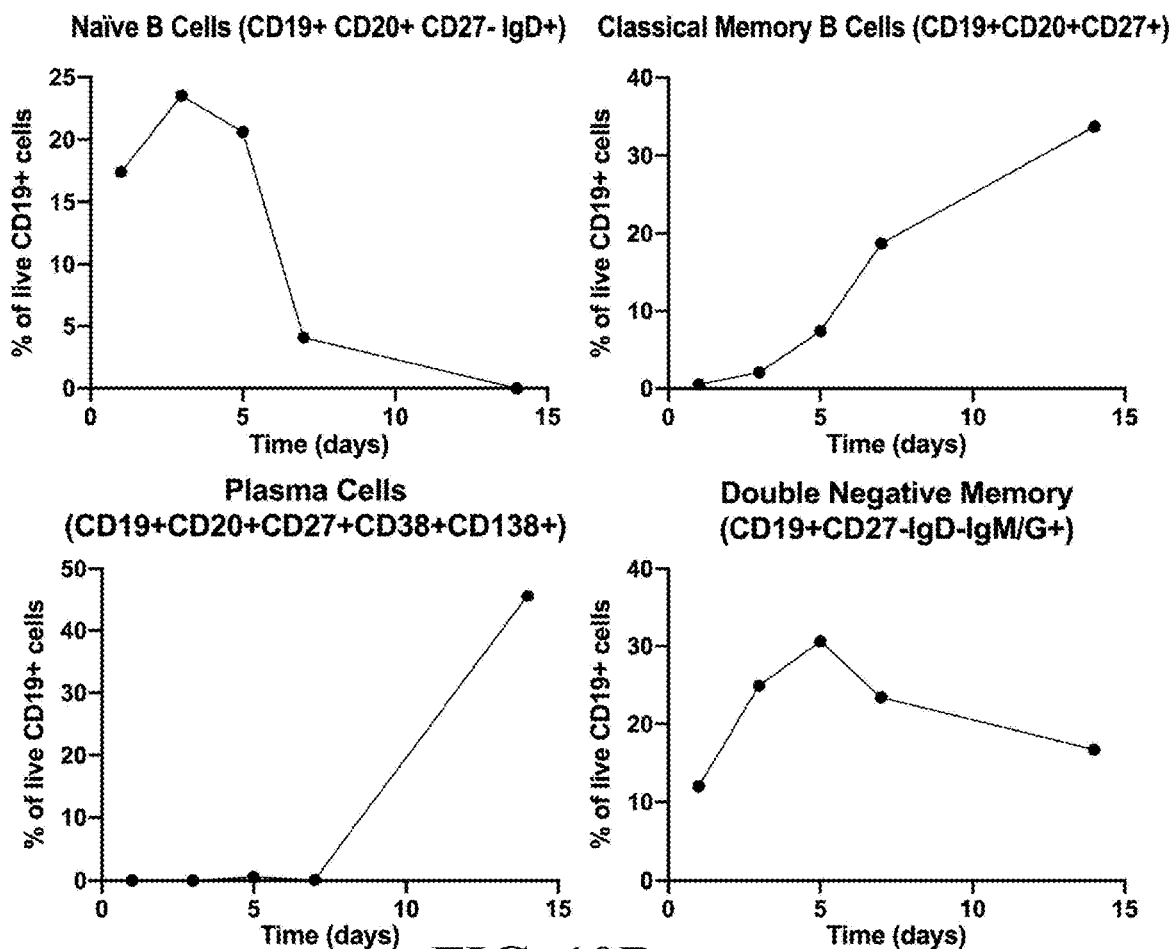

FIGS. 10A-10B show maturation of B cells from stem cell to plasma cell (FIG. 10A) and amount of naïve B cells, classical memory B cells, plasma cells, and double negative memory B cells in the live B cell population as a percentage of live CD19 positive cells over time (FIG. 10B).

Example 6—Functionalization of B Cells

Figure 11C:
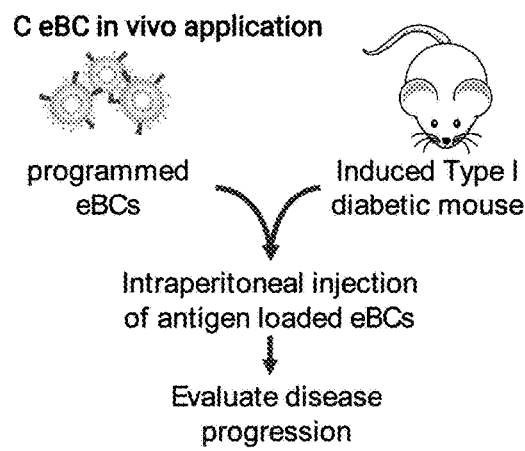

Examples 1-4 demonstrate engineering of B cells to target specific T-cells through interaction of a peptide-MHC complex and the target T-cell in a T-cell antigen specific manner. The engineered B cells can be modified such that they are functionalized to modulate the function and/or activity of the target T-cell with which they bind and/or interact with in an antigen specific manner. FIGS. 11A and 11C—shows schematics for engineered B cell functionalization (FIG. 11A) and an exemplary application of the engineered B cells in vivo (FIG. 11C).

The engineered B cells can be further functionalized (beyond e.g. a desired presentation of a desired antigen) to express other genes whose product(s) can be delivered by the engineered B cell to a target T-cell and used to modulate a target T-cell or another T-cell within effective proximity to a target T-cell.

Figure 12:
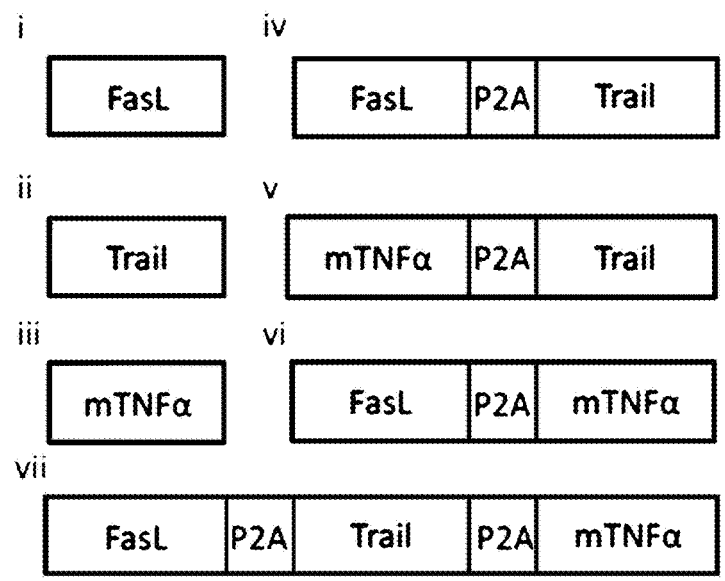
FIG. 12—Schematic of cell death receptor constructs that can be used to by an engineered B cell to induce death of a target T-cell and/or a T-cell in effective proximity to a target T-cell.

In some embodiments, it can be desirable to eliminate the target T-cell. The engineered B cells can be functionalized by modifying them to express and/or deliver a death inducing molecule. Activated T-cells express multiple putative death receptors, which are proteins containing an intracellular death domain and inducing Caspase-mediated cell death upon interaction with their cognate ligands (Donepudi et al. Mol. Cell. 11 (2003) 543-9. http://www.ncbi.nlm.nih.gov/pubmed/12620240) Reported death receptors are Fas (Suda et al., J. Exp. Med. 186 (1997) 2045-50), TrailR1 (Ikeda et al., J. Immunol. 185 (2010) 5259-5267. doi: 10.4049/jimmunol.0902797), TNFR1 and TNFR2 (Zhang et al. Oncotarget. 8 (2017) 63799-63812) that all have been implicated in the induction of cell death of activated T-cells during the contraction phase of an immune response (Garrod et al. Cell Rep. 2 (2012) 1438-1447). B cells, such as primary human B cells can be engineered to express one or more corresponding ligands (e.g. FasL, Trail and membrane-bound TNFα that serves as ligand for TNFR1 and TNFR2; short mTNFα) such as any of those combinations shown in FIG. 12.

B cells further express surface molecules (CD80 and CD86) that interact with a pro-survival receptor (CD28) on T-cells (Linsley et al., Immunity. 1 (1994) 793-801. doi: 10.1016/51074-7613(94)80021-9. Upon simultaneous MHC-TCR binding and co-stimulation T-cell activation is induced. The engineered B cells can have CD80 and/or CD86 expression eliminated or reduced such that the engineered B cell does not stimulate survival in an T-cell with which it interacts in an antigen specific manner.

Example 7—Cross-Presentation Pathway Gene Screen

A general approach to screen for cross-presentation is shown in FIG. 1. Antigen presentation by B cells is strongly increased upon uptake of proteins via binding to the B cell receptor Onabajo et al. 2008. J. Immunol. 180: 6685 LP-6695. doi:10.4049/jimmunol.180.10.6685. Primary human B cells express different B cell receptors, making it difficult to deliver a given antigen equally into all cells. To achieve equal targeting, a transgenic B cell receptor (BCR), specific for a Flag tag can be expressed in the B cell (see also Example 2). As BCRs are membrane-bound antibodies, the transgenic BCR can be based on known Flag-reactive antibodies Entzminger et al. 2017. Sci. Rep. 7:10295: doi.10.1038/s41598-017-10737-9. The transgenic Flag-tag specific BCR can be expressed in primary B cells using a lentivector. Upon incubation of these cells with Flag-tagged proteins, these proteins will bind the BCR, be taken up by endocytosis and processed by the cell-intrinsic cross-presentation pathways before being presented on the cell surface on MHC I molecules J. Magarian Blander. 2018. Annu. Rev. Immunol. 36: doi:10.1146/annurev-immunol-041015-055523. A previously reported, fluorescently labelled, T-cell receptor-like nanobody targeting a known peptide-MHCI complex (Stewart-Jones, et al. Sci. Rep. 8 (2018) 1-9. doi:10.1038/s41598-018-30358-0) can be used to evaluate the amount of cross-presented peptide by flow cytometry. A schematic of the at least the screening procedure is shown in FIG. 1. Briefly, a lentivector library encoding guide RNAs (gRNA) and the transgenic B cell receptor (BCR) are used to transduce B cells, followed by antibiotic selection. Next, CAS9 protein is electroporated into B cells to result in knockout B cells. These cells are then trained with Flag-peptide and incubated with an anti-peptide-MHCI nanobody. The cells with bound fluorescent nanobody are then sorted by flow cytometry into bins expressing higher or lower peptide-MHCI (green shaded peak) than wildtype cells (blue shaded peak) incubated with the same peptide. Finally, targeted next generation sequencing is used to identify genes resulting in higher or lower cross-presentation.

Human primary B cells can be cultured for up to 18 days and are amenable to genome engineering using CRISPR-Cas9 (Su et al. J. Immunol. 197 (2016) 4163-4176. doi: 10.4049/jimmunol.1502193). Recently developed genome engineering techniques in primary human B cells rely on the delivery of CRISPR-Cas9 ribonucleoproteins (RNPs) (Johnson et al. Sci. Rep. 8 (2018) 1-9. doi:10.1038/s41598-018-30358-0 and Wu et al., J. Immunol. Methods. 457 (2018) 33-40. doi:10.1016/j.jim.2018.03.009). One drawback of using RNPs is that they cannot efficiently be applied in a pooled format, as it would be difficult to readout the guides afterwards (Jonathan Schmid-Burgk, personal communication). To overcome this limitation, pseudotyped lentivectors can be used to deliver a library of guide RNAs at a MOI of 0.3[24], thus ensuring the presence of a single targeting guide RNA per cell. A previously optimized human guide RNA library can be used (Doench et al., Nat. Biotechnol. 34 (2016) 184. https://doi.org/10.1038/nbt.3437) and a lentiviral backbone can be designed that allows to express the transgenic BCR and the guide RNA. Subsequently, a Cas enzyme (e.g. Cas 9) can be introduced into the cells via a suitable delivery method (e.g. electroporation) which can induce the targeted knock-out of a single gene per cell (Shifut et al. Cell. 175 (2018) 1958-1971.e15. doi:10.1016/j.cell.2018.10.024). Considering 77441 guide RNAs in the Brunello library (Doench et al., Nat. Biotechnol. 34 (2016) 184. https://doi.org/10.1038/nbt.3437) and a coverage of 500-fold at a MOI of 0.3 I will transduce $1.3*10_8$ B cells extracted from human blood products (i.e. buffy coats) (Joung et al. Nat. Protoc. 12 (2017) 828-863. doi:10.1038/nprot.2017.016). Electroporation of Cas9 RNPs into primary human B cells has been reported to yield up to 80% gene knockout frequencies (Johnson et al. Sci. Rep. 8 (2018) 1-9. doi:10.1038/s41598-018-30358-0). Considering that reported values refer to knockout frequency that only considers out-of-frame indels, it is estimated that the suggested numbers will result in >400-fold coverage of each guide in the library after Cas9 electroporation. The screen can be analyzed by sorting for the highest and lowest MHC-I presenting cells using FACS. The sorted cells can be lysed, and their mRNA analyzed by a suitable method, e.g. RNAseq, or other cDNA-based platform (e.g. next-generation sequencing (NGS) technique. For example, mRNA can be transcribed into cDNA, which can subsequently analyzed by NGS on an Illumina NextSeq platform. Known bioinformatics pipelines can be sued to analyze the sequencing results (Joung et al. Nat. Protoc. 12 (2017) 828-863. doi: 10.1038/nprot.2017.016; Parnas et al. Genome-wide CRISPR Screen in Primary Immune Cells to Dissect Regulatory Networks, Cell. 162 (2015) 675-686. doi:10.1016/j.cell.2015.06.059; and Shalem et al., Science (80-.). 343 (2014) 84 LP-87. doi:10.1126/science.1247005).

Alternatively, or additionally, cross-presentation genes can be identified by screening of a selected list of genes in primary human B cells, in the case that cell numbers or viability represent the major limiting factors.

Alternatively, or additionally, cross-presentation genes can be identified by screening of a genome-wide library in 293T cells, engineered to cross-present antibody-bound antigen by expression of FcγRIIA (Giodini et al. Proc. Natl. Acad. Sci. 106 (2009) 3324-3329. doi:10.1073/pnas.0813305106).

Example 8—In Vivo Depletion of Antigen-Specific T-Cells Using eBCs in a Humanized T1D Mouse Model Induction of type 1 diabetes (T1D) in a humanized mouse model has been described before (Tan et al., PNAS, 12 (2017) 187-215. doi:10.1146/annurev-pathol-052016-100332). Briefly, naiive CD4+ T-cells from a humanized donor mouse are extracted and transduced with a lentivector encoding for a TCR recognizing a peptide from the insulin B chain (InsB:9-23). Subsequently, these auto-reactive T-cells are intravenously injected into a recipient mouse that has been treated with streptozotocin.

Autologous B cells can be isolated from humanized mice and transduce these cells ex vivo with lentivectors to express the transgenic BCR that allows loading and a combination of death factors. Optionally, co-stimulatory molecules (CD80 and/or CD86) and/or gene(s) identified in a cross-presentation screen to achieve efficient MHCI presentation ex vivo (FIG. 10A). The eBCs can be engineered to express insulin or loaded with an ex vivo with Flag-tagged insulin to induce MHCI and MHCII presentation of insulin-derived peptides (FIG. 3B). Using an adoptive cell therapy approach, the resulting engineered eBC can be transferred back into the diabetic mice (FIG. 3C). The changes in the number of insulin reactive CD4+ and CD8+ T-cells during treatment, using the ex vivo expansion protocol discussed elsewhere herein.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. An engineered B cell comprising:
a modified antigen presentation pathway as determined by detecting expression of an MHCI-reporter antigen complex and/or an MHCII-reporter antigen complex on the surface of the engineered B cell, wherein the modified antigen presentation pathway comprises one or more modified genes selected from LAMP2, PSMB8, TAP1, TAP2, ERAP1, CANX, CALR, TAPBP, PDIA3, CD74, HLA-DMA, HLA-DMB, HLA-DOA, TAPBPL, B2M, ERAP2, HLA-E, HLA-F, HLA-G, TLR4, TICAM1, LNPEP, TFEB, RAB27A, SEC61A1, RAB3A, RAB3B, BCAP31, EEA1, LAMP1, RAB4A, RAB5A, RAB11A, RAB7A, RHOB, PKN1, PIK3C3, TF, WASF1, DIAPH1, SYK, ICAM1, Cathepsin L, Cathepsin S, Cathepsin D, Cathepsin B, V-aTPase, NOX2, GILT, AAA, ATPase p97, Sec61, TAP, ERAP, IRAP, Sec22b, syntaxin 4, SNAP23, UNC93B1, MAPK, MAPKKK, MAPKK, p38, JNK, ERK1/2, MMK3, MKK6, protein kinase C (PKC) alpha, PKC beta I, PKC beta II, atypical PKC ζ, PKC λ/ι, PKC δ, PKC ε, PKC θ, toll-like receptor (TLR)-1, TLR-2, TLR-4, TLR-5, TLR-7, and TLR-9, INF-gamma, IL-4, TNF-alpha, JAK, STAT1, STAT2, STAT3, RhoA, Cdc42, Rac1, Rho kinase; and
inducible or constitutive expression of one or more T-cell modulating agents selected from the group consisting of: CD27, CD28, CD40, CD122, CD137, OX40, GITR, ICOS CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SUP-1 TIM, TNF, CD95L (FasL or Fas ligand), TRAIL, TL1A, and IL-2.

2. The engineered B cell of claim 1, wherein the modified antigen presentation pathway is capable of processing and presenting an antigen such that the engineered B cell is capable of antigen-specific binding with a target T-cell and wherein the antigen is an extracellular antigen, an intracellular antigen produced by the engineered B cell, or both, wherein antigen-specific binding capability is measured by specifically detecting the MHC I-reporter antigen complex or the MHC II-reporter antigen complex on the engineered B cell.

3. The engineered B cell of claim 1, wherein the modified antigen presentation pathway comprises one or more modifications in one or more cross-presentation pathway genes in the cross-presentation pathway such that the engineered B cell overexpresses one or more genes in the cross-presentation pathway, under expresses one or more genes in the cross-presentation pathway, lacks one or more genes in the cross-presentation pathway, or any combination thereof.

4. The engineered B cell of claim 1, wherein the engineered B cell has increased MHC I extracellular antigen presentation relative to an unmodified antigen presenting cell.

5. The engineered B cell of claim 1, wherein the engineered B cell is capable of being loaded with an extracellular antigen, is loaded with an extracellular antigen, or both, and wherein the extracellular antigen is optionally a peptide or polypeptide that optionally comprises an epitope tag.

6. The engineered B cell of claim 5, wherein the engineered B cell expresses an engineered B cell receptor capable of specifically interacting with the epitope tag.

7. The engineered B cell of claim 2, wherein the antigen is a target T-cell antigen.

8. The engineered B cell of claim 2, wherein the target T-cell is a
   a. CD8+ T-cell, CD4+ T-cell, CD25+ T-cell, or a combination thereof;
   b. engineered T-cell, wherein the engineered T-cell is optionally a CAR T-cell;
   c. non-pathogenic T-cell
   d. pathogenic T-cell;
   e. autoreactive T-cell; or
   f. any combination thereof.

9. The engineered B cell of claim 8, wherein the one or more T-cell modulating agents is/are capable of
   a. eliminating or inhibiting one or more functions of the target T-cell and/or a cell within effective proximity of the target T-cell;
   b. activating one or more functions the target T-cell and/or a cell within effective proximity of the target T-cell; or
   c. both (a) and (b).

10. The engineered B cell of claim 1, wherein the one or more T cell modulating agents are immune checkpoint molecules, capable of inducing T-cell death, or both.

11. The engineered B cell of claim 1, wherein the engineered B cell is capable of antigen-specific binding of a target T-cell, wherein antigen-specific binding capability is measured by specifically detecting an MHC I-antigen complex or an MHC II-antigen complex on the engineered B cell.

12. The engineered B cell of claim 1, wherein the engineered B cell further comprises
   a. a SynNotch receptor, a MESA receptor, or both and wherein expression, activation, or both of the one or more T-cell modulating agents is induced by activation of the SynNotch receptor, MESA receptor, or both;
   b. a hemichannel capable of forming a gap junction between the engineered B cell and a hemichannel present on the target T-cell;
   c. a trogocytic inducer, wherein the trogocytic inducer is capable of being expressed the surface of the engineered B cell, is optionally expressed on the surface of the engineered B cell, or both; or
   d. a combination thereof.

13. The engineered B cell of claim 1, wherein the engineered B cell is autologous.

14. The engineered B cell of claim 1, wherein the engineered B cell is allogeneic.

15. The engineered B cell of claim 1, wherein the engineered B cell is capable of self-inactivation or suicide.

16. A pharmaceutical formulation comprising:
   an engineered B cell of claim 1; and
   a pharmaceutically acceptable carrier.

17. The engineered B cell of claim 1, wherein the modified antigen presentation pathway further comprises a modified MDY88 gene.

18. The engineered B cell of claim 1, wherein the modified antigen presentation pathway further comprises a modified HLA-A gene, HLA-B gene, HLA-C gene, or any combination thereof.

* * * * *

UNITED STATES PATENT AND TRADEMARK OFFICE
CERTIFICATE OF CORRECTION

Page 1 of 1

PATENT NO. : 12,195,723 B2
APPLICATION NO. : 17/093011
DATED : January 14, 2025
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 395 days.

Signed and Sealed this
Eighth Day of July, 2025

Coke Morgan Stewart
*Acting Director of the United States Patent and Trademark Office*